(12) United States Patent
Schneekloth, Jr. et al.

(10) Patent No.: US 11,014,902 B2
(45) Date of Patent: *May 25, 2021

(54) MYC G-QUADRUPLEX STABILIZING SMALL MOLECULES AND THEIR USE

(71) Applicant: The United States of America, as represented by the Secretary, Department of Health and Human Services, Bethesda, MD (US)

(72) Inventors: John Schneekloth, Jr., Frederick, MD (US); John Simmons, Bethesda, MD (US); Kenneth Felsenstein, Bethesda, MD (US); Beverly Mock, Bethesda, MD (US); Lindsey Saunders, Frederick, MD (US); David Calabrese, Frederick, MD (US); Elena Leon, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/835,102

(22) Filed: Mar. 30, 2020

(65) Prior Publication Data

US 2020/0308128 A1 Oct. 1, 2020

Related U.S. Application Data

(60) Continuation of application No. 16/218,341, filed on Dec. 12, 2018, now Pat. No. 10,604,499, which is a division of application No. 15/541,676, filed as application No. PCT/US2016/012222 on Jan. 5, 2016, now Pat. No. 10,196,372.

(60) Provisional application No. 62/099,938, filed on Jan. 5, 2015.

(51) Int. Cl.

| C07D 307/84 | (2006.01) |
|---|---|
| A61K 31/343 | (2006.01) |
| A61P 35/00 | (2006.01) |
| A61K 31/397 | (2006.01) |
| A61K 31/4025 | (2006.01) |
| A61K 31/439 | (2006.01) |
| A61K 31/4525 | (2006.01) |
| A61K 31/496 | (2006.01) |
| A61K 31/5377 | (2006.01) |
| A61K 31/55 | (2006.01) |
| A61K 45/06 | (2006.01) |
| C07D 405/06 | (2006.01) |
| C07D 471/08 | (2006.01) |

(52) U.S. Cl.
CPC .......... *C07D 307/84* (2013.01); *A61K 31/343* (2013.01); *A61K 31/397* (2013.01); *A61K 31/4025* (2013.01); *A61K 31/439* (2013.01); *A61K 31/4525* (2013.01); *A61K 31/496* (2013.01); *A61K 31/5377* (2013.01); *A61K 31/55* (2013.01); *A61K 45/06* (2013.01); *C07D 405/06* (2013.01); *C07D 471/08* (2013.01)

(58) Field of Classification Search
CPC ...... A61P 35/00; A61K 31/343; C07D 307/84
See application file for complete search history.

(56) References Cited

U.S. PATENT DOCUMENTS

| 4,874,759 A | 10/1989 | Tahara et al. |
|---|---|---|
| 5,220,059 A | 6/1993 | Brooks et al. |
| 5,773,467 A | 6/1998 | Dyke et al. |
| 5,972,936 A | 10/1999 | Dyke et al. |
| 8,138,356 B2 | 3/2012 | Chaudhary et al. |
| 2004/0110820 A1 | 6/2004 | Hurley |
| 2005/0209213 A1 | 9/2005 | Ishihara et al. |
| 2006/0194816 A1 | 8/2006 | Zhang |
| 2007/0254877 A1 | 11/2007 | Nishikimi et al. |
| 2009/0291963 A1 | 11/2009 | Schadt et al. |
| 2012/0071523 A1 | 3/2012 | Djaballah et al. |
| 2013/0217730 A1 | 8/2013 | Cossio Mora et al. |
| 2013/0338201 A1 | 12/2013 | Song |

OTHER PUBLICATIONS

Balasubramanian et al., "Targeting G-quadniplexes in Gene Promoters: A Novel Anticancer Strategy?" *Nat Rev Drug Discov.* 10.4: 261-275, Apr. 2011.
Berg et al., "Small-Molecule Antagonists of Myc/Max Dimerization Inhibit Myc-Induced Transformation of Chicken Embryo Fibroblasts," *Proc Natl Acad Sci USA* 99.6: 3830-3835, Mar. 2002.
Bidzinska et al., "G-quadraplex Structures in the Human Genome as Novel Therapeutic Targets," *Molecules* 18.10: 12368-12395, Oct. 2013.
Brooks et al., "Targeting MYC Expression through G-quadruplexes," *Genes Cancer* 1.6: 641-649, Jun. 2010.
ChemBridge Product No. 6238398, available at https://www.hit2lead.com/screening-compounds/6238398, as accessed Jul. 5, 2017.
ChemBridge Product No. 6240697, available at https://www.hit2lead.com/screening-compounds/6240697, as accessed Jul. 5, 2017.
ChemBridge Product No. 9127171, available at https://www.hit2lead.com/screening-compounds/9127171, as accessed Jul. 5, 2017.
ChemBridge Product No. 9139363, available at https://www.hit2lead.com/screening-compounds/9139363, as accessed Jul. 5, 2017.
ChemDiv Product No. D089-0474, , available at http://chemistryondemand.com:8080/eShop/search_results.jsp?jme_mol=&smiles=D089-0350&s_type=txt&idnumber=D089-0474, as accessed Jul. 5, 2017.

(Continued)

*Primary Examiner* — Bruck Kifle
(74) *Attorney, Agent, or Firm* — Klarquist Sparkman, LLP

(57) ABSTRACT

Methods for treating a tumor, such as a benign or malignant tumor, are disclosed herein. The methods include administering a therapeutically effective amount of a small molecule that selectively binds to and stabilizes G-quadruplex DNA in the promoter of the c-MYC gene to the subject. The methods are also of use to decrease the size and/or number of metastases. Compounds for use in the disclosed methods are also provided.

26 Claims, 14 Drawing Sheets

Specification includes a Sequence Listing.

(56) References Cited

OTHER PUBLICATIONS

ChemDiv Product No. D089-0350, , available at http://chemistryondemand.com:8080/eShop/compound_info.jsp?molid=416319&logP=4.98&saltdata=null&cid=D089-0350, as accessed Jul. 5, 2017.

ChemDiv Product No. D089-0559, , available at http://chemistryondemand.com:8080/eShop/search_results.jsp?jme_mol=&smiles=D089-0350&s_type=txt&idnumber=D089-0559, as accessed Jul. 5, 2017.

Chen et al., "Small Molecules Targeting c-Myc Oncogene: Promising Anti-Cancer Therapeutics," *Int J Biol Sci* 10.10: 1084-1096, Sep. 2014.

Dash et al., "G-quadruplex Recognition by Bis-indole Carboxamides," *Chem Commun (Camb)* 26: 3055-3057, Jul. 2008.

Dash et al., "Synthesis of Bis-indole Carboxamides as G-Quadruplex Stabilizing and Inducing Ligands," *Chemistry* 18.2: 554-564, Jan. 2012.

Felsenstein et al., "Small Molecule Microarrays Enable the Identification of a Selective, Quadruplex-Binding Inhibitor of MYC Expression," *ACS Chem Biol* 11.1: 139-148, Jan. 2016.

Hranjec et al., "Antiproliferative Potency of Novel Benzofuran-2-carboxamides on Tumour Cell Lines: Cell Death Mechanisms and Determination of Crystal Structure," *Eur J Med Chem* 59: 111-119, Jan. 2013.

Lee et al., "Studies on Benzofuran-7-carboxamides as Poly (ADP-ribose) Polymerase-1 (PARP-1) Inhibitors," *Bull Korean Chem Soc.* 33.4: 1147-1153, 2012.

Marugán et al., "Design, Synthesis, and Biological Evaluation of Novel Potent and Selective αvβ3/αvβ5 Integrin Dual Inhibitors with Improved Bioavailability. Selection of the Molecular Core," *J Med Chem.* 48.4: 926-934, Feb. 2005. (Abstract Only).

McLuckie et al., "G-quadruplex DNA as a Molecular Target for induced Synthetic Lethality in Cancer Cells," *J Am Chem Soc.* 135.26: 9640-9643, Jul. 2013.

National Center for Biotechnology Information. PubChem Compound Database; CID=7540297, https://pubchem.ncbi.nlm.nih.gov/compound/7540297, as accessed Jul. 5, 2017.

National Center for Biotechnology Information. PubChem Compound Database; CID=16461759, https://pubchem.ncbi.nlm.nih.gov/compound/16461759, as accessed Jul. 5, 2017.

Otava Chemical Product No. 7018860259, available at http://www.otavachemicals.com/products/search-our-compounds-on-line-by-structure, as accessed Jul. 5, 2017.

Otava Chemical Product No. 7018860288, available at http://www.otavachemicals.com/products/search-our-compounds-on-line-by-structure, as accessed Jul. 5, 2017.

Otava Chemical Product No. 7018860345, available at http://www.otavachemicals.com/products/search-our-compounds-on-line-by-structure, as accessed Jul. 5, 2017.

Otava Chemical Product No. 7018860464, available at http://www.otavachemicals.com/products/search-our-compounds-on-line-by-structure, as accessed Jul. 5, 2017.

Otava Chemical Product No. 7018860541, available at http://www.otavachemicals.com/products/search-our-compounds-on-line-by-structure, as accessed Jul. 5, 2017.

Otava Chemical Product No. 7018860542, available at http://www.otavachemicals.com/products/search-our-compounds-on-line-by-structure, as accessed Jul. 5, 2017.

Otava Chemical Product No. 7018860553, available at http://www.otavachemicals.com/products/search-our-compounds-on-line-by-structure, as accessed Dec. 11, 2015.

Otava Chemical Product No. 7018860556, available at http://www.otavachemicals.com/products/search-our-compounds-on-line-by-structure, as accessed Jul. 5, 2017.

Otava Chemical Product No. 7018860559, available at http://www.otavachemicals.com/products/search-our-compounds-on-line-by-structure, as accessed Jul. 5, 2017.

Siddiqui-Jain et al., "Direct Evidence for a G-quadruplex in a Promoter Region and its Targeting with a Small Molecule to Repress c-MYC Transcription," *Proc Natl Acad Sci USA* 99.18: 11593-11598, Sep. 2002.

NHEIII₁ Region of *c-Myc*
(c-MycPu27): 5'-T<u>GGGG</u>A<u>GGG</u>T<u>GGGG</u>A<u>GGG</u>T<u>GGGG</u>AAGG-3'
(c-MycPu22): 5'-TGA<u>GGG</u>T<u>GGG</u>TA<u>GGG</u>T<u>GGG</u>TAA-3'

$\Delta T_m = 2.1 \pm 0.5$ °C (circular dichroism)
$K_d = 4.5 \pm 1.4$ µM (SPR)

Untreated    1 µM    5 µM    10 µM    20 µM    50 µM    100 µM

WT: 5'-A<u>GGG</u>T<u>GGGG</u>A<u>GGG</u>T<u>GGGG</u>-3' (Forms G4)
Mutant: 5'-A<u>GGG</u>TAAAA<u>GGG</u>T<u>GGGG</u>-3' (Does not form G4)

Time of treatment (hours)
1: Exon 1 (quadruplex driven)
2: Exon 2 (no quadruplex)

Untreated    10 µM

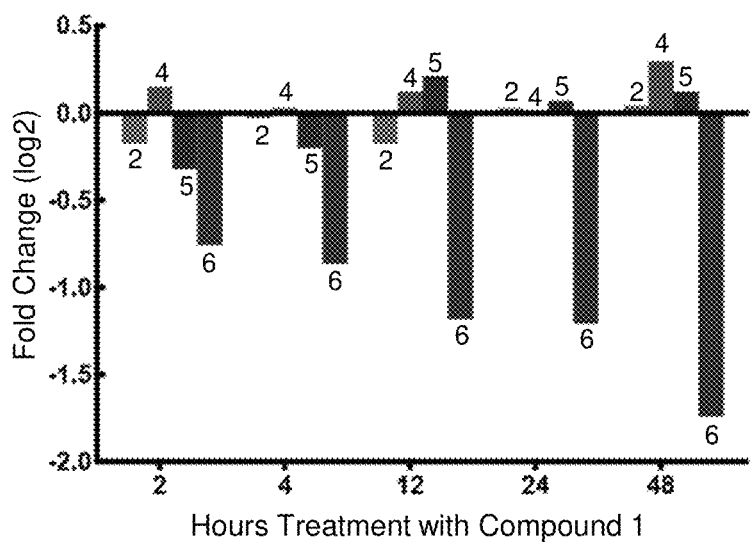
FIG. 6A
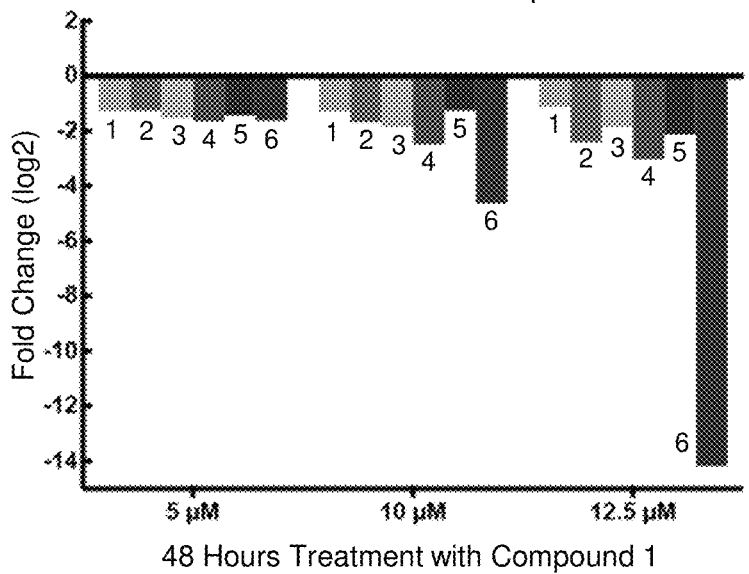
FIG. 6B
FIG. 6C
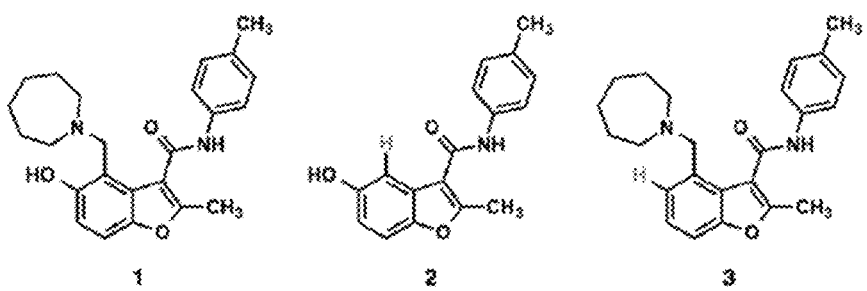

compound remains after 72h at 20 μM in 2% DMSO/culture media
by LC/MS; data suggests partial decomposition but not to
o-quinone methide Major product on small scale Going to repeat with p-CF₃, shorter reaction time Synthesis of Analogs 48 hr. treatment- L363

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide

<400> SEQUENCE: 1
tggggagggt ggggagggtg gggaagg                                        27

<210> SEQ ID NO 2
<211> LENGTH: 22
<212> TYPE: DNA
<213> ORGANISM: Artificial sequence
<220> FEATURE:
<223> OTHER INFORMATION: oligonucleotide

<400> SEQUENCE: 2
tgagggtggg tagggtgggt aa                                             22

<210> SEQ ID NO 3
<211> LENGTH: 18
```

```
<212> TYPE: DNA
<213> ORGANISM: artificial sequence
<220> FEATURE:
<223> OTHER INFORMATION: oligonucleotide

<400> SEQUENCE: 3
agggtgaaaa gggtgggg                                            18

<210> SEQ ID NO 4
<211> LENGTH: 25
<212> TYPE: DNA
<213> ORGANISM: artificial sequence
<220> FEATURE:
<223> OTHER INFORMATION: oligonucleotide

<400> SEQUENCE: 4
atcgatcgct tctcgtcctt cccca                                    25
```

MYC G-QUADRUPLEX STABILIZING SMALL MOLECULES AND THEIR USE

CROSS REFERENCE TO RELATED APPLICATIONS

This is a continuation of U.S. application Ser. No. 16/218,341, filed Dec. 12, 2018, which is a divisional of U.S. application Ser. No. 15/541,676, filed Jul. 5, 2017, now U.S. Pat. No. 10,196,372, issued Feb. 5, 2019, which is the U.S. National Stage of International Application No. PCT/US2016/012222, filed Jan. 5, 2016, which was published in English under PCT Article 21(2), which in turn claims the benefit of U.S. Provisional Application No. 62/099,938, filed Jan. 5, 2015. Each of the prior applications is incorporated by reference herein in its entirety.

FIELD OF THE DISCLOSURE

This relates to small molecule compounds that bind and stabilize the G-quadruplex DNA formation in the promoter of the c-MYC gene, and therefore can be used to reduce expression of the c-MYC gene in cells. The small molecule compounds can be used, for example, in methods of treating or inhibiting a tumor having increased c-MYC expression in a subject.

BACKGROUND

The oncogenic transcription factor c-Myc has a pleiotropic role in a wide range of cell processes and is deregulated in some 70% of human cancers. However, targeting the c-Myc protein directly has proven to be difficult due to a lack of well-defined pockets amenable to small molecule binding. An alternative approach for suppressing c-Myc levels in the cell is through stabilization of the G-quadruplex DNA formation (G4) present in the promoter of the c-MYC gene. Expression of the proto-oncogene c-MYC is regulated by a 27 base pair (Pu27) sequence found in the nuclease hypersensitive element III(1) region ($NHEIII_1$) of the c-MYC gene known to form a G4. Formation of the quadruplex in this sequence is believed to result in a "kink" in the DNA that prevents the polymerase from continuing along its reading frame, ultimately resulting in downregulation of the c-MYC gene.

The use of small molecules to stabilize the G4 conformation and consequently decrease c-MYC expression is an attractive therapeutic goal in cancers where c-Myc is overexpressed. Unfortunately, although some quadruplex stabilizing small molecules have been shown to reduce c-Myc expression in cells, these agents may not be selective and activity cannot always be attributed to a c-MYC quadruplex-dependent mechanism of action. New classes of potent, selective quadruplex stabilizing agents that are active in tissue culture models would be of substantial utility as reagents to study c-Myc biology as well as potential therapeutics.

SUMMARY

The identification and characterization of a new class of small molecule c-MYC G4 ligands that selectively bind to and stabilize the G4 in the c-MYC promoter region and silence c-Myc expression is described herein. The compounds are useful, for example, in methods of reducing or inhibiting c-MYC expression in cells (such as cancer cells), as well as in methods of treating or inhibiting a c-MYC expressing tumor in a subject.

In some embodiments, a method of decreasing c-MYC expression in a cell is provided. The method comprises contacting the cell with an effective amount of a compound, or a pharmaceutically acceptable salt or ester thereof, having a structure of:

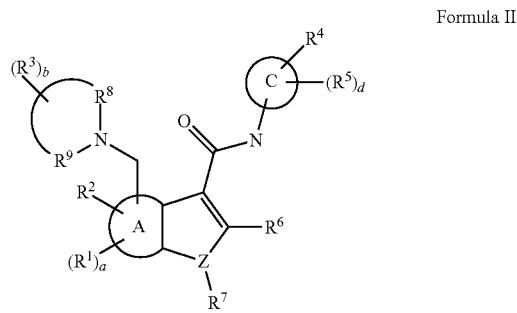

Formula II wherein:
A is a 6 membered aryl ring;
C is a 6-membered aryl ring;
each $R^1$ is independently selected from hydrogen or optionally-substituted lower alkyl;
a is 0, 1, or 2;
$R^2$ is selected from hydroxyl or halogen;
$R^8$ and $R^9$ together with the linking nitrogen atom form a 4 to 7 membered optionally-substituted N-heterocyclic ring;
each $R^3$ is independently selected from hydrogen, halogen, lower haloalkyl, or optionally-substituted lower alkyl;
b is 0 to 4;
$R^4$ is selected from halogen, lower haloalkyl, or optionally-substituted lower alkyl;
each $R^5$ is independently selected from hydrogen, halogen, lower haloalkyl, or optionally-substituted lower alkyl;
d is 0, 1, or 2;
$R^6$ is selected from methyl, trifluoromethyl, or phenyl;
Z is selected from nitrogen or oxygen; and
if Z is nitrogen, $R^7$ is selected from hydrogen, hydroxyl, halogen, lower haloalkyl, optionally-substituted lower alkyl, and if Z is oxygen, $R^7$ is not present. In some such embodiments, a is 0, $R^2$ is hydroxyl, and/or $R^6$ is methyl. In some such embodiments, $R^4$ is lower haloalkyl (such as trifluoromethyl) and/or d is 0. In some such embodiments, $R^8$ and $R^9$ together with the linking nitrogen atom form optionally-substituted pyrrolidine, optionally-substituted imidizolidine, optionally-substituted pryazolidine, optionally-substituted piperidine, optionally-substituted piperazine, or optionally-substituted azepane. For example, $R^8$ and $R^9$ together with the linking nitrogen atom form pyrrolidine, imidizolidine, pryazolidine, piperidine, piperazine, or azepane.

In some embodiments of the method of decreasing c-MYC expression in a cell, the method can include contacting the cell with an effective amount of a compound, or a pharmaceutically acceptable salt or ester thereof, having a structure of one of Compounds 1, 3, 6, 10, 12-13, 18-20, 22-23, 26, or 28-29 as disclosed herein. In some embodiments of the method of decreasing c-MYC expression in a cell, the method can include contacting the cell with an effective amount of a compound, or a pharmaceutically acceptable salt or ester thereof, having a structure of Compounds 23.

In additional embodiments, compounds for use in the disclosed methods are provided. In some embodiments, a compound, or a pharmaceutically acceptable salt or ester thereof, is provided, having a structure of Formula III:

Formula III

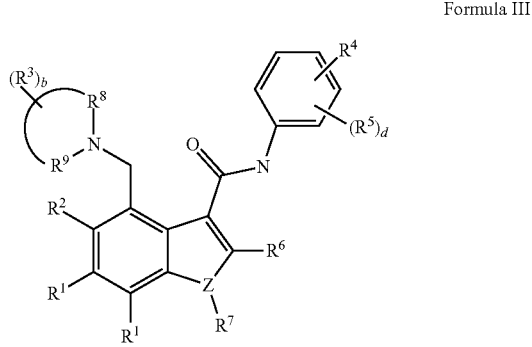

wherein:
each $R^1$ is independently selected from hydrogen or optionally-substituted lower alkyl;
$R^2$ is selected from hydroxyl or halogen;
$R^8$ and $R^9$ together with the linking nitrogen atom form a 4 to 7 membered optionally-substituted N-heterocyclic ring;
each $R^3$ is independently selected from halogen, lower haloalkyl, or optionally-substituted lower alkyl;
b is 0 to 4;
$R^4$ is trifluoromethyl;
each $R^5$ is independently selected from halogen, lower haloalkyl, or optionally-substituted lower alkyl;
d is 0, 1, or 2;
$R^6$ is selected from methyl, trifluoromethyl, or phenyl;
Z is selected from nitrogen or oxygen; and
if Z is nitrogen, $R^7$ is selected from hydrogen, hydroxyl, halogen, lower haloalkyl, or optionally-substituted lower alkyl, and if Z is oxygen, $R^7$ is not present; and
with the proviso that the compound does not comprise the structure set forth as any one of structures 12-13, 17-20, or 36-43. In some embodiments, a compound, or a pharmaceutically acceptable salt or ester thereof, having a structure of one of compounds 23-29, or 34 is provided. Pharmaceutical composition comprising a disclosed compound and at least one pharmaceutically acceptable additive are also provided.

The foregoing and other features and advantages of this disclosure will become more apparent from the following detailed description of several embodiments which proceeds with reference to the accompanying figures.

BRIEF DESCRIPTION OF THE FIGURES

The patent or application file contains at least one drawing executed in color.

FIGS. 6A-6C show a series of graphs illustrating the effect of Compound 1 treatment on gene expression. (A) Treatment with 10 μM of Compound 1 for various times reduces c-Myc expression of while minimally affecting expression of other G-quadruplex containing genes, as evaluated using Nanostring assays. (B) Treatment with 5, 10 or 12.5 μM of Compound 1 for 48 hours reduces c-Myc expression of while minimally affecting expression of other G-quadruplex containing genes, as evaluated using qPCR analysis (data are the average log 2 value for ΔΔCt of three replicates). (C) A series of analogs of Compound 1 were tested for any effect on c-Myc expression or L363 cell viability. The expression levels of the BCL2 (1), KRAS (2), HIF1A (3), VEGFA (4), Rb1 (5), and c-MYC (6) genes is shown.

SEQUENCES

Figure 1A:
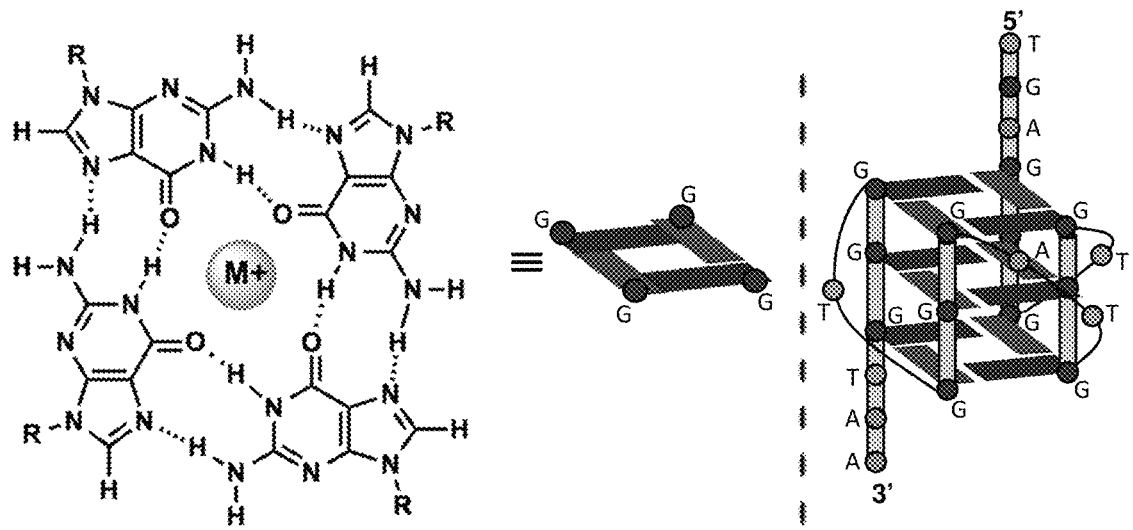
FIGS. 1A and 1B show a set of schematic drawings illustrating the c-MYC Pu22 G-quadruplex and its formation. (A) Schematic drawing of the c-MYC Pu22 G-quadruplex. In structure on right, each circle represents a different nucleotide (indicated as thymine, T, guanine, G, and adenine, A). The quadruplex-forming promoter sequence of the NHE $III_1$ region of wild type c-MycPu27 (SEQ ID NO: 1) and variant c-MycPu22 (SEQ ID NO: 2) are shown. (B) Cartoon depicting reversible formation of G-quadruplex DNA in c-MYC promoter region that controls gene transcription. Stabilization of the quadruplex with a small molecule inhibits transcription.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~4 kb), which was created on Mar. 17, 2020, which is incorporated by reference herein. In the accompanying sequence listing:

SEQ ID NO: 1 is the nucleic acid sequence of a c-MycPu27 G4

SEQ ID NO: 2 is the nucleic acid sequence of a c-MycPu22 G4

SEQ ID NO: 3 is the nucleic acid sequence of a mutant c-MycPu22 that does not form a G4 structure.

SEQ ID NO: 4 is the nucleic acid sequence of an oligonucleotide primer.

DETAILED DESCRIPTION

I. Terms

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Acyl: A group having the structure —C(O)R, where R may be, for example, optionally substituted alkyl, optionally substituted aryl, or optionally substituted heteroaryl. Lower acyl groups are those that contain one to six carbon atoms.

Acyloxy: A group having the structure —OC(O)R—, where R may be, for example, optionally substituted alkyl, optionally substituted aryl, or optionally substituted heteroaryl. Lower acyloxy groups contain one to six carbon atoms.

Administration: To provide or give to a subject an agent, for example, a small molecule compound that selectively binds to G4 quadruplex DNA in the c-MYC promoter, by any effective route. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Co-administration or co-administering refers to administration of at least two therapeutic compounds within the same general time period, and does not require administration at the same exact moment in time (although co-administration is inclusive of administering at the same exact moment in time). Thus, co-administration may be on the same day or on different days, or in the same week or in different weeks. The therapeutic compounds disclosed herein may be included in the same composition or they may each individually be included in separate compositions. In certain embodiments, the two compounds may be administered during a time frame wherein their respective periods of biological activity overlap. Thus, the term includes sequential as well as coextensive administration of two or more compounds.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

Agent: Any substance or any combination of substances that is useful for achieving an end or result; for example, a substance or combination of substances useful for decreasing or reducing tumor growth in a subject. Agents include effector molecules and detectable markers. In some embodiments, the agent is a chemotherapeutic agent. The skilled artisan will understand that particular agents may be useful to achieve more than one result; for example, an agent may be useful as both a detectable marker and a chemotherapeutic agent.

Aliphatic: A group including alkyl, alkenyl, alkynyl, halogenated alkyl and cycloalkyl groups. A lower aliphatic group is a branched or unbranched aliphatic group having from 1 to 10 carbon atoms.

Alkanediyl, cycloalkanediyl, aryldiyl, alkanearyldiyl: A divalent radical derived from aliphatic, cycloaliphatic, aryl, and alkanearyl hydrocarbons.

Alkenyl: A cyclic, branched or straight chain group containing only carbon and hydrogen, and contains one or more double bonds that may or may not be conjugated. Alkenyl groups may be unsubstituted or substituted. Lower alkenyl groups contain one to six carbon atoms.

Alkoxy: A straight, branched or cyclic hydrocarbon configuration and combinations thereof, including from 1 to 20 carbon atoms, preferably from 1 to 6 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

Alkoxycarbonyl: An alkoxy substituted carbonyl radical, —C(O)OR, wherein R represents an optionally substituted alkyl, aryl, aralkyl, cycloalkyl, cycloalkylalkyl or similar moiety.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A lower alkyl group is a saturated branched or unbranched hydrocarbon having from 1 to 6 carbon atoms. Preferred alkyl groups have 1 to 4 carbon atoms. Alkyl groups may be substituted alkyls wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

Alkynyl: A cyclic, branched or straight chain group containing only carbon and hydrogen, and unless otherwise mentioned typically contains one to twelve carbon atoms, and contains one or more triple bonds. Alkynyl groups may be unsubstituted or substituted. A lower alkynyl group is one that contains one to six carbon atoms.

Amine or Amino: A group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

Aminoalkyl: An alkyl group as defined above where at least one hydrogen atom is replaced with an amino group (e.g., —$CH_2$—$NH_2$).

Aminocarbonyl: A group that, alone or in combination, includes an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

Amide or Amido: A group that is represented by the formula —C(O)NRR', where R and R' independently can be a hydrogen, alkyl, alkenyl, alkynyl, aryl, aralkyl, cycloalkyl, halogenated alkyl, or heterocycloalkyl group.

Analog: A molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

Aralkyl: An alkyl group wherein an aryl group is substituted for a hydrogen of the alkyl group. An example of an aralkyl group is a benzyl group.

Aryl: A monovalent unsaturated aromatic carbocyclic group having a single ring (e.g., phenyl) or multiple condensed rings (e.g., naphthyl or anthryl), which can optionally be unsubstituted or substituted. A heteroaryl group is an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

Aryloxy or Heteroaryloxy: A group of the formula —OAr, wherein Ar is an aryl group or a heteroaryl group, respectively.

Cancer: A malignant tumor that has undergone characteristic anaplasia with loss of differentiation, increase rate of growth, invasion of surrounding tissue, and is capable of metastasis. For example, thyroid cancer is a malignant tumor that arises in or from thyroid tissue, and breast cancer is a malignant tumor that arises in or from breast tissue (such as a ductal carcinoma). Residual cancer is cancer that remains in a subject after any form of treatment given to the subject to reduce or eradicate the cancer. Metastatic cancer is a tumor at one or more sites in the body other than the site of origin of the original (primary) cancer from which the metastatic cancer is derived. Cancer includes, but is not limited to, solid tumors.

Carboxylate or Carboxyl: The group —COO or —COOH. The carboxyl group can form a carboxylic acid. A substituted carboxyl is a —COOR group where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

Chemotherapeutic agent: Any chemical agent with therapeutic usefulness in the treatment of diseases characterized by abnormal cell growth. For example, chemotherapeutic agents are useful for the treatment of neuroblastoma. Particular examples of additional therapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Williams & Wilkins, 2005; Skeel., *Handbook of Cancer Chemotherapy* (6th ed.). Lippincott Williams & Wilkins, 2003). Combination chemotherapy is the administration of more than one agent to treat cancer.

Control: A sample or standard used for comparison with an experimental sample. In some embodiments, the control is a sample obtained from a healthy patient or a non-tumor tissue sample obtained from a patient diagnosed with cancer. In other embodiments, the control is a tumor tissue sample obtained from a patient diagnosed with cancer. In some embodiments, the control is a tumor tissue sample obtained from a patient diagnosed with cancer, where the patient has not received treatment with a G4 stabilizing agent as disclosed herein. In still other embodiments, the control is a historical control or standard reference value or range of values (such as a previously tested control sample, such as a group of cancer patients with known prognosis or outcome, or group of samples that represent baseline or normal values, such as the expression level of the c-MYC gene in a non-tumor tissue).

Cycloalkyl: A non-aromatic carbon-based ring composed of at least three carbon atoms. Examples of cycloalkyl groups include, but are not limited to, cyclopropyl, cyclobutyl, cyclopentyl, cyclohexyl, and the like. A heterocycloalkyl group is a cycloalkyl group as defined above where at least one of the carbon atoms of the ring is substituted with a heteroatom such as, but not limited to, nitrogen, oxygen, sulfur, or phosphorous. Cycloalkyl and heterocycloalkyl groups can be mono-cyclic or bi-cyclic.

Decrease or Reduce: To reduce the quality, amount, or strength of something; for example a reduction in tumor burden. In one example, a therapy reduces a tumor (such as the size of a tumor, the number of tumors, the metastasis of a tumor, or combinations thereof), or one or more symptoms associated with a tumor, for example as compared to the response in the absence of the therapy. In a particular example, a therapy decreases the size of a tumor, the number of tumors, the metastasis of a tumor, or combinations thereof, subsequent to the therapy, such as a decrease of at least 10%, at least 20%, at least 30%, at least 40%, at least 50%, at least 60%, at least 70%, at least 80%, or at least 90%. Such decreases can be measured using the methods disclosed herein.

Determining or detecting the level of expression of a gene product: Detection of a level of expression in either a qualitative or quantitative manner, for example by detecting nucleic acid molecules or proteins, for instance using routine methods known in the art.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Ester: A carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

Halogenated alkyl or Haloalkyl group: An alkyl group with one or more hydrogen atoms present on these groups substituted with a halogen (F, Cl, Br, I).

Hydroxyl: A group represented by the formula —OH.

Hydroxyalkyl: An alkyl group that has at least one hydrogen atom substituted with a hydroxyl group. A alkoxyalkyl group is an alkyl group that has at least one hydrogen atom substituted with an alkoxy group described above.

Isolated or Purified: An biological component is a component that has been substantially separated or purified away from other biological components in the cell of the organism in which the component naturally occurs, i.e., other chromosomal and extra-chromosomal DNA and RNA, proteins, lipids, and organelles. "Isolated" does not require absolute purity. For example, the desired isolated biological component may represent at least 50%, particularly at least about 75%, more particularly at least about 90%, and most particularly at least about 98%, of the total content of the preparation. Isolated biological components as described herein can be isolated by many methods such as salt fractionation, phenol extraction, precipitation with organic solvents (for example, hexadecyltrimethylammonium bromide or ethanol), affinity chromatography, ion-exchange chromatography, hydrophobic chromatography, high performance liquid chromatography, gel filtration, iso-electric focusing, physical separation (e.g., centrifugation or stirring), and the like.

The term purified does not require absolute purity; rather, it is intended as a relative term. Thus, for example, a purified peptide preparation is one in which the peptide or protein is more enriched than the peptide or protein is in its natural environment within a cell. For example, a compound preparation is purified such that the desired polysaccharide protein conjugate represents at least 50%, more particularly at least about 90%, and most particularly at least about 98%, of the total content of the preparation.

Multiple myeloma: A malignancy of terminally differentiated antibody secreting B cells with ~20,000 new cases diagnosed yearly in the United States (Jemal et al., *CA Cancer J Clin.*, 60:277-300, 2010). MM is characterized by the accumulation of clonal plasma cells in the bone marrow (BM) and osteolytic bone lesions. The person of ordinary skill is familiar with tests used to determine the presence and severity of MM. For example, the Durie-Salmon staging system divides MM patients into three stages: Stages I, II, and III, corresponding to low, intermediate, and high cell mass, depending upon the severity of anemia, calcium level, kidney function, presence or absence of bone lesions, and the quantity of abnormal proteins. Approximately 25 percent of people with MM have high-risk disease. Treatment options include chemotherapy, treatment with immune modulating medications, and Autologous Stem Cell Transplant (ASCT) (Attal et al., *N. Engl. J. Med.*, 1996; 335:91-97; Barlogie et al., *Blood*, 1997; 89:789-793). However, patients invariably relapse, and MM remains a universal fatal disease. See, e.g., Rajkumar and Kyle, (eds), *Treatment of Multiple Myeloma and Related Disorders*, 1st; Cambridge University Press, New York, 2006.

c-Myc: A transcription factor known to be overexpressed in several types of cancer, including lymphoma and multiple myeloma. c-Myc protein is encoded by the c-MYC gene. Expression of the c-MYC gene is regulated in part by a 27 base pair (Pu27) sequence found in the nuclease hypersensitive element III(1) region (NHEIII$_1$) of the c-MYC promoter that can form a G-quadruplex (G4) structure. Formation of the G4 structure in this sequence is believed to result in a "kink" in the DNA that prevents the polymerase from continuing along its reading frame, ultimately resulting in downregulation of the c-MYC gene.

N-heterocyclic: Mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

Pharmaceutical composition: A composition including an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

Pharmaceutically acceptable carrier: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired tumor response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Pharmaceutically acceptable salt or ester: Salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like.

Pharmaceutically acceptable salts of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of pharmacologically acceptable salts, see Berge et al., *J. Pharm. Sci.* 66:1 (1977).

Pharmaceutically acceptable esters include those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Phosphoryl: Moieties of the formula —P(O)OR—, wherein R may be H, an aliphatic or aromatic moiety, a cation or a lone pair of electrons. Phosphoryl moieties may be further substituted to form phosphoramidates, phosphates and phosphonates.

Polyether moiety: An oligomer (which is inclusive of dimers and higher repeating units) or a polymer. Illustrative polyether moieties include those derived from an aliphatic polyether (e.g., paraformaldehyde, polyethylene glycol (PEG), polypropylene glycol, and polytetramethylene glycol, and those derived from an aromatic polyether (e.g., polyphenyl ether or poly(p-phenylene oxide)). A preferred polyether moiety is derived from PEG, also referred to herein as a poly(ethylene oxide). The PEG may be a straight chain PEG or a branched PEG. PEG is also inclusive of methoxypolyethylene glycol. In certain embodiments, the number of repeating ethylene oxide units in the PEG moiety may range from 2 to 50, more particularly from 2 to 10. The polyether moiety may be covalently bonded to the core motif via PEGylation procedures.

Small organic molecule: An organic molecule with a molecular weight of about 1000 daltons or less (for example about 900 daltons or less, about 800 daltons or less, about 700 daltons or less, about 600 daltons or less, about 500 daltons or less, about 400 daltons or less, about 300 daltons or less, about 200 daltons or less, or about 100 daltons or less). In some examples, a small organic molecule has a molecular weight of about 100-1000 daltons, about 200-900 daltons, about 300-700 daltons, about 200-500 daltons, or about 400-700 daltons.

Subject: Includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

Substituted or Substitution: Replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

Sulfinyl: The group —S(=O)H. A substituted sulfinyl or sulfoxide is a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

Sulfonyl: The group —$SO_2$H. The sulfonyl group can be further substituted with a variety of groups to form, for example, sulfonic acids, sulfonamides, sulfonate esters and sulfones. A substituted sulfonyl is a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2$Me, —$SO_2$Et and —$SO_2$Pr.

Sulfonylamido or sulfonamide: The group —$SO_2NH_2$.

Thiol: The group —SH. A substituted thiol is a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

Therapeutically effective amount: The amount of an agent that alone, or together with one or more additional agents, induces the desired response, such as, for example treatment of a tumor in a subject. Ideally, a therapeutically effective amount provides a therapeutic effect without causing a substantial cytotoxic effect in the subject.

In one example, a desired response is to decrease the size, volume, or number (such as metastases) of a tumor in a subject. For example, the agent or agents can decrease the size, volume, or number of tumors by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount of a disclosed compound that is administered to a human or veterinary subject will vary depending upon a number of factors associated with that subject, for example the overall health of the subject. A therapeutically effective amount can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

Treating or Inhibiting a Disease: A therapeutic intervention that reduces a sign or symptom of a disease or pathological condition related to a disease (such as a tumor). Treatment can also induce remission or cure of a condition, such as a tumor. In particular examples, treatment includes preventing a tumor, for example by inhibiting the full development of a tumor, such as preventing development of a metastasis or the development of a primary tumor. Prevention does not require a total absence of a tumor.

Reducing a sign or symptom of a disease or pathological condition related to a disease, refers to any observable beneficial effect of the treatment. Reducing a sign or symptom associated with a tumor can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor. A "prophylactic" treatment is a treatment administered to a subject who does not exhibit signs of a disease or exhibits only early signs for the purpose of decreasing the risk of developing pathology.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

An "established" or "existing" tumor is an existing tumor that can be discerned by diagnostic tests. In some embodiments, and established tumor can be palpated. In some embodiments, and "established tumor" is at least 500 $mm^3$, such as at least 600 $mm^3$, at least 700 $mm^3$, or at least 800 $mm^3$ in size. In other embodiments, the tumor is at least 1 cm long. With regard to a solid tumor, and established tumor generally has an robust blood supply, and has induced Tregs and myeloid derviced suppressor cells (MDSC).

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Therefore, comprising "A" or "B" refers to including A, including B, or including both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described herein. In case of conflict, the present specification, including explanations of terms, will control. In addition, the materials, methods, and examples are illustrative only and not intended to be limiting.

II. Compounds

Disclosed therein are novel methods for using G4 stabilizing compounds, or a pharmaceutically acceptable salt or ester thereof, for the treatment of, for example, cancer. The compounds can selectively bind to the G4 in the c-MYC promoter, for example G4 DNA comprising the nucleic acid sequence set forth as TGAGGGTGGGTAGGGTGGGTAA, SEQ ID NO: 2. In several embodiments, the compounds can be used to reduce expression of the c-MYC gene in a cell. The cell can be in vitro or in vivo. In a non-limiting example, the cell is a cancer cell, such as a multiple myeloma cell.

In one embodiment, there is disclosed herein a compound, or a pharmaceutically acceptable salt or ester thereof, having a structure of:

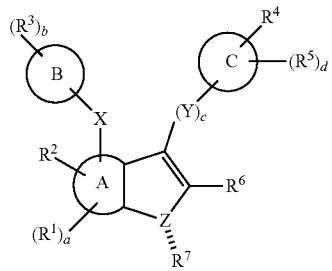

Formula I wherein:

A, B, and C are each independently selected from a 4 to 7 membered cycloaliphatic, optionally-substituted heterocycloaliphatic, optionally-substituted aryl, or optionally-substituted heteroaryl;

each $R^1$ is independently selected from hydrogen or optionally-substituted lower alkyl;

a is 0 to 2, such as 0 to 1, for example 0;

$R^2$ is selected from hydroxyl, halogen, lower haloalkyl, or optionally-substituted lower alkoxy, such as hydroxyl;

X is optionally-substituted methyl, ethyl or propyl, such as methyl;

each $R^3$ is independently selected from hydrogen, halogen, lower haloalkyl, or optionally-substituted lower alkyl, for example, $R^3$ can be methyl and b can be 1;

b is 0 to 6, such as 0 to 1, for example 1;

each Y is independently selected from optionally-substituted lower alkyl, optionally-substituted amide, optionally-substituted sulfonamide, or optionally-substituted phosphoramide;

c is 0 to 3, such as 1 to 2, for example 1;

$R^4$ is selected from halogen, lower haloalkyl, or optionally-substituted lower alkyl, such as lower haloalkyl, for example trifluoromethyl;

each $R^5$ is independently selected from hydrogen, halogen, lower haloalkyl, or optionally-substituted lower alkyl;

d is 0 to 5, such as 0 to 1, for example 0;

$R^6$ is selected from halogen, hydroxyl, lower haloalkyl, or optionally-substituted lower alkyl, such as lower alkyl, for example methyl;

Z is selected from carbon, oxygen, nitrogen, or sulfur, such as oxygen; and wherein if Z is carbon or nitrogen, $R^7$ is selected from hydroxyl, halogen, lower haloalkyl, or optionally-substituted lower alkoxy, or is not present.

In some embodiments of Formula I, X is methyl.

In some embodiments of Formula I, Y is amide. In some embodiments of Formula I, Y can be selected from one of:

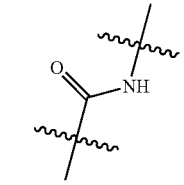 [SMILES: *NC(*)=O]

and c can be selected from 1 or 2, for example, Y can be and c can be 1.

In some embodiments of Formula I, B is optionally-substituted N-heterocyclic or N-heterocyclic. In some embodiments of Formula I, B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine. In some embodiments of Formula I, $R^3$ is hydrogen or methyl. For example, in some embodiments of Formula I, a combination of B and $R^3$ can be selected from one of the following:

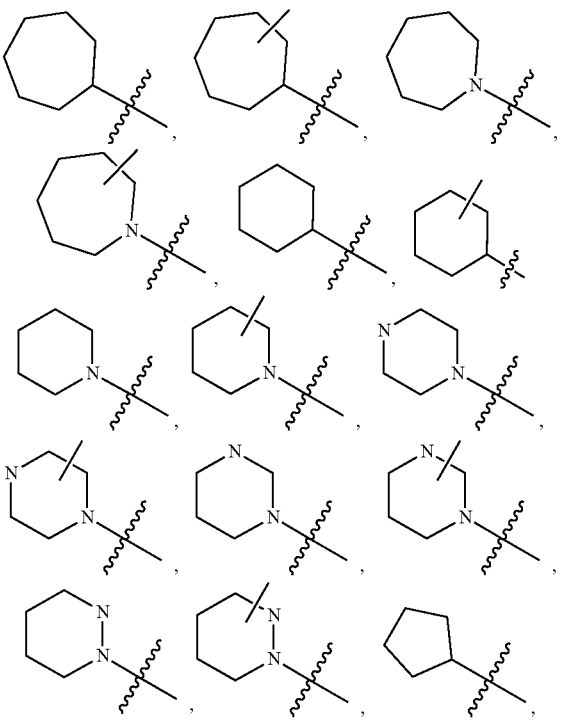

-continued

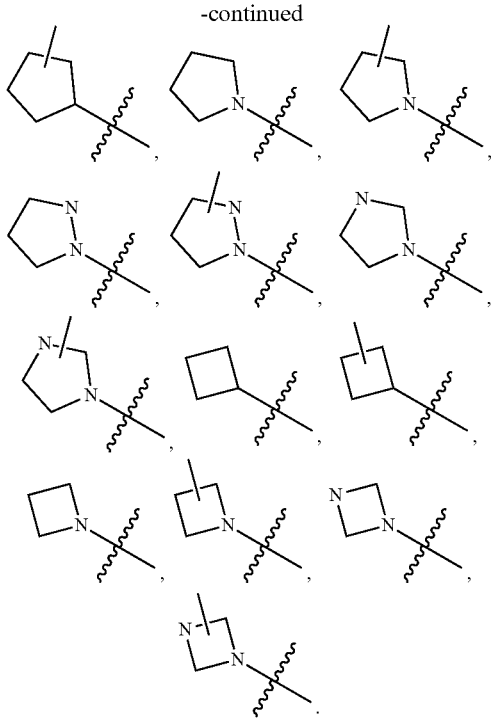

In one embodiment, there is disclosed herein a compound, or a pharmaceutically acceptable salt or ester thereof, having a structure of:

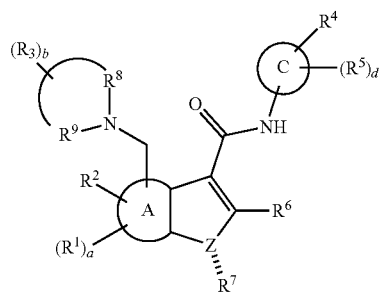

Formula II wherein:

A and C are each independently selected from a 5 or 6 membered optionally-substituted aryl, or optionally-substituted heteroaryl;

each $R^1$ is independently selected from hydrogen or optionally-substituted lower alkyl, such as methyl;

a is 0 to 2, such as 0 to 1, for example 0;

$R^2$ is selected from hydroxyl, halogen, lower haloalkyl, or optionally-substituted lower alkoxy, such as hydroxyl;

$R^8$ and $R^9$ together with the linking nitrogen atom form a 4 to 7 membered optionally-substituted N-heterocyclic ring;

each $R^3$ is independently selected from hydrogen, halogen, lower haloalkyl, or optionally-substituted lower alkyl;

b is 0 to 6;

$R^4$ is selected from halogen, lower haloalkyl, or optionally-substituted lower alkyl;

each $R^5$ is independently selected from hydrogen, halogen, lower haloalkyl, or optionally-substituted lower alkyl;

d is 0 to 5;

$R^6$ is selected from halogen, hydroxyl, lower haloalkyl, or optionally-substituted lower alkyl;

Z is selected from nitrogen or oxygen; and wherein if Z is nitrogen, $R^7$ is selected from hydrogen, hydroxyl, halogen, lower haloalkyl, or optionally-substituted lower alkoxy, and if Z is oxygen, $R^7$ is not present.

In some embodiments of Formula II, A is a 6 membered aryl ring; C is a 6-membered aryl ring; each $R^1$ is independently selected from hydrogen or optionally-substituted lower alkyl; a is 0, 1, or 2; $R^2$ is selected from hydroxyl or halogen; $R^8$ and $R^9$ together with the linking nitrogen atom form a 4 to 7 membered optionally-substituted N-heterocyclic ring; each $R^3$ is independently selected from hydrogen, halogen, lower haloalkyl, or optionally-substituted lower alkyl; b is 0 to 4; $R^4$ is selected from halogen, lower haloalkyl, or optionally-substituted lower alkyl; each $R^5$ is independently selected from hydrogen, halogen, lower haloalkyl, or optionally-substituted lower alkyl; d is 0, 1, or 2; $R^6$ is selected from methyl, trifluoromethyl, or phenyl; Z is selected from nitrogen or oxygen; and if Z is nitrogen, $R^7$ is selected from hydrogen, hydroxyl, halogen, lower haloalkyl, or optionally-substituted lower alkyl, and if Z is oxygen, $R^7$ is not present.

In some embodiments of Formula I or Formula II, C can be 6-membered optionally-substituted aryl or optionally substituted heteroaryl. In some embodiments of Formula I or Formula II, $R^4$ can be lower haloalkyl, such as trifluoromethyl. In some embodiments of Formula I or Formula II, d can be 0. For example, in some embodiments, C can be a benzyl or nitrobenzyl ring, and $R^4$ can be methyl or trifluoromethyl. For example, in some embodiments,

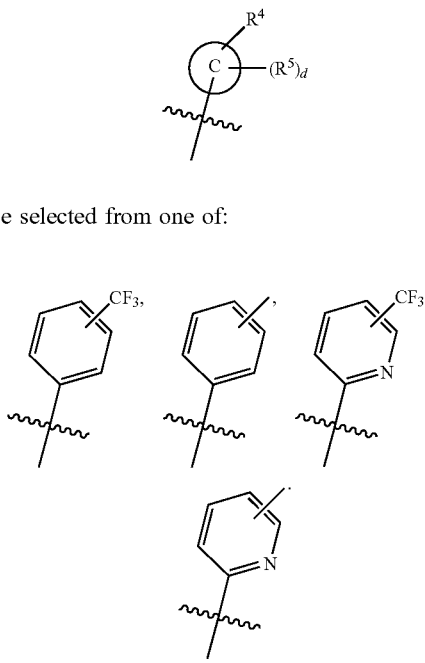

can be selected from one of:

In some embodiments of Formula II, Z is not oxygen, $R^2$ is not hydroxyl, $R^6$ is not methyl, B is not a 5-, 6-, or 7-membered N-heterocycloalkyl ring, and/or the compound does not comprise the structure set forth as any one of structures 1-13, or 17-20.

In some embodiments of Formula I or Formula II, A is a 6-membered optionally-substituted aryl or optionally-substituted heteroaryl. In some embodiments of Formula I or Formula II, each of a is 0. In some embodiments of Formula I or Formula II, $R^2$ is hydroxyl or halide. For example, in some embodiments of Formula I or Formula II,

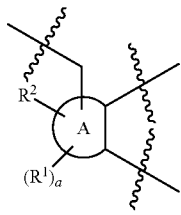

can be selected from one of:

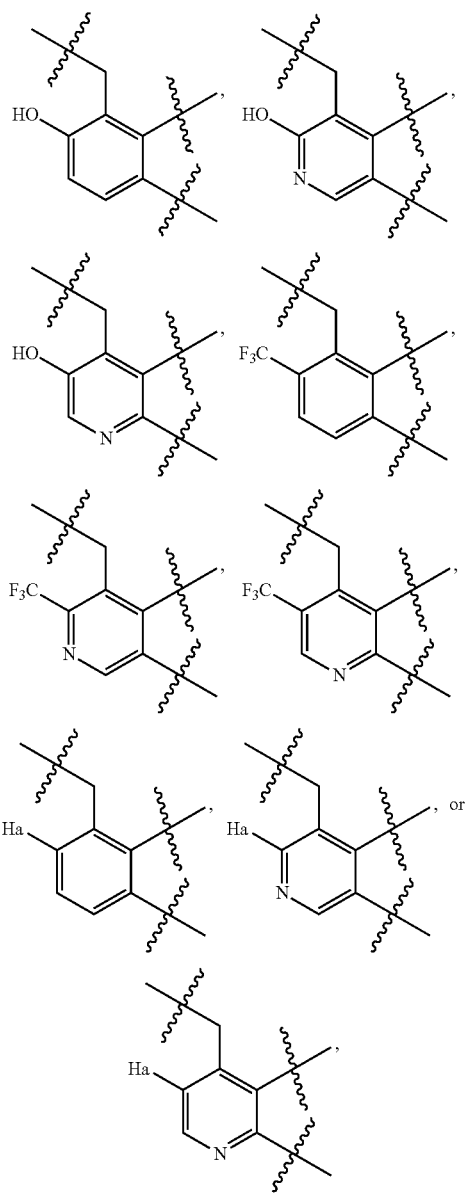

wherein Ha is halide, such as F or Cl.

In some embodiments, there is disclosed herein a compound, or a pharmaceutically acceptable salt or ester thereof, having a structure of any one of Formulas III-IX:

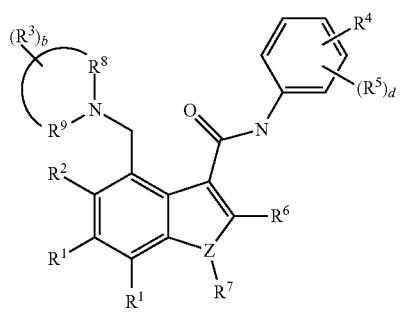

Formula III

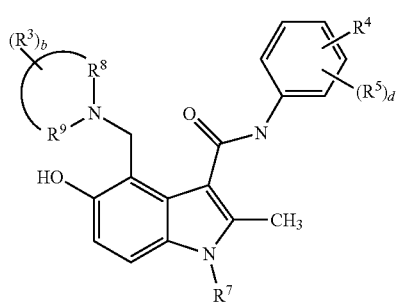

Formula IV

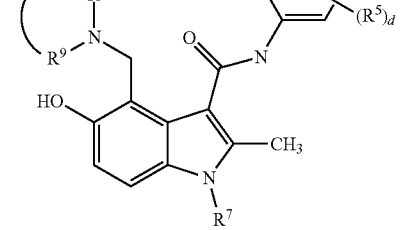

Formula V

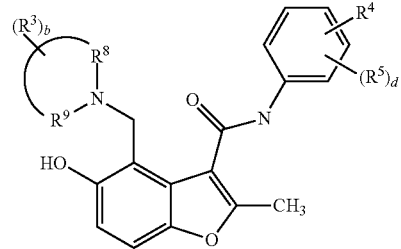

Formula VI

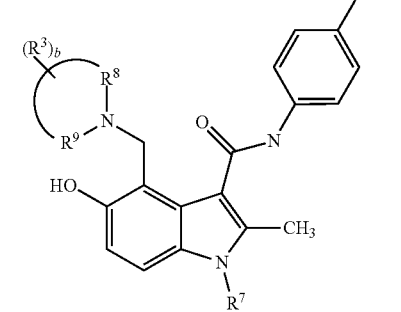

Formula VII

Formula VIII

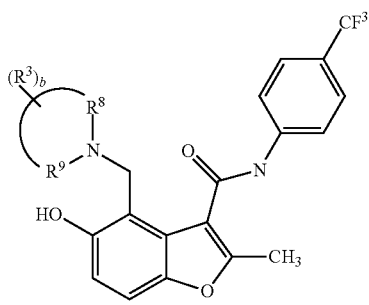

Formula IX

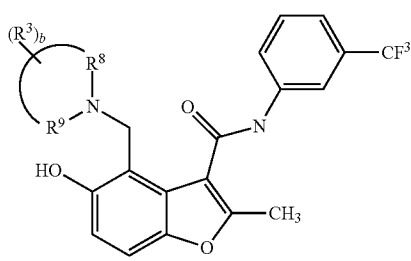

With reference to Formula III, in some embodiments, each $R^1$ is independently selected from hydrogen or optionally-substituted lower alkyl or is not present; $R^2$ is selected from hydroxyl or halogen; $R^8$ and $R^9$ together with the linking nitrogen atom form a 4 to 7 membered optionally-substituted N-heterocyclic ring; each $R^3$ is independently selected from hydrogen, halogen, lower haloalkyl, or optionally-substituted lower alkyl; b is 0 to 6; $R^4$ is selected from halogen, lower haloalkyl, or optionally-substituted lower alkyl; each $R^5$ is independently selected from hydrogen, halogen, lower haloalkyl, or optionally-substituted lower alkyl; d is 0 to 2; and $R^6$ is selected from methyl, trifluoromethyl, or phenyl; Z is selected from nitrogen or oxygen; if Z is nitrogen, $R^7$ is selected from hydrogen, hydroxyl, halogen, lower haloalkyl, or optionally-substituted lower alkyl, and if Z is oxygen, $R^7$ is not present.

With reference to Formula III, in some embodiments, each $R^1$ is independently selected from hydrogen or optionally-substituted lower alkyl; $R^2$ is selected from hydroxyl or halogen; $R^8$ and $R^9$ together with the linking nitrogen atom form a 4 to 7 membered optionally-substituted N-heterocyclic ring; each $R^3$ is independently selected from halogen, lower haloalkyl, or optionally-substituted lower alkyl; b is 0 to 4; $R^4$ is trifluoromethyl; each $R^5$ is independently selected from halogen, lower haloalkyl, or optionally-substituted lower alkyl; d is 0, 1, or 2; $R^6$ is selected from methyl, trifluoromethyl, or phenyl; Z is selected from nitrogen or oxygen; and if Z is nitrogen, $R^7$ is selected from hydrogen, hydroxyl, halogen, lower haloalkyl, or optionally-substituted lower alkyl, and if Z is oxygen, $R^7$ is not present; and with the proviso that the compound does not comprise the structure set forth as any one of structures 12-13, 17-20, or 36-43.

With reference to Formula IV, in some embodiments, $R^8$ and $R^9$ together with the linking nitrogen atom form a 4 to 7 membered optionally-substituted N-heterocyclic ring; each $R^3$ is independently selected from hydrogen, halogen, lower haloalkyl, or optionally-substituted lower alkyl; b is 0 to 6; $R^4$ is selected from halogen, lower haloalkyl, or optionally-substituted lower alkyl; each $R^5$ is independently selected from hydrogen, halogen, lower haloalkyl, or optionally-substituted lower alkyl; d is 0 to 2; and $R^7$ is selected from hydrogen, hydroxyl, halogen, lower haloalkyl, or optionally-substituted lower alkyl.

With reference to Formula V, in some embodiments, $R^8$ and $R^9$ together with the linking nitrogen atom form a 4 to 7 membered optionally-substituted N-heterocyclic ring; each $R^3$ is independently selected from hydrogen, halogen, lower haloalkyl, or optionally-substituted lower alkyl; b is 0 to 6; $R^4$ is selected from halogen, lower haloalkyl, or optionally-substituted lower alkyl; each $R^5$ is independently selected from hydrogen, halogen, lower haloalkyl, or optionally-substituted lower alkyl; and d is 0 to 2.

With reference to Formulas VI and VII, in some embodiments, $R^8$ and $R^9$ together with the linking nitrogen atom form a 4 to 7 membered optionally-substituted N-heterocyclic ring; each $R^3$ is independently selected from hydrogen, halogen, lower haloalkyl, or optionally-substituted lower alkyl; b is 0 to 6; and $R^7$ is selected from hydrogen, hydroxyl, halogen, lower haloalkyl, or optionally-substituted lower alkyl.

With reference to Formulas VIII and IX, in some embodiments, $R^8$ and $R^9$ together with the linking nitrogen atom form a 4 to 7 membered optionally-substituted N-heterocyclic ring; each $R^3$ is independently selected from hydrogen, halogen, lower haloalkyl, or optionally-substituted lower alkyl; and b is 0 to 6.

In some embodiments of any one of Formulas I-V, $R^4$ is trifluoromethyl and d is 0. In some embodiments of any one of Formulas I-V, $R^4$ is trifluoromethyl and d is 1. In some embodiments of any one of Formulas I-V, $R^4$ is methyl and d is 0. In some embodiments of any one of Formulas II-V, $R^4$ is methyl and d is 1. In some embodiments of any one of Formulas II-IX, the compound does not comprise the structure set forth as any one of structures 12-13, 17-20, or 36-43.

In some embodiments of any one of Formulas II-IX, $R^8$ and $R^9$ together with the linking nitrogen atom form optionally-substituted pyrrolidine, optionally-substituted imidizolidine, optionally-substituted pryazolidine, optionally-substituted piperidine, optionally-substituted piperazine, optionally-substituted azepane. In some embodiments of any one of Formulas II-IX, $R^3$ is hydrogen or methyl. In some embodiments of any one of Formulas II-IX,

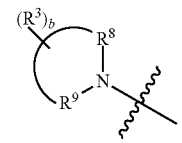

can be selected from one of:

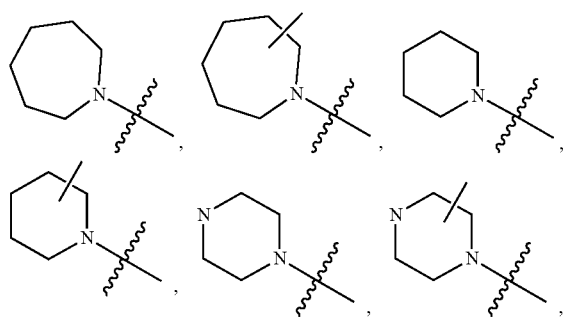

-continued

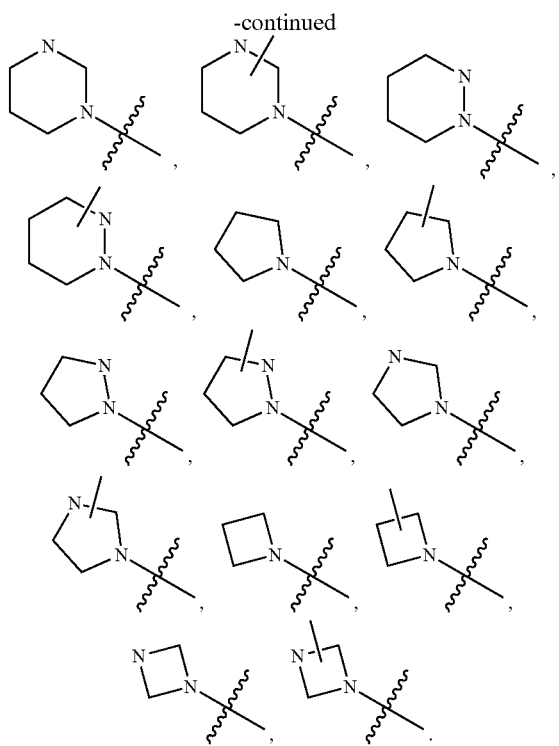

In some embodiments of any one of Formulas II-IX, $R^3$ is hydrogen or methyl. For example, in some embodiments of any one of Formulas II-IX,

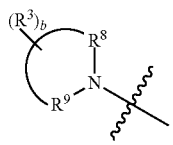

can be selected from one of:

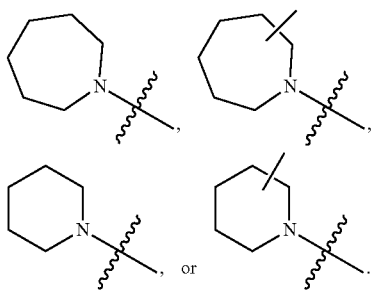

In some embodiments of Formula I, Formula II, or Formula III, $R^6$ is methyl. In some embodiments of Formula I, Formula II, or Formula III, Z is nitrogen.

In some embodiments, of Formula I or Formula II, the compound can be selected from one of compounds 1, 3, 6, 7, 12, 13, or 17-25.

In several embodiments, the disclosed compounds can selectively bind to the G4 in the c-MYC promoter, for example G4 DNA comprising the nucleic acid sequence set forth as TGAGGGTGGGTAGGGTGGGTAA, SEQ ID NO: 2. In certain embodiments, the compounds disclosed herein have an equilibrium dissociation constant ($K_d$) for G4 DNA having the sequence set forth as SEQ ID NO: 2 of no more than 5 μM, such as no more than 1 μM, no more than 0.5 μM, no more than 100 nM, no more than 10 nM, or no more than 1 nM or less.

III. Methods of Use

In several embodiments, a method is provided for reducing c-Myc expression in a cell. The method includes contacting the cell with an effective amount of a disclosed compound (such as any of the compounds disclosed in section II, or one of Compounds 36-43) or a pharmaceutically acceptable salt or ester thereof. The compound selectively binds to G4 quadruplex DNA in the promoter of the c-MYC gene, and stabilizes the G4 formation, thereby reducing expression of the c-MYC gene in the cell. The cell can be in vitro or in vivo. In several embodiments, the expression of the c-MYC gene in the cell is reduced at least 50% (such as at least 75%, at least 80%, at least 90%, at least 95%, or at least 98%) compared to the expression of the c-MYC gene in a corresponding control cell. In some embodiments, decreasing expression of c-Myc in the cell decreases growth and/or proliferation of the cell.

In additional embodiments, a therapeutically effective amount of a disclosed compound (such as any of the compounds disclosed in section II, or one of Compounds 36-43) or a pharmaceutically acceptable salt or ester thereof can be administered to a subject to treat or inhibit a tumor and/or a cancer in a subject. The subject can be selected for treatment that has, is suspected of having or is at risk of developing a tumor, such as a lymphoma or multiple myeloma. Subjects that can benefit from the disclosed methods include human and veterinary subjects. In some embodiments, treating the tumor and/or cancer in the subject decreases growth and/or proliferation of the tumor.

The tumor can be benign or malignant. The tumor can be any tumor of interest, including, but not limited to lymphoma or multiple myeloma. Additional examples are skin tumors, breast tumors, brain tumors, cervical carcinomas, testicular carcinomas, head and neck tumors, gastrointestinal tract tumors, genitourinary system tumors, gynaecological system tumors, breast, endocrine system tumors, skin tumors, a sarcoma of the soft tissue and bone, a mesothelioma, a melanoma, a neoplasm of the central nervous system, or a leukemia. In some embodiments, the tumor is a head and neck tumor, such as tumors of the nasal cavity, paranasal sinuses, nasopharynx, oral cavity, oropharynx, larynx, hypopharynx, salivary glands and paragangliomas. In other embodiments, the tumor is a lung tumor, such as a non-small cell lung cancer or a small cell lung cancer. In further embodiments, the tumor can be a tumor of the gastrointestinal tract, such as cancer of the oesophagus, stomach, pancreas, liver, biliary tree, small intestine, colon, rectum and anal region. In yet other embodiments, the tumor can be a tumor of the genitourinary system, such as cancer of the kidney, urethra, bladder, prostate, urethra, penis and testis. In some embodiments, the tumor is a gynecologic tumor, such as cancer of the cervix, vagina, vulva, uterine body, gestational trophoblastic diseases, ovarian, fallopian tube, peritoneal, or breast. In other embodiments, the tumor is an endocrine system tumor, such as a thyroid tumor, parathyroid tumor, adrenal cortex tumor, pancreatic endocrine tumor, carcinoid tumor and carcinoid syndrome. The tumor can be a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma. The tumor can be a lymphoma, comprising non-Hodgkin's lymphomas, cutaneous T-cell lymphomas, primary central nervous system lymphoma, and Hodgkin's disease. The tumor can be a leukaemia, such as acute leukemias, chronic myelogenous and lymphocytic leukemias. The tumor can be plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites.

Treatment of the tumor is generally initiated after the diagnosis of the tumor, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, treatment is administered to these subjects with a benign tumor that can convert into a malignant or even metastatic tumor.

Treatment initiated after the development of a condition, such as malignant cancer, may result in decreasing the severity of the symptoms of one of the conditions, or completely removing the symptoms, or reducing metastasis, tumor volume or number of tumors. In some example, the tumor becomes undetectable following treatment. In one aspect of the disclosure, the formation of tumors, such as metastasis, is delayed, prevented or decreased. In another aspect, the size of the primary tumor is decreased. In a further aspect, a symptom of the tumor is decreased. In yet another aspect, tumor volume is decreased.

Subjects can be screened prior to initiating the disclosed therapies, for example to determine whether the subject has a tumor. The presence of a tumor can be determined by methods known in the art, and typically include cytological and morphological evaluation. The tumor can be an established tumor. The cells can be in vivo or ex vivo, including cells obtained from a biopsy. The presence of a tumor indicates that the tumor can be treated using the methods provided herein. In some embodiments, a subject with a c-Myc-positive tumor is selected for treatment, for example, by detecting c-Myc expression and/or activity in a biological sample obtained from the subject. For example, upregulated expression of the c-MYC gene (for example, as detected by an increase in c-Myc mRNA, c-Myc protein, or the expression of genes up-regulated by c-Myc compared to a control) can be detected, and in some examples quantified. The c-MYC gene expression in the biological sample is compared to a control (such as a normal, non-tumor sample). An increase in the expression of the c-MYC gene (such as an increase in c-Myc mRNA, c-Myc protein, or the expression of genes up-regulated by c-Myc) in the biological sample relative to the control indicates the presence of a c-Myc-positive tumor, and can be used to select a subject for treatment with one or more of the compounds or compositions disclosed herein. For example, an increase in the test sample of at least 50%, at least 75%, at least 80%, at least 90%, at least 100%, at least 200% or even greater than 500%, relative to the control, indicates the subject (such as a human subject) is likely to respond favorably to treatment with one or more of the agents disclosed herein. Suitable methods for detecting and/or monitoring a c-Myc-positive tumor in a subject (such as a c-Myc-positive multiple myeloma) can be selected by a treating physician. In one embodiment, a sample is obtained from a subject, and the presence of a cell that expresses c-Myc is assessed in vitro.

A therapeutically effective amount of a disclosed compound (such as any of the compounds disclosed in section II, or one of Compounds 36-43) or composition containing same can be administered to a subject to treat a tumor and/or cancer in the subject. The subject can be selected for treatment that has, is suspected of having or is at risk of developing a tumor or tumors, such as multiple myeloma or lymphoma. Subjects that can benefit from the disclosed methods include, for example, human and veterinary subjects.

The administration of a compound (such as any of the compounds disclosed in section II, or one of Compounds 36-43) of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

In some examples, a disclosed compound (such as any of the compounds disclosed in section II, or one of Compounds 36-43) or composition containing same can be administered to a subject to slow or inhibit the growth or metastasis of a tumor and/or cancer. In these applications, a therapeutically effective amount of a disclosed compound (such as any of the compounds disclosed in section II, or one of Compounds 36-43) or composition containing same can be administered to a subject in an amount and under conditions sufficient to bind to the G4 present in the c-MYC promoter and reduce c-Myc expression, thereby slowing or inhibiting the growth or the metastasis of a tumor, or to inhibit a sign or a symptom of a tumor. Examples of suitable subjects include those diagnosed with or suspecting of having cancer (for example, a subject having a tumor), for example a subject having a multiple myeloma.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to inhibit tumor growth, or the amount that is effective at reducing a sign or a symptom of the tumor. The therapeutically effective amount of the agents administered can vary depending upon the desired effects and the subject to be treated. In some examples, therapeutic amounts are amounts which eliminate or reduce the patient's tumor burden, or which prevent or reduce the proliferation of metastatic cells.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

In some embodiments, local administration of the disclosed compounds can be used, for instance by applying a disclosed compound to a region of tissue from which a tumor has been removed, or a region suspected of being prone to tumor development. In some embodiments, sustained intra-tumoral (or near-tumoral) release of the pharmaceutical preparation that includes a therapeutically effective amount of a disclosed compound may be beneficial.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

In particular examples, the subject is administered a therapeutic composition that includes one or more of the disclosed compounds on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with administration of a disclosed compound or composition containing same. Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

Non-limiting examples of additional therapeutic agents that can be used with the combination therapy include microtubule binding agents, DNA intercalators or crosslinkers, DNA synthesis inhibitors, DNA and RNA transcription inhibitors, antibodies, enzymes, enzyme inhibitors, gene regulators, angiogenesis inhibitors, and proteosome inhibitors (such as bortezomib or carfilzomib). These agents (which are administered at a therapeutically effective amount) and treatments can be used alone or in combination. For example, any suitable anti-cancer or anti-angiogenic agent can be administered in combination with the antibodies, conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

IV. Compositions

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

Exemplary Embodiments

Clause 1. A method of decreasing c-Myc expression in a cell, comprising contacting the cell with an effective amount of a compound, or a pharmaceutically acceptable salt or ester thereof, having a structure of:

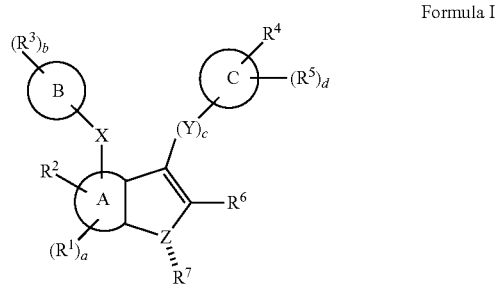

Formula I wherein A, B, and C are each independently selected from a 4 to 7 membered cycloaliphatic, optionally-substituted heterocycloaliphatic, optionally-substituted aryl, or optionally-substituted heteroaryl; each $R^1$ is independently selected from optionally-substituted lower alkyl; a is 0 to 2; $R^2$ is selected from hydroxyl, halogen, lower haloalkyl, or optionally-substituted lower alkoxy; X is optionally-substituted methyl, ethyl or propyl; each $R^3$ is independently selected from halogen, lower haloalkyl, or optionally-substituted lower alkyl; b is 0 to 6; each Y is independently selected from optionally-substituted lower alkyl, optionally-substituted amide, optionally-substituted sulfonamide, or optionally-substituted phosphoramide; c is 0 to 3; $R^4$ is selected from halogen, lower haloalkyl, or optionally-substituted lower alkyl; each $R^5$ is independently selected from halogen, lower haloalkyl, or optionally-substituted lower alkyl; d is 0 to 5; $R^6$ is selected from halogen, hydroxyl, lower haloalkyl, or optionally-substituted lower alkyl; Z is selected from carbon, oxygen, nitrogen, or sulfur; and wherein if Z is carbon or nitrogen, $R^7$ is selected from hydroxyl, halogen, lower haloalkyl, or optionally-substituted lower alkoxy.

Clause 2. The method of clause 1, wherein A is a 6-membered optionally-substituted aryl or optionally-substituted heteroaryl.

Clause 3. The method of clause 1 or clause 2, wherein X is methyl.

Clause 4. The method of any one of the prior clauses, wherein B is optionally-substituted N-heterocyclic or N-heterocyclic.

Clause 5. The method of any one of the prior clauses, wherein B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine.

Clause 6. The method of any one of the prior clauses, wherein Y is amide.

Clause 7. The method of any one of the prior clauses, wherein C is 6-membered optionally-substituted aryl or optionally substituted heteroaryl.

Clause 8. The method of clause 1, wherein the compound has a structure of:

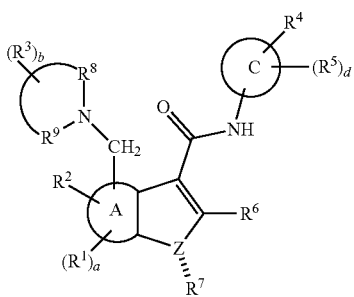

Formula II wherein A and C are each independently selected from a 5 or 6 membered optionally-substituted aryl, or optionally-substituted heteroaryl; each $R^1$ is independently selected from optionally-substituted lower alkyl; a is 0 to 2; $R^2$ is selected from hydroxyl, halogen, lower haloalkyl, or optionally-substituted lower alkoxy; $R^8$ and $R^9$ together with the linking nitrogen atom form a 4 to 7 membered optionally-substituted N-heterocycloaliphatic ring; each $R^3$ is independently selected from halogen, lower haloalkyl, or optionally-substituted lower alkyl; b is 0 to 6; $R^4$ is selected from halogen, lower haloalkyl, or optionally-substituted lower alkyl; each $R^5$ is independently selected from halogen, lower haloalkyl, or optionally-substituted lower alkyl; d is 0 to 5; $R^6$ is selected from halogen, hydroxyl, lower haloalkyl, or optionally-substituted lower alkyl; Z is selected from nitrogen or oxygen; and wherein if Z is carbon or nitrogen, $R^7$ is selected from hydroxyl, halogen, lower haloalkyl, or optionally-substituted lower alkoxy, or is not present.

Clause 9. The method of clause 8, wherein $R^8$ and $R^9$ together with the linking nitrogen atom form optionally-substituted pyrrolidine, optionally-substituted imidizolidine, optionally-substituted pryazolidine, optionally-substituted piperidine, optionally-substituted piperazine, optionally-substituted azepane.

Clause 10. The method of any one of the prior clauses, wherein a is 0.

Clause 11. The method of any one of the prior clauses, wherein $R^2$ is hydroxyl.

Clause 12. The method of any one of the prior clauses, wherein $R^3$ methyl and b is 1.

Clause 13. The method of any one of the prior clauses, wherein $R^4$ is lower haloalkyl.

Clause 14. The method of clause 13, wherein $R^4$ is trifluoromethyl.

Clause 15. The method of any one of the prior clauses, wherein d is 0.

Clause 16. The method of any one of the prior clauses, wherein $R^6$ is methyl.

Clause 17. The method of any one of the prior clauses, wherein Z is nitrogen.

Clause 18. The method of clause 1, wherein the compound is one of compounds 1, 3, 6, 7, 12, 13, or 17-25.

Clause 19. The method of any one of the prior clauses, wherein the cell is in vitro.

Clause 20. The method of any one of clauses 1-18, wherein the cell is in vivo.

Clause 21. The method of any one of the prior clauses, wherein contacting the cell with the effective amount of the compound or the pharmaceutically acceptable salt or ester thereof decreases c-Myc expression in the cell by at least 50% compared to a control.

Clause 22. The method of any one of the prior clauses, wherein decreasing expression of c-Myc in the cell decreases growth and/or proliferation of the cell.

Clause 23. The method of any one of the prior clauses, wherein the cell is a cell with overexpression of the c-MYC gene.

Clause 24. The method of any one of the prior clauses, wherein the compound selectively binds to a G4 quadruplex nucleic acid molecule comprising the sequence set forth as SEQ ID NO: 2 with a $K_d$ of no more than 5 μM.

Clause 25. The method of any one of clauses 1-18 or 20-22, wherein the cell is a tumor cell in the subject, the method further comprising treating or preventing a tumor in the subject, comprising the step of:

administering to a subject in need thereof a therapeutically effective amount of the compound, or the pharmaceutically acceptable salt or ester thereof, to decrease c-Myc expression in the tumor cell, thereby treating or preventing the tumor in the subject.

Clause 26. The method of clause 23, wherein the tumor is a lymphoma or multiple myeloma.

Clause 27. The method of clauses 25 or clause 26, wherein treating the tumor comprises decreasing tumor volume; decreasing the number or size of metastases; or lessening a symptom of the tumor.

Clause 28. The method of any of clauses 25-27, further comprising administering a therapeutically effective amount of an additional anti-cancer agent to the subject, particularly wherein the additional anti-cancer agent is a proteasome inhibitor, for example bortezomib or carfilzomib.

Clause 29. A compound, or a pharmaceutically acceptable salt or ester thereof, having a structure of:

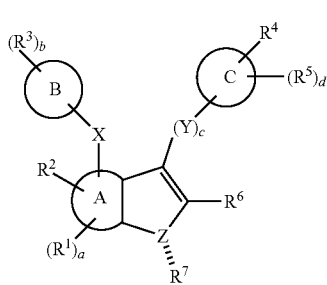

Formula I wherein A, B, and C are each independently selected from a 4 to 7 membered cycloaliphatic, optionally-substituted heterocycloaliphatic, optionally-substituted aryl, or optionally-substituted heteroaryl; each $R^1$ is independently selected from optionally-substituted lower alkyl; a is 0 to 2; $R^2$ is selected from hydroxyl, halogen, lower haloalkyl, or optionally-substituted lower alkoxy; X is optionally-substituted methyl, ethyl or propyl; each $R^3$ is independently selected from halogen, lower haloalkyl, or optionally-substituted lower alkyl; b is 0 to 6; each Y is independently selected from optionally-substituted lower alkyl, optionally-substituted amide, optionally-substituted sulfonamide, or optionally-substituted phosphoramide; c is 0 to 3; $R^4$ is selected from halogen, lower haloalkyl, or optionally-substituted lower alkyl; each $R^5$ is independently selected from halogen, lower haloalkyl, or optionally-substituted lower alkyl; d is 0 to 5; $R^6$ is selected from halogen, hydroxyl, lower haloalkyl, or optionally-substituted lower alkyl; Z is selected from carbon, oxygen, nitrogen, or sulfur; and wherein if Z is carbon or nitrogen, $R^7$ is selected from halogen, lower haloalkyl, or optionally-substituted lower alkoxy or is not present; and with the proviso selected from one or more of: Z is not oxygen; Y is not amide; X is not $CH_2$; c is not 1; $R^2$ is not hydroxyl; $R^6$ is not methyl; B is not a 5-, 6-, or 7-membered N-heterocycloalkyl ring; and the compound does not comprise the structure set forth as any one of structures 1-13, or 17-20.

Clause 30. The compound of clause 29, wherein A is a 6-membered optionally-substituted aryl or optionally-substituted heteroaryl.

Clause 31. The compound of clause 29 or clause 30, wherein X is methyl.

Clause 32. The compound of any one of clauses 29-31, wherein B is optionally-substituted N-heterocyclic or N-heterocyclic.

Clause 33. The compound of any one of clauses 29-32, wherein B is selected from optionally-substituted pyrrolidine, optionally-substituted imidizolidine, optionally-substituted pryazolidine, optionally-substituted pyrrole, optionally-substituted diazole, optionally-substituted triazole, optionally-substituted piperidine, optionally-substituted pyridine, optionally-substituted diazine, optionally substituted triazine, optionally-substituted piperazine, optionally-substituted azepane, or optionally-substituted azepine.

Clause 34. The compound of any one of clauses 29-33, wherein Y is amide.

Clause 35. The compound of any one of clauses 29-34, wherein C is 6-membered optionally-substituted aryl or optionally substituted heteroaryl.

36. The compound of clause 28, wherein the compound has a structure of:

Formula II wherein A and C are each independently selected from a 5 or 6 membered optionally-substituted aryl, or optionally-substituted heteroaryl; each $R^1$ is independently selected from hydrogen or optionally-substituted lower alkyl; a is 0 to 2; $R^2$ is selected from hydroxyl, halogen, lower haloalkyl, or optionally-substituted lower alkoxy; $R^8$ and $R^9$ together with the linking nitrogen atom form a 4 to 7 membered optionally-substituted N-heterocycloaliphatic ring; each $R^3$ is independently selected from hydrogen, halogen, lower haloalkyl, or optionally-substituted lower alkyl; b is 0 to 6; $R^4$ is selected from halogen, lower haloalkyl, or optionally-substituted lower alkyl; each $R^5$ is independently selected from hydrogen, halogen, lower haloalkyl, or optionally-substituted lower alkyl; d is 0 to 5; $R^6$ is selected from hydrogen, halogen, hydroxyl, lower haloalkyl, or optionally-substituted lower alkyl; Z is selected from nitrogen or oxygen; and wherein if Z is carbon or nitrogen, $R^7$ is selected from hydroxyl, halogen, lower haloalkyl, or optionally-substituted lower alkoxy, or is not present.

Clause 37. The compound of clause 36, wherein $R^8$ and $R^9$ together with the linking nitrogen atom form optionally-substituted pyrrolidine, optionally-substituted imidizolidine, optionally-substituted pryazolidine, optionally-substituted piperidine, optionally-substituted piperazine, optionally-substituted azepane.

Clause 38. The compound of any one of clauses 29-37, wherein each of $R^1$ is hydrogen.

Clause 39. The compound of any one of clauses 29-38, wherein $R^2$ is hydroxyl.

Clause 40. The compound of any one of clauses 29-39, wherein $R^3$ is hydrogen or methyl.

Clause 41. The compound of any one of clauses 29-40, wherein $R^4$ is lower haloalkyl.

Clause 42. The compound of clause 41, wherein $R^4$ is trifluoromethyl.

Clause 43. The compound of any one of clauses 29-41, wherein each of $R^5$ is hydrogen.

Clause 44. The compound of any one of clauses 29-43, wherein $R^6$ is methyl.

Clause 45. The compound of any one of clauses 29-44, wherein Z is nitrogen.

Clause 46. The compound of clause 29, wherein the compound is one of compounds 21-25.

Clause 47. A pharmaceutical composition comprising a compound of any one of clauses 29-46, and at least one pharmaceutically acceptable additive.

Clause 48. The pharmaceutical composition of clause 47, comprising a unit dosage form of a therapeutic amount of the compound.

Clause 49. The pharmaceutical composition of clause 47 or clause 48, further comprising an additional anticancer agent, particularly wherein the anticancer agent is a proteasome inhibitor, for example bortezomib or carfilzomib.

EXAMPLES

The following examples are provided to illustrate particular features of certain embodiments, but the scope of the claims should not be limited to those features exemplified.

Example 1

Selective Inhibition of c-Myc Expression Via Small Molecule Stabilization of G-Quadruplex DNA The transcription factor c-Myc plays a pivotal role in cancer initiation and progression, however small molecules that selectively suppress its function or expression are limiting. One potential route to pharmacological inhibition of c-Myc is preventing its expression through small molecule mediated stabilization of the G-quadruplex (G4) present in its promoter. Here, a small molecule that binds to quadruplex DNA, and inhibits c-Myc expression in cell models is reported. A small molecule microarray screen was used to identify compounds that both directly and selectively bind to the c-MYC G4. Surface plasmon resonance (SPR) and thermal melt assays confirmed that one molecule identified in this screen binds reversibly to the G4 with single digit micromolar affinity. Furthermore, evaluation of this compound in biochemical and cell-based assays demonstrates that the compound effectively silences c-Myc transcription and translation via a quadruplex-dependent mechanism of action. Consistent with other studies of c-Myc inhibition, the compound induces G1 arrest and is selectively toxic to c-Myc-driven cancer cell lines that contain a quadruplex in the promoter, with minimal effects on peripheral blood mononucleocytes or a cell line lacking the G4. Gene expression analysis demonstrates that c-Myc and a number of c-Myc target genes are downregulated upon treatment with this compound, while several other known quadruplex-driven genes are not affected. This work confirms that selective stabilization of the c-MYC G4 is a viable strategy for attenuating c-Myc expression and function.

Figure 1B:
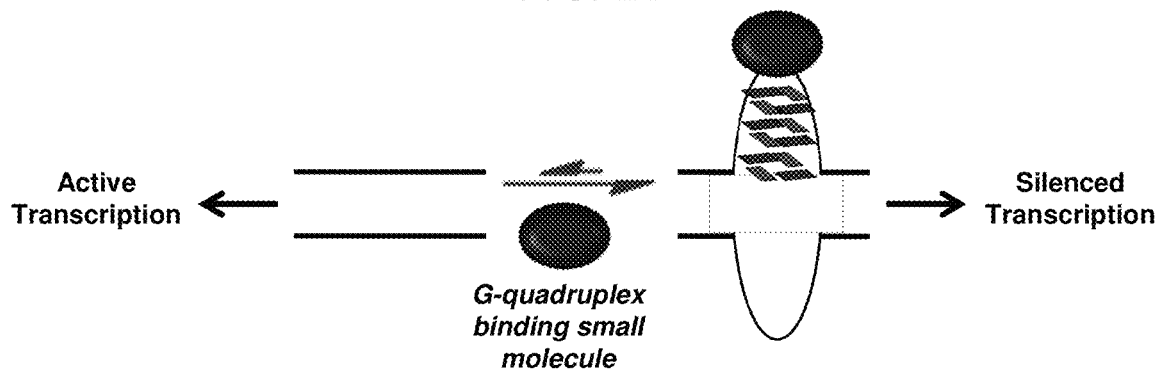

The oncogenic transcription factor c-Myc has a pleiotropic role in a wide range of cell processes (Bretones, et al., *Biochimica et biophysica acta* 2014) and is deregulated in some 70% of human cancers (Beroukhim, et al., *Nature* 2010, 463, 899). However, targeting the c-Myc protein directly has proven to be difficult due to a lack of well-defined pockets amenable to small molecule binding (Berg, et al., *Proc Natl Acad Sci USA* 2002, 99, 3830; Yin, et al., *Oncogene* 2003, 22, 6151; Huang, et al., *Experimental hematology* 2006, 34, 1480; Wang, et al., *Mol Cancer Ther* 2007, 6, 2399) and alternative mechanisms to inhibit c-Myc function are desirable (Dang, et al., *Seminars in cancer biology* 2006, 16, 253; Balasubramanian, et al., *Nat Rev Drug Discov* 2011, 10, 261). One such alternative mechanism is through stabilization of the G-quadruplex (G4) present in the c-MYC promoter region (Balasubramanian, et al., *Nat Rev Drug Discov* 2011, 10, 261). G4s are guanine-rich noncanonical Hoogsteen-bonded nucleotide structures found in many RNA and DNA sequences (FIG. 1A) (Huppert and Balasubramanian, *Nucleic Acids Res* 2007, 35, 406; Gray, et al., *Nat Chem Biol* 2014, 10, 313). For example, expression of the proto-oncogene c-MYC is regulated by a 27 base pair (Pu27) sequence found in the nuclease hypersensitive element III(1) region (NHEIII$_1$) of the c-MYC gene known to form a G4 (Gonzalez and Hurley, *Annual review of pharmacology and toxicology* 2010, 50, 111). Formation of the quadruplex in this sequence is believed to result in a "kink" in the DNA that prevents the polymerase from continuing along its reading frame, ultimately resulting in downregulation of the associated gene (FIG. 1B) (Weitzmann, et al., *J Biol Chem* 1996, 271, 20958). The use of small molecules to stabilize the G4 conformation and consequently decrease c-Myc expression is an attractive therapeutic goal in cancers where c-Myc is overexpressed (Siddiqui-Jain, et al., *Proc Natl Acad Sci USA* 2002, 99, 11593).

There are a number of reported ligands that effectively stabilize quadruplex DNA according to structural and biophysical measurements (Dash, et al., *Chemistry* 2011, 17, 4571), however few are validated in cellular models (Castillo-Gonzalez, et al., *Curr Pharm Des* 2013, 19, 2164; Wei, et al., *International journal of biological macromolecules* 2013, 57, 1). Additionally, though some quadruplex ligands silence c-MYC expression in cells, they may not be selective (Nasiri, et al., *Chem Commun* (Camb) 2014, 50, 1704) and activity cannot always be attributed to a c-MYC quadruplex-dependent mechanism of action (Boddupally, et al., *J Med Chem* 2012, 55, 6076). The only G4-stabilizing drug that has advanced to clinical trials is Quarfloxin (CX-3552, Cylene Pharmaceuticals, Tetragene). Quarfloxin effects apoptosis and cell death in cancer cells, and its mechanism of action is believed to involve the inhibition of ribosomal RNA biogenesis via disruption of the interaction between nucleolin and G4s in ribosomal DNA (Drygin, et al., *Cancer Res* 2009, 69, 7653). Furthermore, many other reported G4 ligands are duplex DNA intercalators, exhibit promiscuous reactivity, or bind to quadruplexes with greater than a 1:1 binding stoichiometry (Balasubramanian, et al., *Nat Rev Drug Discov* 2011, 10, 261; Drygin, et al., *Cancer Res* 2009, 69, 7653; Dai, et al., *J Am Chem Soc* 2011, 133, 17673). As an example, TMPyP4, a commonly used reagent in quadruplex binding studies, is a cationic porphyrin that binds to quadruplex DNA in multiple fashions (Freyer, et al., *Biophys J* 2007, 92, 2007), and also has significant off-target activity (Sibata, et al., *Expert opinion on pharmacotherapy* 2001, 2, 917; Grand, C. L.; et al., *Mol Cancer Ther* 2002, 1, 565; Mikami-Terao, et al., *Cancer Lett* 2008, 261, 226). A second prominent example is pyridostatin, a compound designed to bind all G4s in the cell (Koirala, et al., *Nat Chem* 2011, 3, 782; Muller, et al., *Org Biomol Chem* 2012, 10, 6537. Thus, new classes of potent, selective quadruplex ligands that are active in tissue culture models would be of substantial utility as reagents to study c-Myc biology as well as potential therapeutics.

The identification and characterization of a new class of small molecule c-MYC G4 ligands using small molecule microarrays (SMMs) is provided in this example. A SMM screen of 20,000 compounds using a fluorescently tagged G4 DNA oligonucleotide derived from the NHEIII$_1$ region in the c-MYC promoter was performed (Gonzalez and Hurley, *Annual review of pharmacology and toxicology* 2010, 50, 111). One of the small molecules identified in this screen inhibits c-MYC transcription in vitro in a G4-dependent fashion. Direct and reversible binding to c-MYC G4-DNA was validated through SPR and thermal melt assays. Furthermore, decreased c-Myc transcription correlated with decreased viability across a panel of multiple myeloma cell lines. Additionally, the compound has minimal effects on cell viability in a Burkitt's Lymphoma cell line harboring a c-MYC translocation that deletes the G4, and has only modest toxicity in normal peripheral blood mononucleocytes. Finally, gene expression analysis demonstrates that the compound reduces the expression of c-MYC and c-Myc target genes, and does not alter the expression of several other genes known to be controlled by G4s, thus indicating considerable selectivity.

Results and Discussion

Figure 2A:
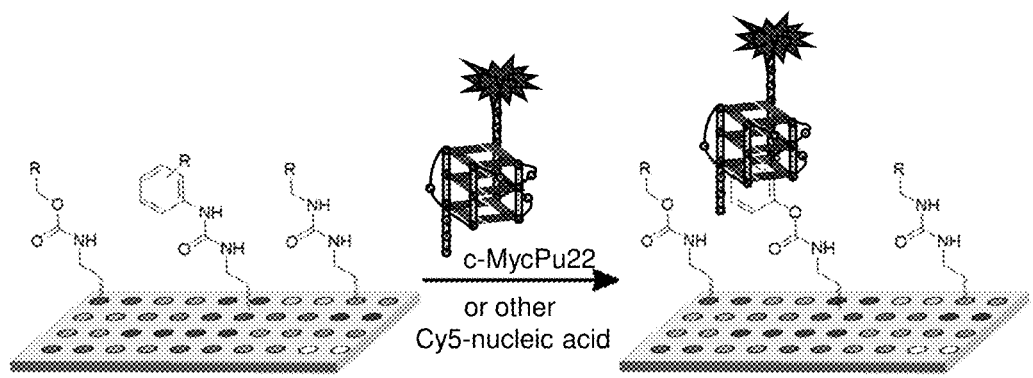
FIGS. 2A-2C show a set of diagrams and graphs illustrating identification and testing of c-MycPu22 quadruplex DNA binding agents. (A) Cartoon depicting a small molecule microarray screen to identify compounds that bind to c-MycPu22 quadruplex DNA. (B) Structure of a compound identified from the screen to selectively bind to c-MycPu22. Compound 1 increases the melting temperature of quadruplex DNA as measured by circular dichroism (average of 4 trials±standard deviation). (C) Surface plasmon resonance experiment to measure the dissociation constant of Compound 1 binding to c-MycPu22. Shown are the sensorgram (left) and binding isotherm (right).

In order to identify compounds that selectively bind to c-MYC quadruplex DNA, a small molecule microarray (SMM) screening approach was used (FIGS. 1, 2) (Bradner, et al., *Nat Protoc* 2006, 1, 2344; Duffner, et al., *Curr Opin Chem Biol* 2007, 11, 74; Kawasumi, et al., *J Invest Dermatol* 2005, 124, A39; Koehler, et al., *J Am Chem Soc* 2003, 125, 8420; Miao, et al., *J Comb Chem* 2007, 9, 245; Stanton, et al., *Nat Chem Biol* 2009, 5, 154; Vegas, et al., *Angew Chem Int Edit* 2007, 46, 7960). Briefly, a library of 20,000 compounds was covalently immobilized on glass slides using isocyanate surface chemistry, as previously described (Sztuba-Solinska, et al., *J Am Chem Soc* 2014, 136, 8402). Next, a Cy5-labeled c-MYC G4 oligonucleotide derived from the NHEIII$_1$ region of the promoter (Gonzalez and Hurley, Annual review of pharmacology and toxicology 2010, 50, 111) was annealed and incubated with the printed library to identify discrete binding interactions (FIG. 2A). In parallel, several other Cy5-labeled oligonucleotide structures (including RNA hairpins (Sztuba-Solinska, et al., *J Am Chem Soc* 2014, 136, 8402), the FOXO binding domain (Carter and Brunet, *Curr Biol* 2007, 17, R113), and CAG repeat DNA (Michlewski and Krzyzosiak, *J Mol Biol* 2004, 340, 665)) were screened in an analogous manner, which served as controls. For each compound in the library, a composite Z-score was calculated, and the c-MYC G4-incubated data set was compared to a buffer-incubated control data set. Compounds were considered hits if their composite Z-score was greater than three (representing three standard deviations from the mean of the screening library), and if no fluorescence was observed in the buffer-incubated sample. Next, these hit compounds were eliminated if they were also found to bind to other non-homologous oligonucleotides investigated by the same technique.

Figure 2B:
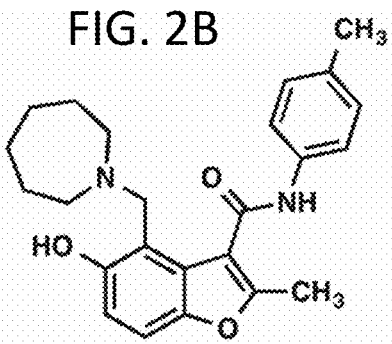
Figure 8:
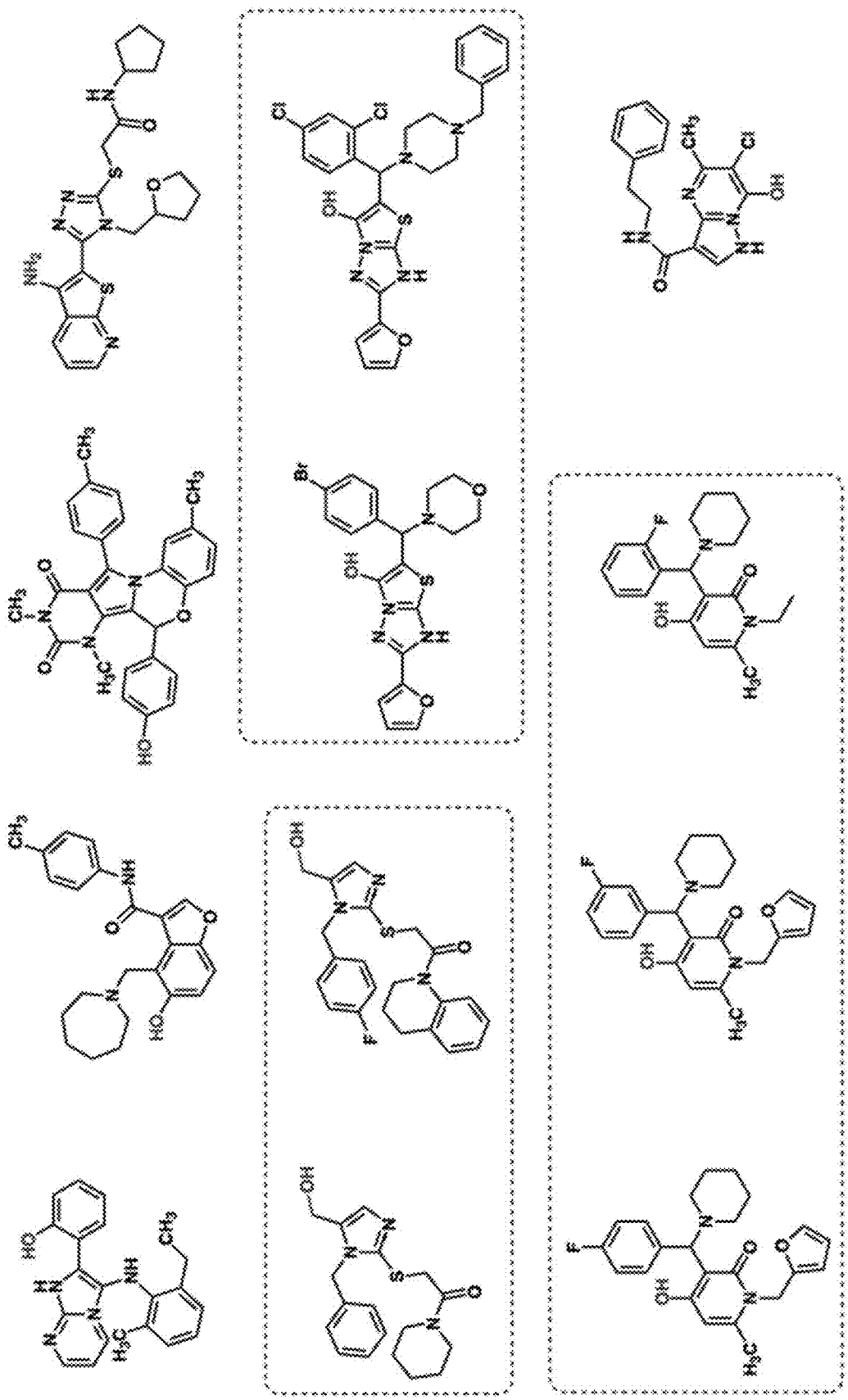
FIG. 8 shows the 12 hits from the screen that were chosen for follow-up studies. Molecules with similar chemical scaffolds are grouped in boxes.

Using these criteria, 32 unique hits were identified as binding selectively to the c-MYC quadruplex structure, for a final hit rate of 0.16%. A panel of the twelve most promising hits was selected for further analysis on the basis of Z-score, qualitative inspection of microarray results, and compound availability (FIG. 8). Each of these compounds was evaluated for its capacity to functionally inhibit c-MYC oncogene transcription and translation, and to reduce cancer cell viability in multiple myeloma cell lines. On the basis of these preliminary studies, Compound 1, a benzofuran structurally unlike any reported quadruplex-binding small molecules, was identified as a promising candidate and it was selected for further in-depth characterization (FIG. 2B).

Figure 9:
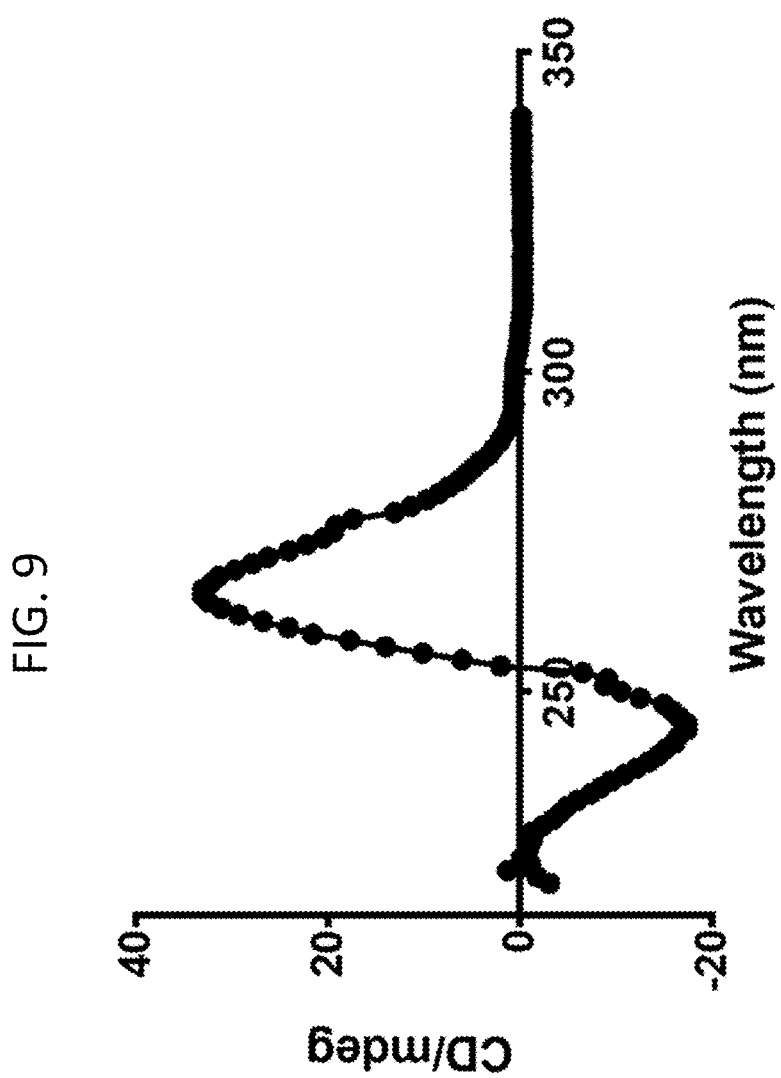
FIG. 9 shows a circular dichroism spectrum of c-MycPu22 quadruplex DNA (SEQ ID NO: 2). Observed maximum (262 nm) and minimum (244 nm) demonstrate formation of a properly folded parallel-stranded G-quadruplex structure.

To assess the ability of Compound 1 to bind to the c-MYC G4 in solution, a CD-based thermal melt experiment was employed. After annealing, the molecular ellipticity of the c-MYC G4 was measured by circular dichroism, where a maximum was observed at 262 nm and a minimum was observed at 244 nm, thus confirming proper folding of the oligonucleotide into a parallel-stranded quadruplex (Mathad, et al., *Nucleic Acids Res* 2011, 39, 9023) (see FIG. 9). Next, molecular ellipticity was monitored at 262 nm as a function of temperature in order to measure the melting temperature ($T_m$). Finally, a sample containing equimolar concentrations of Compound 1 and the c-MYC G4 oligonucleotide was evaluated in the same experiment. Molecules that productively bind to the G4-DNA stabilize the structure and therefore increase its $T_m$ (Murat, et al., *Chemical Society reviews* 2011, 40, 5293). In the presence of Compound 1, the $T_m$ of the G4-DNA increased by 2.1 (±0.5) ° C. (FIG. 2B). This result confirms that the compound binds to and stabilizes quadruplex DNA.

Figure 2C:
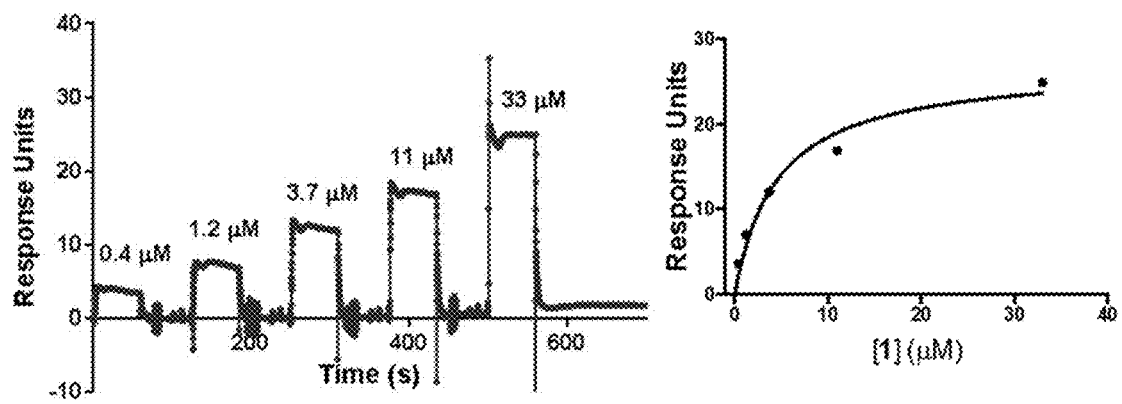

In order to quantitatively assess the binding affinity of Compound 1 with the c-MYC G4, surface plasmon resonance (SPR) experiments (De Crescenzo, et al., *Cell Mol Bioeng* 2008, 1, 204) were performed using a biotinylated c-MYC G4 oligonucleotide. The oligonucleotide was immobilized to a streptavidin-coated chip, and binding was measured as a function of concentration. (FIG. 2). This experiment demonstrates that Compound 1 binds to the c-MYC G4 DNA with an equilibrium dissociation constant ($K_d$) of 4.5±1.4 µM (FIG. 2C). Furthermore, Compound 1 interacts with quadruplex DNA through a reversible binding interaction, and rapid, complete dissociation can be observed in the sensogram (FIG. 2C). Significantly, the data fit well to a 1:1 binding isotherm and the saturation binding measurement of ~20 response units suggests that the binding stoichiometry is likely 1:1. When the same experiment was performed with Quarfloxin, no evidence of binding was observed, pointing to a unique mechanism for transcriptional inhibition of c-Myc with Compound 1.

Figure 3A:
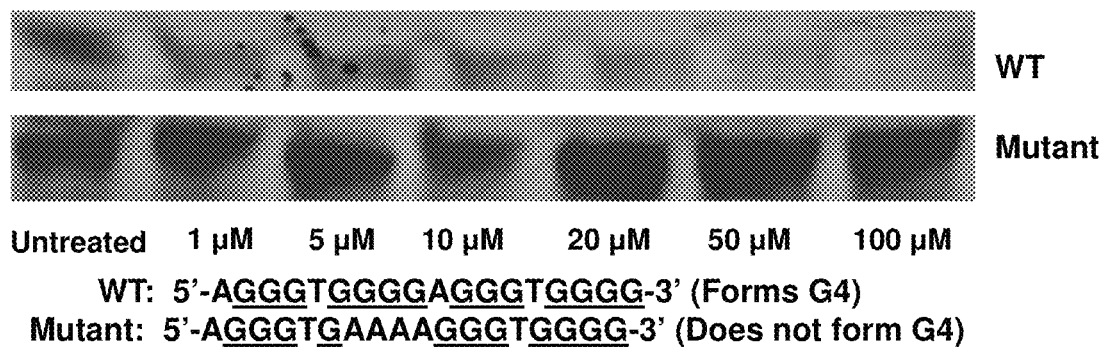
FIGS. 3A-3C show a pair of Western blots and a graph illustrating that compound 1 inhibits c-MycPu22 quadruplex function. (A) PCR stop assay. Compound 1 inhibits PCR amplification of a synthetic wildtype oligonucleotide sequence (nucleotides 3-19 of SEQ ID NO: 2) capable of forming a G4, but not the mutant sequence (SEQ ID NO: 3) that cannot form a G4. (B) Exon specific qPCR assay with CA-46 Burkitt's Lymphoma cell line. Exon 1 (in red) remains under control of the G4 while transcription from exon 2 is not under control of a G4. Cells were treated with 10 μM 1 for the time indicated. Real time polymerase chain reaction was carried out, after which the observed threshold cycle (Ct) was measured and normalized to the value for cells treated with a DMSO control. The data represents an average of four replicates. Error bars represent standard deviation. (C) Western blot demonstrating resistance of CA-46 cell line to inhibition of c-Myc translation.

Next, a modified version of the PCR-stop assay was used to investigate the ability of Compound 1 to inhibit c-MYC DNA amplification in a G4-dependent fashion (Lemarteleur, et al., *Biochem Biophys Res Commun* 2004, 323, 802; Ou, et al., *J Med Chem* 2007, 50, 1465). A linear c-MYC Pu27 (mutant) sequence can be PCR-amplified using normal thermal cycling conditions. However, a G4-containing Pu27 (wild type) sequence blocks polymerase activity and inhibits formation of the PCR product. In the presence of a quadruplex-stabilizing ligand, PCR amplification is inhibited further. Indeed, Compound 1 demonstrated dose-dependent inhibition of PCR amplification for the wild type Pu27 sequence at concentrations comparable to the $K_d$ measured by SPR. In contrast, Compound 1 had no effect at concentrations up to 100 µM on the amplification of a mutant sequence incapable of G4 formation (FIG. 3A). These data point to a G4-dependent mechanism of inhibition by the lead compound in vitro.

Figure 3B:
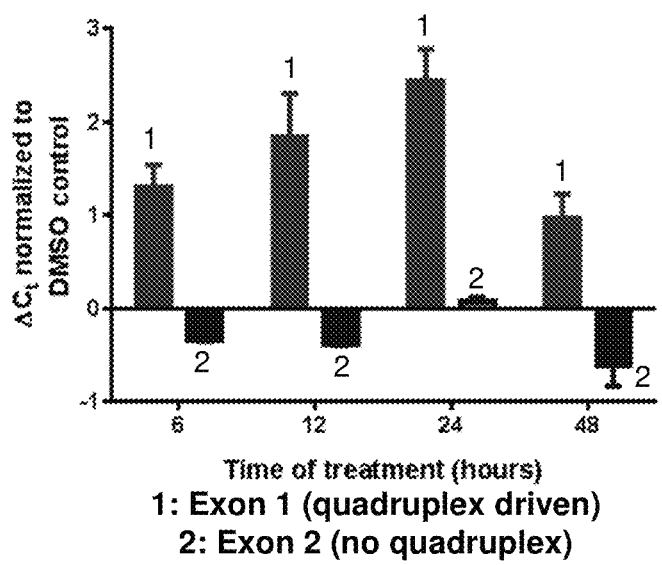
Figure 3C:
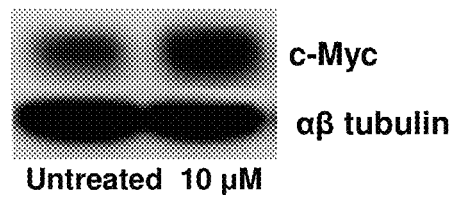

To confirm a G4 specific mechanism of action in cells, the CA46 Burkitt's Lymphoma line was used in an exon-specific assay, as previously reported (Boddupally, et al., *J Med Chem* 2012, 55, 6076). For most cell lines, 85-90% of c-Myc expression is controlled by the G4 located prior to exons 1 and 2 in the promoter. Furthermore, expression predominantly occurs following exon 2, due to a thousand-fold increase in transcription from this allele (Brown, et al., *J Biol Chem* 2011, 286, 41018). The CA46 Burkitt's Lymphoma cell line is an exception to this trend due to the existence of a chromosome (8:14) (Pelicci, et al., *Proc Natl Acad Sci USA* 1986, 83, 2984) translocation between exons 1 and 2, leaving exon 1 under G4 control. As a result, c-Myc expression from exon 2 is G4 independent (FIG. 3B). This renders the overall cell line resistant to G4-mediated c-Myc inhibition at the RNA and protein level, and proliferation should be uninhibited by G4-stabilizing agents. Thus, in the presence of a G4 stabilizing agent, c-Myc transcription from exon 1 should be downregulated, while transcription from exon 2 should be largely unaffected. Using FAM-tagged exon specific TaqMan gene expression assays with qPCR for c-MYC, it was demonstrated that Compound 1 results in sustained downregulation of transcription from exon 1, which contains a quadruplex, while transcription from exon 2, which does not contain a quadruplex, is unaffected at treatment times up to 48 hours (FIG. 3C). This effect is further evidenced by the observation that while Compound 1 silences c-MYC in several other multiple myeloma cell lines, the CA46 Burkitt's Lymphoma cell line is resistant to inhibition of c-Myc protein translation by Compound 1 (FIG. 3C, vide infra).

Figure 4A:
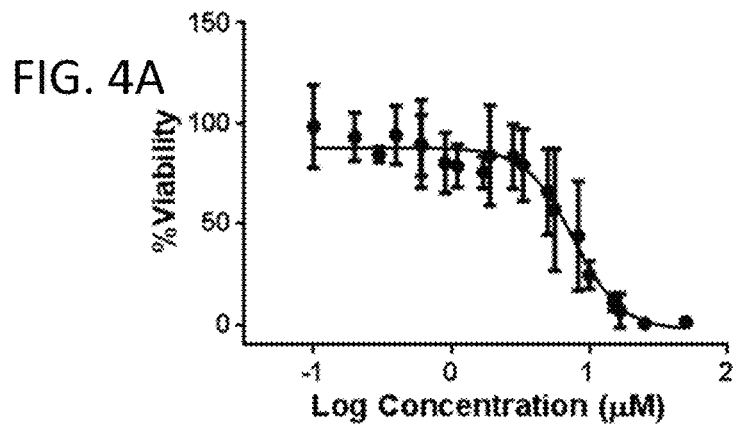
FIGS. 4A-4D show a set of graphs and a Western blot illustrating the effects of Compound 1 on cell viability and c-Myc translation. (A) Dose-dependent effects of Compound 1 on myeloma cell viability at 72 h. (B) Time-dependent inhibition of c-Myc transcription in myeloma cells after treatment with 10 μM 1, as measured by qPCR. Data is average of 2 replicates and error bars represent standard deviation. (C) Inhibition of c-Myc protein translation with 10 μM Compound 1 is sustained over time. (D) Effects on cell viability and c-Myc protein translation by Compound 1 across a panel of multiple myeloma cell lines. Also included are the resistant CA46 Burkitt's Lymphoma cell line and peripheral blood mononucleocytes.
Figure 4B:
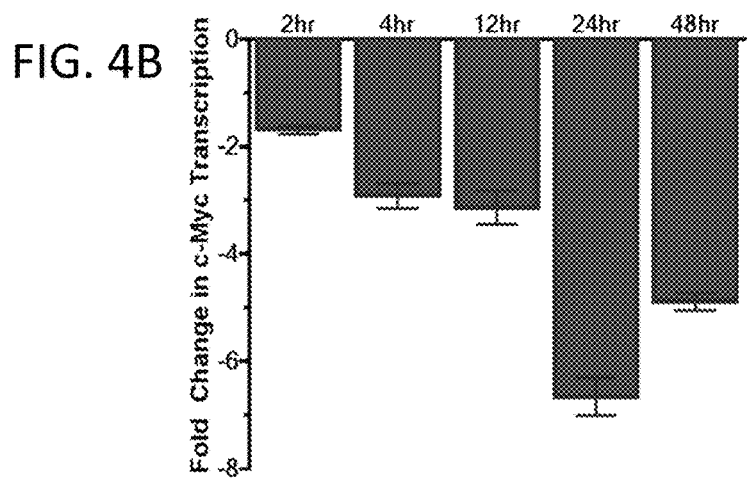
Figure 4C:
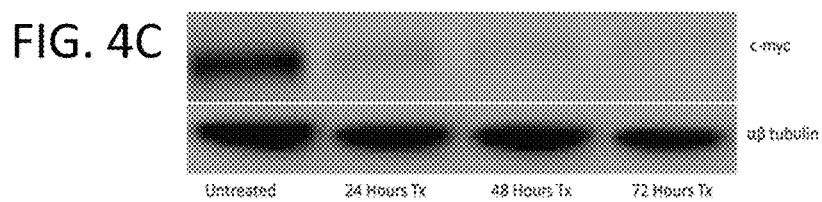
Figure 4D:
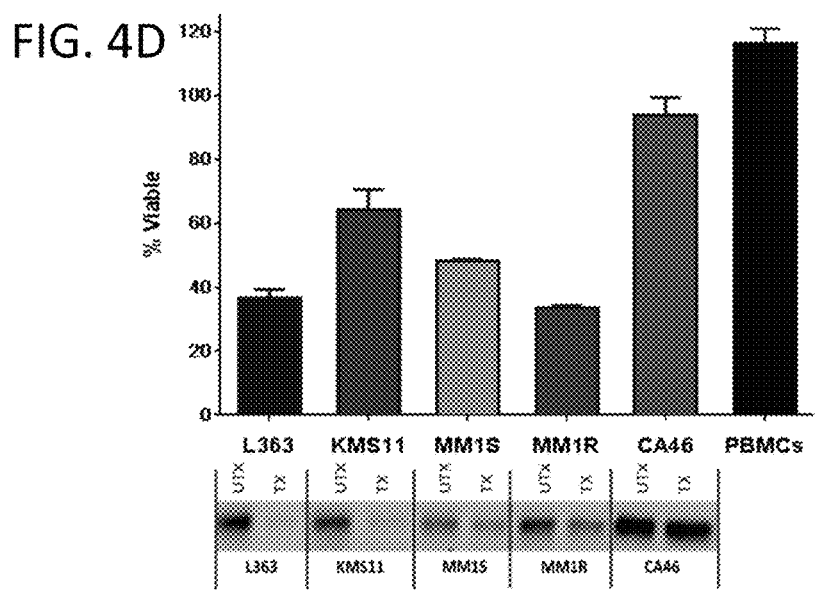

Since two thirds of multiple myeloma cases involve deregulated c-MYC expression (Kuehl and Bergsagel, *Blood* 2012, 120, 2351; Shou, et al., *Proc Natl Acad Sci USA* 2000, 97, 228), we elected to evaluate the cell viability effects of Compound 1 in a multiple myeloma model. Compound 1 inhibited myeloma cell viability in a dose- and time-dependent manner, with an IC$_{50}$ of 7.6±1.1 µM after 72 hours (FIG. 4A). Furthermore, Compound 1 induced a seven-fold decrease in c-Myc transcription after 24 hours (FIG. 4B). Additionally, c-Myc protein translation was also significantly inhibited by exposure to 10 µM of Compound 1. This suppression was maintained over 72 hours, which is notable given the characteristic rapid replenishment of the protein—a phenomenon that complicates targeting c-Myc at the protein level (FIG. 4C). This effect was maintained across a genetically diverse set of 4 multiple myeloma lines. We observed decreases in c-MYC translation in all lines tested, and this effect also correlated with decreases in viability (FIG. 4D). The CA46 Burkitt's Lymphoma line (lacking a G4) was included in this panel as a resistant control, as it showed negligible changes in c-MYC expression or cell viability when treated with Compound 1. Notably, Compound 1 did not alter viability in peripheral blood mononucleocytes drawn from a healthy volunteer, even at doses 25% higher than those used for the cell treatments discussed above (FIG. 4E).

Figure 5A:
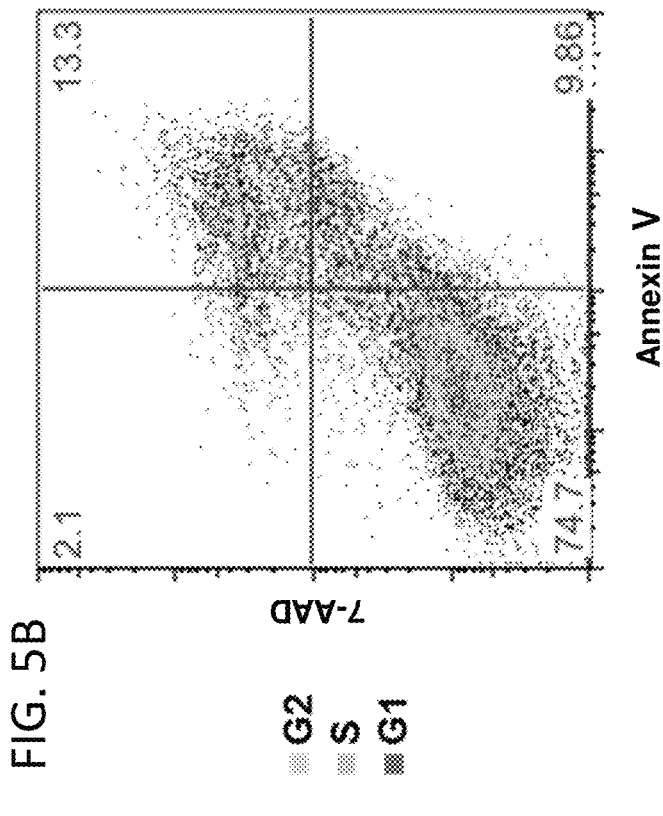
FIGS. 5A-5C show a set of graphs and digital images illustrating that Compound 1 causes cell-cycle arrest in myeloma cells. (A) Cycle analysis for L363 cells treated with 10 μM Compound 1. Compound 1 induces sustained G1 arrest. (B) Compound 1 does not induce significant apoptosis at 10 μM after 72 h. (C) Compound 1 induces a senescent state in myeloma cells at 10 μM after 72 h.
Figure 5B:
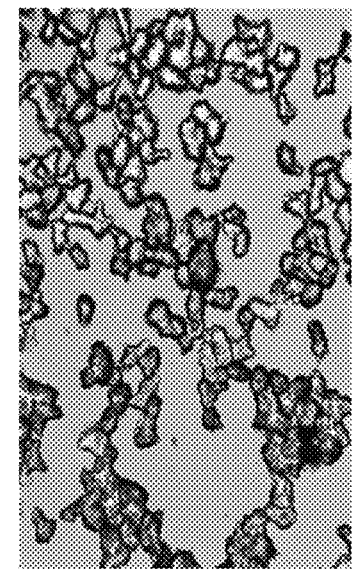
Figure 5C:
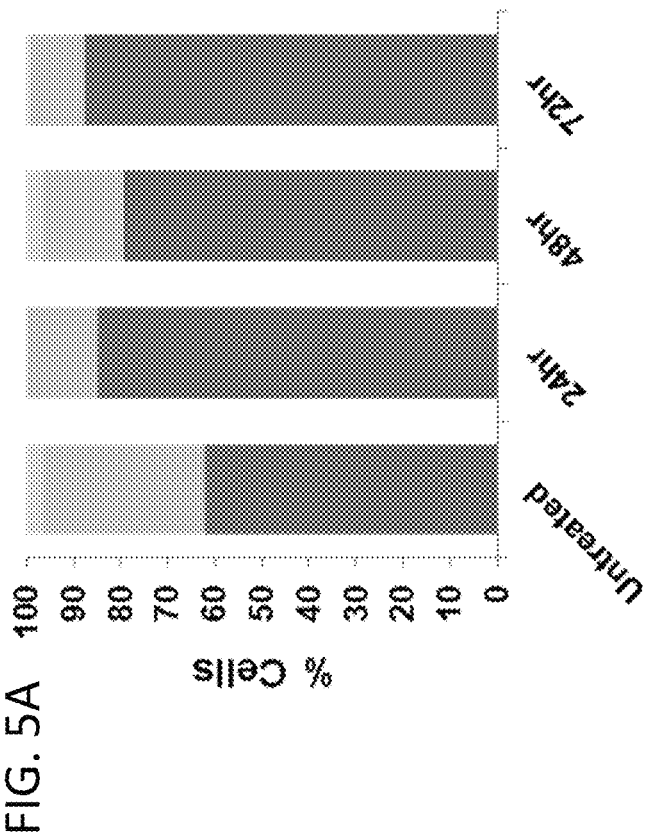
Figure 5C:
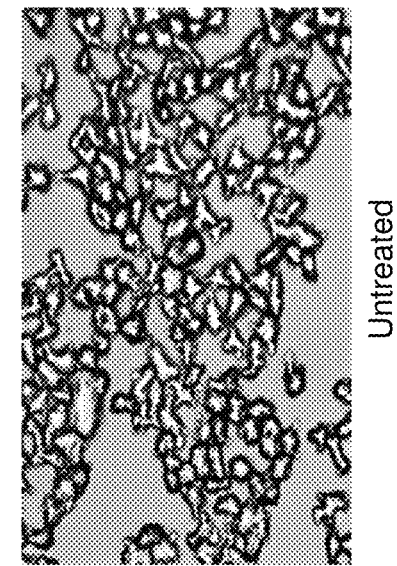

To further explore the mechanism of action for the anticancer activity of Compound 1, cell cycle analysis was performed and monitored for potential induction of apoptotic death. Compound 1 was observed to causes ~85% of treated cells to arrest in the G1 phase after 72 hours, as measured by propidium iodide staining (FIG. 5A). Additionally, minimal increases in apoptosis were observed, by Annexin V/7-AAD staining and FACS analysis; only 13% of the cells were undergoing apoptosis (FIG. 5B). These results may be indicative of the low nonspecific cytotoxicity and high target specificity of Compound 1, which is important in achieving a useful therapeutic window. Additionally, Compound 1 triggered a senescent state in a majority of treated myeloma cells after 72 hours, supporting cell cycle arrest as a primary mechanism of action (FIG. 5C). Taken together, these results support that Compound 1 is acting through suppression of c-MYC expression, rather than a non-specific mechanism of action.

Having demonstrated that Compound 1 suppresses c-MYC expression, subsequent experiments focused on gaining insight into the specificity of Compound 1 by probing effects on gene expression in a broader sense. Gene expression analysis was performed on a panel of 770 cancer-associated genes in a multiplexed (nanostring) transcriptional assay. In addition to c-MYC itself, several c-Myc target genes were included in the panel, as were a number of other quadruplex-driven genes. Cells were treated with 10 μM Compound 1 for 2 h, 4 h, 12 h, 24 h, and 48 h, and separately with doses of 1, 2.5, 5, and 10 μM at a time point of 24 h, and the effects on gene expression were evaluated. c-MYC was one of the most suppressed genes, and a number of known c-Myc target genes were also suppressed, including E2F1, MCM2, MCM4, MCM5, and CDC25A. Additionally, a third data set was collected comparing Compound 1 treatment to JQ-1 (a BET-bromodomain inhibitor) and quarfloxin (another quadruplex-binding small molecule). All three inhibitors exhibited substantial differences in gene expression profiles, highlighting a unique mechanism of action of Compound 1.

Figure 14A:
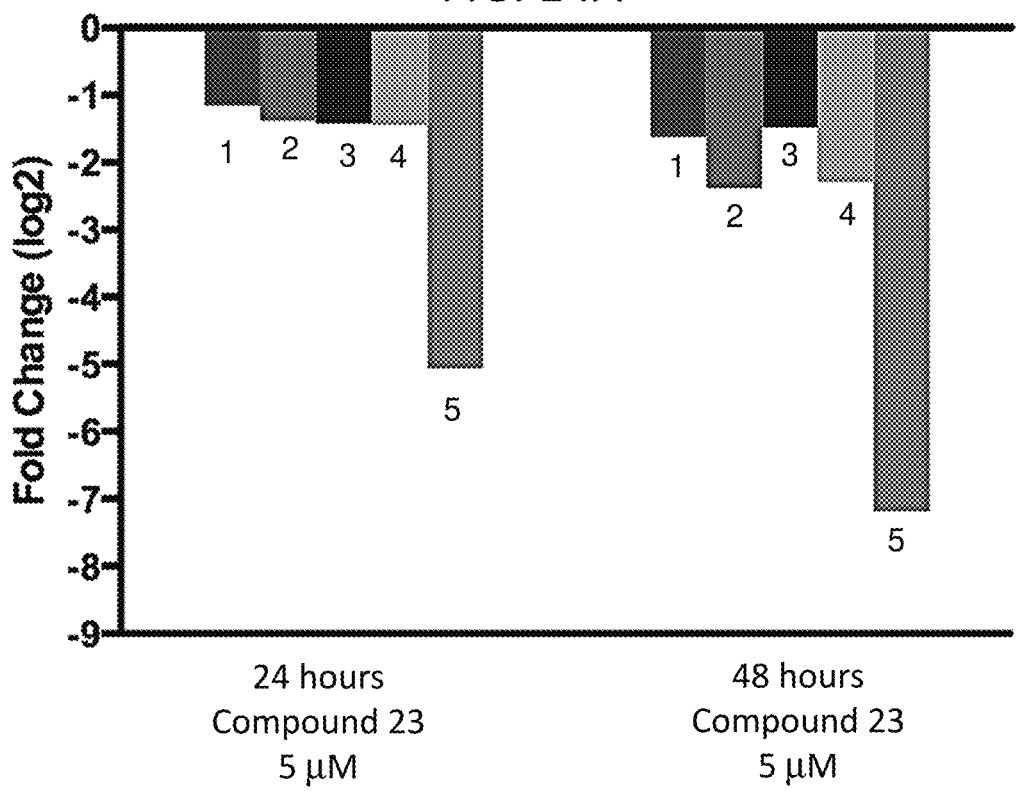
FIGS. 14A and 14B are a set of graphs illustrating the effect of Compound 1 or Compound 23 treatment on gene expression. (A) Treatment of L363 cells with 5 µM Compound 23 for 24 or 48 hours reduced c-Myc expression while minimally affecting expression of other G-quadruplex containing genes as evaluated using qPCR analysis. (B) Treatment of L363 cells with 10 µM BRACO-19, 10 µM Compound 1 or 7.5 µM Compound 23 for 48 hours reduced c-Myc expression while minimally affecting expression of other G-quadruplex containing genes as evaluated using qPCR. The expression levels of the BCL2 (1), KRAS (2), HIF1A (3), VEGFA (4), and c-MYC (5) genes is shown.
Figure 14B:
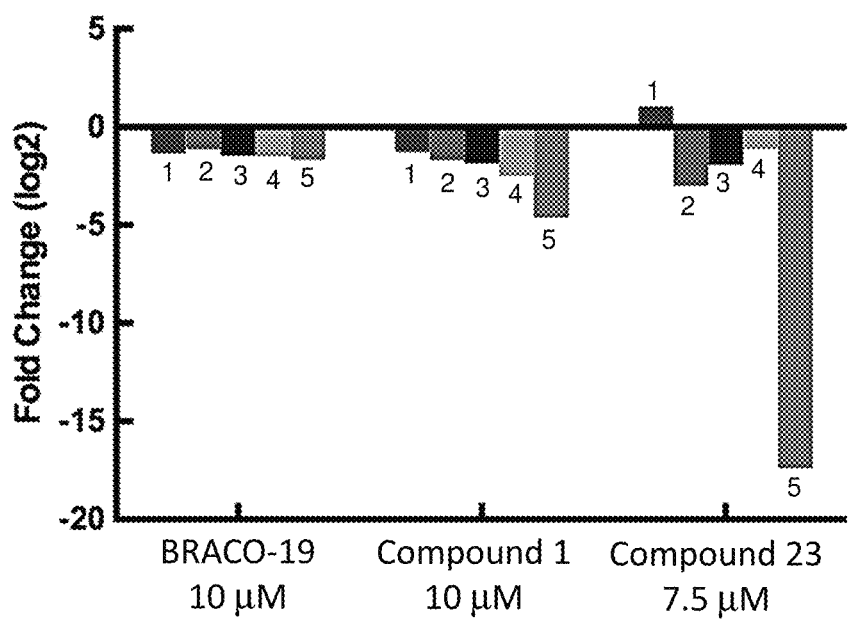

The effects of Compound 1 on a number of known quadruplex-driven genes in the panel were examined further (FIG. 6). Expression levels of MYC, RB1, VEGFA, KRAS, and HIF1α, all of which are reported to be under the control of promoter G4s, and are expressed in L363 cells, were included in the panel of genes evaluated by Nanostring as discussed above. The change in expression for each of these genes (nanostring) over time is presented in FIG. 6A. While MYC expression was substantially reduced at all time points, expression of other G4-associated genes was minimally affected. To further confirm these results, we also performed qPCR experiments on these genes following treatment with Compound 1 (FIG. 6B). Again, MYC expression is greatly reduced while other genes are minimally affected. These changes in gene expression are in line with biophysical measurements of compound affinity. Corresponding data showing similar results is presented for Compounds 1 and 23 in FIGS. 14A and 14B. While the quadruplex with the highest affinity for Compound 1 (MYC) had pronounced changes in gene expression, G4s with weaker binding (RB1, BCL2) or a complete lack of G4 binding (KRAS, VEGF) had minimal changes in expression, even after 48 h of treatment. These observations further highlight the ability of Compound 1 and Compound 23 to specifically target the expression of c-Myc and related pathways.

Figure 7:
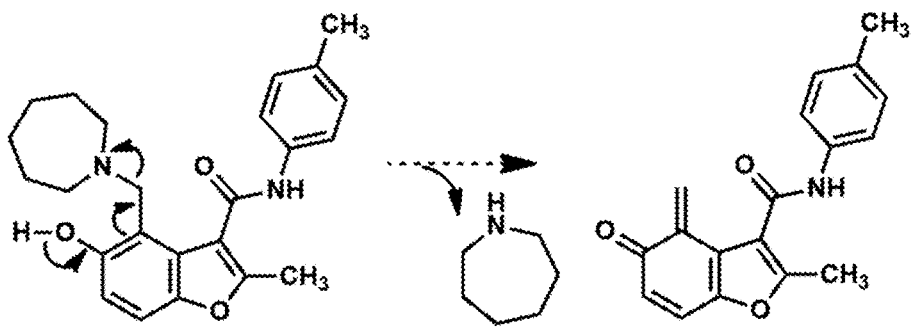
FIG. 7 illustrates potential decomposition pathways for Compound 1.
Figure 7:
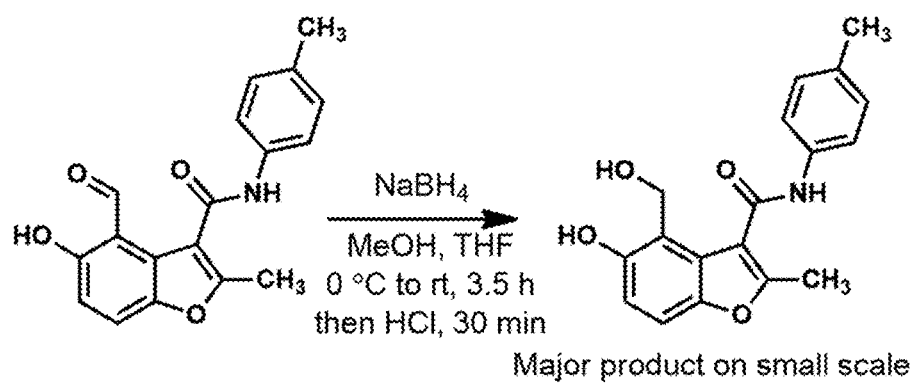
Figure 7:
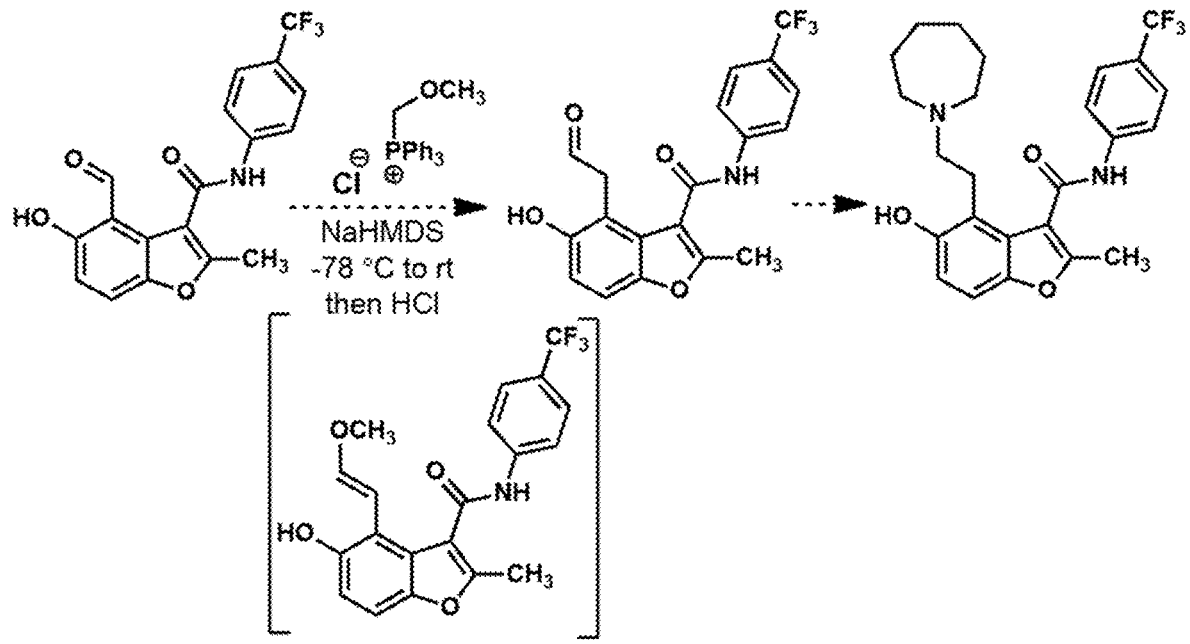

Having established the reversible binding of Compound 1 to quadruplex DNA and selective quadruplex-dependent silencing of c-Myc, one consideration that remained was the presence of a benzylaminophenol functional group in Compound 1. It has previously been reported that compounds containing this functional group can have the propensity to eject amines, form an o-quinone methide, and alkylate proteins (Weinert, et al., *J Am Chem Soc* 2006, 128, 11940; Herzig, et al., *J Org Chem* 2006, 71, 4130; McLean, et al., *Bioorg Med Chem Lett* 2009, 19, 6717). To assess whether Compound 1 was undergoing this reactivity, a small series of analogs was prepared. In FIG. 6C, compounds lacking the phenol or amino group were prepared and evaluated. As can be observed, a compound incapable of forming a quinone methide retains activity in silencing c-MYC expression, while a compound lacking the amino substitution is not active, demonstrating the importance of the amino group for activity. Additionally, the stability of Compound 1 was evaluated (see FIG. 7). Here, Compound 1 persisted in culture media over a period of 72 h as monitored by LC/MS, confirming that the compound is largely stable in complex, biologically relevant mixtures over the timeframe of viability assays used in this study. Additionally, the putative hydrolysis products arising from quinone methide formation were not observed at any time by LC/MS. Taken together, these data point toward a reversible binding interaction not dependent on the formation of a quinone methide.

Conclusion

The overexpression of c-MYC is implicated in a vast number of human cancers, however only a small number of inhibitors have been described in the literature, and as of now none are clinically approved. Pharmacological inhibition of c-Myc has historically been a challenge, and small molecules that are efficacious in cells are relatively rare. G4-DNA stabilization and subsequent transcriptional silencing by a small molecule is an attractive strategy for c-MYC inhibition because it circumvents targeting c-Myc at the protein level. Nevertheless, many of the compounds currently known to bind to the c-MYC G4 generally have poor drug-like properties, nonspecific quadruplex binding, or exhibit quadruplex-independent effects in more complex cell culture models.

To address challenges in the identification of c-MYC G4-binding compounds, a small molecule microarray-based screening approach was employed. By evaluating multiple oligonucleotide structures simultaneously as part of the initial screen, selectivity considerations were incorporated early in the discovery process. Through evaluation of the most promising hits in preliminary assays, Compound 1 was pursued for further investigation. The benzofuran structure of Compound 1 is a novel quadruplex-binding small molecule scaffold. Molecules containing benzylaminophenol groups have previously been reported to form quinone methide structures in aqueous solution. However, in this case a stability study demonstrated that the compound persists for three days in culture media. Furthermore, reversible binding was demonstrated by SPR experiments, where a $K_d$ of 4.5±1.4 µM was measured, with an apparent 1:1 binding stoichiometry. By evaluating a small panel of analogs of Compound 1, further information about the pharmacophore was gained. A compound lacking the amine was completely inactive, while an analog lacking the phenol group (incapable of forming a quinone methide) retained activity. Thus, the amine functionality is likely required for binding to the quadruplex, while the formation of a quinone methide structure is unlikely to be involved in the mechanism. In contrast to quinone methide-forming alkylators, which are typically non-specifically toxic, Compound 1 displays no toxicity to the CA46 resistant cell line or peripheral blood mononucleocytes at relevant concentrations, further suggesting on-target activity as the origin of the observed effects in cells.

In culture models, Compound 1 inhibits c-MYC expression at both the transcriptional and translational levels. Moreover, it decreased the viability of several myeloma cell lines in a dose dependent fashion. Cell cycle analysis demonstrates that Compound 1 also triggers G1 arrest and senescence in myeloma cells, which is consistent with literature findings regarding effects of c-MYC knockdown on cell cycle progression (Wang, et al., *Oncogene* 2008, 27, 1905). In sum, these results validate that Compound 1 effectively suppresses c-MYC expression through a G4-dependent inhibitory mechanism in vitro and in cancer cells.

Through gene expression profiling, further evidence for the suppression of c-Myc and related proteins was observed. In a panel of 770 cancer-related genes, the expression of c-MYC itself and a number of c-Myc target genes were suppressed in a dose- and time-dependent manner. In comparison to quarfloxin and JQ1, Compound 1 appears to have a unique mechanism of action and modulates a distinct subset of genes. Importantly, in depth analysis of the data set indicated that several other known quadruplex-driven genes were not affected by Compound 1. Thus, Compound 1 has specific effects for the c-MYC quadruplex over several other quadruplex sequences within the genome. Furthermore, transcriptional profiling provides evidence for the selective modulation of the c-MYC pathway in a broader sense.

Materials and Methods

General Materials and Methods.

Reactions were conducted using anhydrous solvents (passed through activated alumina columns). All commercially obtained reagents were used as received. Flash column chromatography was performed using normal phase silica gel (60 Å, 230-400 mesh, RediSep® Normal-phase Silica Flash Columns) on a CombiFlash® Rf 200i (Teledyne Isco Inc). Preparative HPLC was performed with a Waters® 2545 Binary Gradient Module equipped with a Waters® 2767 Sample Manager fraction collector and a Luna 10 µm C18 110 Å (75×30 mm) column obtained from Phenomenex, Inc. High-resolution LC/MS analyses were conducted on a Thermo-Fisher LTQ-Orbitrap-XL hybrid mass spectrometer system with an Ion MAX API electrospray ion source in positive ion mode. Analytical LC/MS was performed using a Shimadzu LCMS-2020 Single Quadrupole utilizing a Kinetex 2.6 µm C18 100 Å (2.1×50 mm) column obtained from Phenomenex Inc. Runs employed a gradient of 0→90% MeOH/0.1% aqueous formic acid over 4.5 min at a flow rate of 0.2 mL/min. $^1$H NMR and $^{13}$C NMR spectra were recorded on Varian and Bruker spectrometers (at 400 or 500 MHz or at 100 or 125 MHz) and are reported relative to deuterated solvent signals. Data for $^1$H NMR spectra are reported as follows: chemical shift (δ ppm), multiplicity, coupling constant (Hz), and integration. Data for $^{13}$C NMR spectra are reported in terms of chemical shift. Surface plasmon resonance analysis was performed at the ATRF (NCI-Frederick) using a Biacore T200 (GE Healthcare).

Small Molecule Microarray Screening.

Small molecule microarray screening was carried out as previously described (Duffner, et al., *Curr Opin Chem Biol* 2007, 11, 74; Sztuba-Solinska, et al., *J Am Chem Soc* 2014, 136, 8402; Bradner, et al., *Nat Protoc* 2006, 1, 2344). Briefly, γ-aminopropyl silane (GAPS) microscope slides were functionalized with a short Fmoc-protected amino polyethylene glycol spacer. After deprotection using piperidine, 1,6-diisocyanatohexane was coupled to the surface by urea bond formation to provide functionalized isocyanate-coated microarray slides that can react with primary alcohols and amines to form immobilized chemical screening libraries. 20,000 unique small molecule stock solutions (10 mM in DMSO) purchased from ChemBridge and ChemDiv screening libraries, in addition to dyes and controls, were printed in duplicate onto four slides of 5,000 compounds each, and exposed to pyridine vapor to facilitate covalent attachment to the slide surface. After drying, slides were incubated with a polyethylene glycol solution to quench unreacted isocyanate surface. Printed slides were incubated for 1 h at room temperature with a Cy5-tagged DNA oligonucleotide of the c-MYC G-quadruplex forming sequence (5'd(Cy5)-TGAGGGTGGGTAGGGTGGGTAA-3', SEQ ID NO: 2), which had been annealed by heating to 95° C. for three minutes, cooled to room temperature, and diluted to 500 nM in PBS. Following incubation, slides were gently washed three times for 5 min in PBST, twice in PBS, and once in deionized water to remove unbound oligonucleotide, and dried by centrifugation for 2 min at 3400 g. Fluorescence intensity was measured (650 nm excitation, 670 nm emission) on a GenePix 4000a Microarray Scanner. Hits were identified on the basis of signal-to-noise ratio (SNR), defined as (mean foreground−mean background)/ (standard deviation of background), and Z-score, with the following criteria: (1) Raw SNR >0, (2) SNR >3 SD above negative control readings, (3) coefficient of variance (CV) of replicate spots <100, (4) SNR of negative control slide <1, and (5) no activity with any other nucleic acid structures screened. The other nucleic acids were the FOXO3 DNA transcription factor binding domain, CAG DNA repeat, HIV TAR RNA, and miR-21 RNA, all of which were Cy5-labeled, and the screens were run in the same method described above using the respective Cy5-nucleic acid instead of the c-MYC DNA.

PCR Stop Assay. A test oligonucleotide and a complementary sequence that partially hybridizes to its last G-repeat (sequences below) were synthesized by IDT. The reactions were performed in a master mix containing 1×PCR buffer, 10 µmol of each oligo, 0.16 mM dNTP, 1.5 mM $MgCl_2$, 2.5 U HotStarTaq polymerase (Qiagen), and a dose titration of a ligand of interest, spanning three orders of magnitude, in 25 µL total volume. The thermal cycling conditions were as follows: 94° C. for 5 min, followed by 22 cycles of 94° C. for 30 s, 58° C. for 30 s, 72° C. for 30 s, and finally held at 4° C. following completion. The amplified products were mixed with 6×DNA Loading Dye (Thermo Scientific) and resolved on a 15% TBE-Urea Gel (Invitrogen) on the Novex mini gel system at 150 V for 1 h. The gel products were stained in a 0.01% (v/v). Ethidium Bromide-TBE solution for 15 min and imaged under UV light on the GBOX F3 (Syngene).

Oligos Used:

```
Forward
5'-AGG GTG GGG AGG GTG GGG-3',
nucleotides 3-19 of SEQ ID NO: 2
(Partial sequence in the promoter of oncogene
c-MYC that may form G-quadruplex.)

Forward Mutant
                                    SEQ ID NO: 3
5'-AGG GTG AAA AGG GTG GGG-3', Reverse
                                    SEQ ID NO: 4
5'-ATC GAT CGC TTC TCG TCC TTC CCC A-3',
(Complementary sequence used for both forward and
reverse.)
```

Exon Specific Assay.

CA46 cells were treated with ligands of interest or DMSO control at designated time points, washed in PBS, flash frozen, and RNA isolated using the Qiagen RNeasy Kit. RNA was quantified by NanoDrop, and 0.5 µg was reverse transcribed for use in qPCR. Reverse transcription was performed using the Applied Biosystems Kit B808-0234, cycled at 25° C. for 10 min, 48° C. for 60 min, 95° C. for 5 min, and held at 4° C. following completion in 25 µL total volumes. The cDNA was diluted four fold and used in qPCR with the Taqman Gene Expression Assays (Life Technologies, exon 1: 01562521_m1, exon 2: 00153408_m1), cycled at 50° C. for 2 min, 95° C. for 10 min, and followed by 40 cycles of 95° C. for 15 s and 60° C. for 1 min on the Applied Biosystems 7500 Fast Real-Time PCR System. For exon 1 and exon 2, $\Delta C_t$ was normalized to a VIC-Primer Limited tagged GAPDH Taqman Gene Expression Assay (multiplexed in the same well) and DMSO treated control samples.

CD-Thermal Melt Assay.

Thermal stability of the c-MYC G4-forming oligonucleotide Pu22 (TGAGGGTGGGTAGGGTGGGTAA, SEQ ID NO: 2) in the absence and presence of compounds was recorded on an Aviv Biomedical Inc. Model 420 Circular Dichroism Spectrometer. The c-MYC G-quadruplex was diluted to 50 µM in 10 mM Tris buffer (pH 7.5, containing 100 mM KCl), heated to 95° C. for 5 min, and allowed to cool to room temperature. Positive molecular ellipticity of the parallel G-quadruplex peak (262 nm) was confirmed by spectral examination. To 150 µL of the G-quadruplex in buffer was added one equiv. of compound (150 µL of a 50 µM solution in buffer containing 0.5% DMSO), after which the mixtures were heated from 5 to 95° C. at 2° C./min in a 0.1 mm quartz cell. Molecular ellipticity as a function of temperature was used to calculate a $T_m$ (the temperature at which 50% of the formed higher order DNA structure was melted) for each condition using GraphPad Prism 6 software and a nonlinear regression model with a variable slope. $\Delta T_m$ values were calculated as $T_{m(+compound)} - T_{m(control)}$.

Surface Plasmon Resonance (SPR).

SPR experiments were performed with a Biacore T200 (GE Healthcare). 20 µg/mL biotin-labeled Pu22 G-quadruplex in 10 mM Tris buffer (pH 7.5, containing 100 mM KCl, 3 mM EDTA) was heated to 95° C. for 5 min, and allowed to cool to room temperature. The c-MYC DNA was then captured (FC2: 1245 Ru) on a Series S Sensor CM5 Chip (GE Healthcare) with amine-coupled Neutravidin (FC1: 4466 Ru, FC2: 5458 Ru). Single Cycle Kinetics (SCK) experiments were carried out with five injections of increasing concentration of analyte solution, which was prepared by a three-fold serial dilution of compound with buffer (10 mM Tris pH 7.5, 100 mM KCl, 3 mM EDTA) containing 3% DMSO. Binding analysis was conducted at a flow rate of 30 µL/min at 25° C. In each run, the association phase and the subsequent dissociation phase were monitored for 1 min and 10 min, respectively. Prior to each compound injection, three buffer injections were made. From the obtained reference-subtracted sensorgrams, the dissociation constants ($K_d$) of the compounds were estimated by a global fitting to a simple 1:1 binding model in the Biacore evaluation software (GE Healthcare).

Cell Culture Conditions and Experimental Endpoints.

Human multiple myeloma and Burkitt's Lymphoma cell lines L363, CA46, MM-1R, KMS-11, and MM-1S were cultured and authenticated as previously described (Simmons, et al., *Molecular oncology* 2014, 8, 261). All plasma derived cell lines were cultured in RPMI-1640 (2 mM L-glutamine, 10% fetal bovine serum (FBS), 100 U/ml penicillin, 100 µg/ml streptomycin: Gibco) and incubated at 37° C. with 5% $CO_2$. Viability experiments were performed in quadruplicate on 96-well plates (Costar) at designated time and dose points. MTS reagent was then directly added, incubated at 37° C. for 90 min, and absorbance of MTS formazan was read at 500 nm on an Omega 640 spectrophotometer. Percentage cell viability was normalized to the absorbance of untreated (DMSO) wells. In the case of cells harvested for their protein or RNA, pellets were flash frozen and stored at −80° C. overnight prior to use.

Western Blots.

Cell pellets/tissue were homogenized and lysed in RIPA buffer on ice for 1 h. Protein was quantitated by BCA, and equal protein was loaded onto 4-12% Bis-Tris Gels (Novex), electrophoresed at 150 V for 75 min to obtain sufficient separation, and transferred via the iBlot system (Life Technologies). Successful transfer and uniform loading was confirmed by Ponceau S staining (Thermo Scientific). Blots were blocked in 10% dry milk in TBST, incubated with primary monoclonal antibodies in 5% BSA at concentrations designated by the manufacturer, and gently rotated at 4° C. overnight. Blots were washed with TBST three times prior to incubation with polyclonal secondary antibodies for 1 h in 5% dry milk at room temperature. Blots were washed three more times with TBST and imaged with Supersignal West Dura Chemiluminescent Substrate (Thermo Scientific) on the GBOX F3 (Syngene). The c-Myc monoclonal antibody was purchased from abcam (ab84132) and used at a concentration of 1:1000. All other monoclonal antibodies were purchased from Cell Signaling Technologies and used at a concentration of 1:1000, with the exception of α-β tubulin, which was used at a concentration of 1:2000. All primary antibodies used in this study were of rabbit origin, and goat anti-rabbit IgG (H+L) horseradish peroxidase conjugate (Invitrogen G21234) was used as the polyclonal secondary antibody at a concentration of 1:4000.

Cancer Genome-Wide Probing and Statistical Packaging.

The phenotype for c-MYC genetic knockdown in multiple myeloma was achieved through lentiviral transduction of shRNA for c-MYC, derived from the spinoculation of 293T cells and plasmids grown in STBL3 *E. coli*, and isolated with the Qiagen Plasmid Midi Kit. Aliquots of the plasmids were generously provided by Art Shaffer. RNA of treated myeloma cells at designated time points was isolated with the Qiagen RNeasy kit, and used with the nCounter Human Cancer Reference Kit (NanoString Technologies), surveying changes in expression for 780 cancer-related human genes and 6 reference genes. Quantitative changes in expression were analyzed and grouped in the form of a heat map using the programming language, R. All other quantitative statistical packing was performed in GraphPad Prism.

Stability Study.

Compound 1 (10 μL of 1 mM DMSO solution) was added to 490 μL RPMI-1640 culture media. After 1 min, 25 h, 48 h, and 72 h, 100 μL of this solution was diluted into 100 μL acetonitrile. The mixture was centrifuged at 5500 rpm for 1 min and the supernatant was removed from the pellet. Another 800 μL MeCN was added to the supernatant and the mixture was centrifuged again at 5500 rpm for 1 min. The resulting supernatant was subjected to LC/MS (ESI+) on an Agilent Technologies 1200 LC/MSD single quadrupole system, equipped with an in-line diode-array UV detector. The mass corresponding to Compound 1 (M+H$^+$=393) was extracted. This mass persisted as a significant peak through 72 h. Masses of the putative hydrolyzed compound (see structure below; M+H$^+$=312) and o-quinone methide compound (see structure below; M+H$^+$=294) were extracted, and were found to be insignificant at all time points (see the chromatograms below).

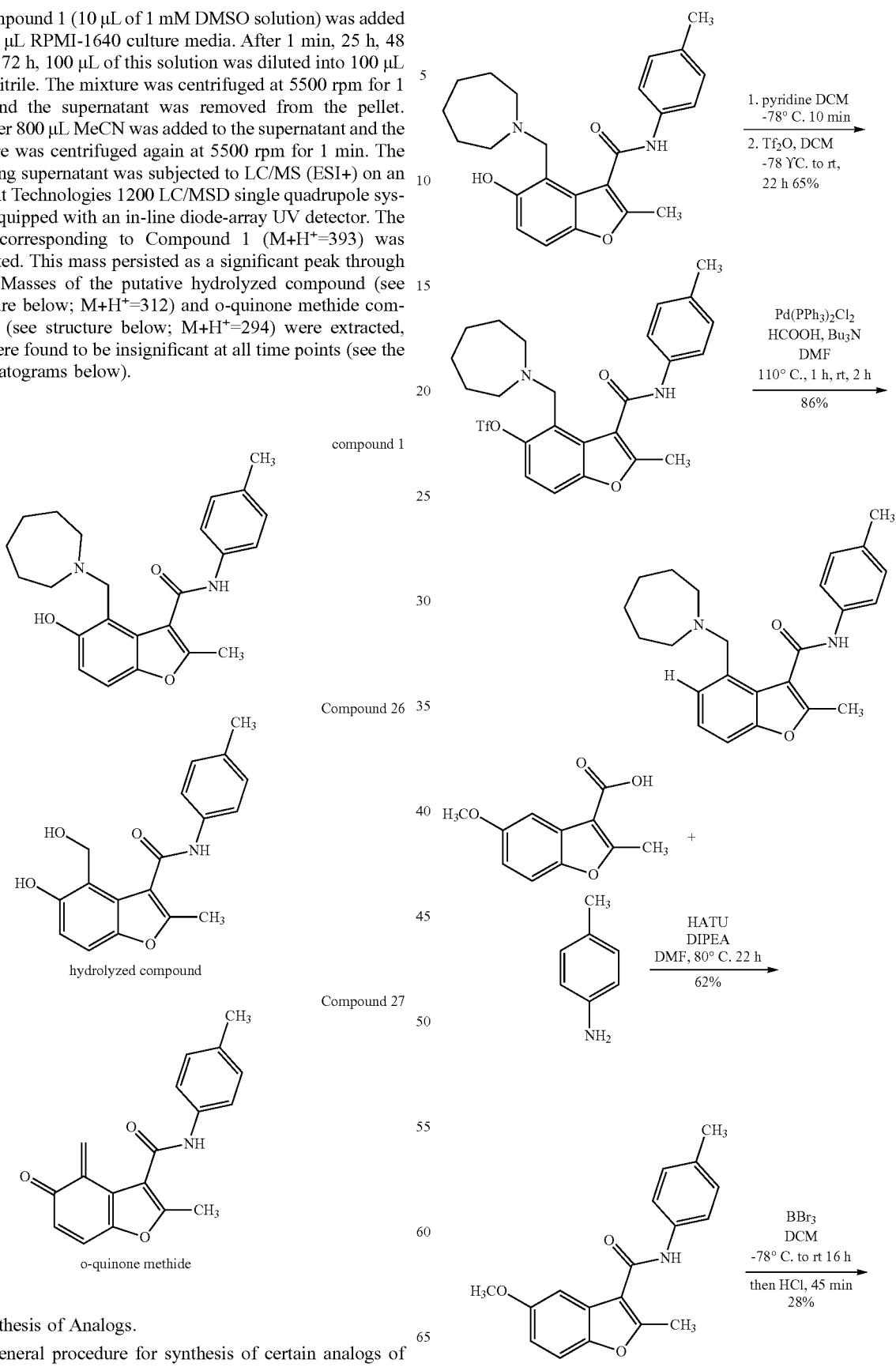

compound 1 hydrolyzed compound o-quinone methide

Synthesis of Analogs.

A general procedure for synthesis of certain analogs of Compound 1 is shown below:

-continued

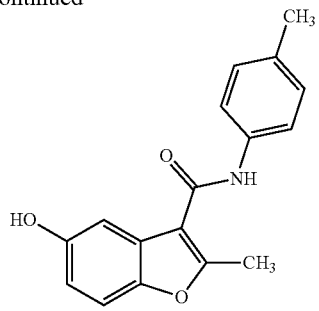

Additional details are provided below.

Compound 16

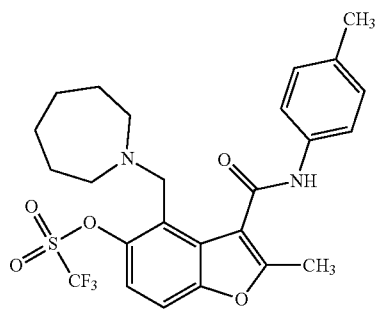

A solution of phenol (Otava 7018860558, 12 mg, 0.028 mmol) in DCM (0.28 mL) was cooled to −78° C. Pyridine (4.5 µL, 0.056 mmol) was added and the solution was stirred for 10 min. At this point trifluoromethanesulfonic anhydride solution (1M in DCM, 34 µL, 0.034 mmol) was added slowly. The reaction was gradually warmed to rt overnight. After a total of 23 h, the solvent was removed in vacuo and the residue was purified by flash column chromatography (10-50% EtOAc/hexanes) to provide X (9.5 mg, 65%) as a white solid. $R_f$=0.71 (33% EtOAc/hexanes). $^1$H NMR ((CD$_3$)$_2$SO, 400 MHz) δ 10.35 (s, 1H), 7.70 (d, J=9.0 Hz, 1H), 7.67 (d, J=8.4 Hz, 2H), 7.32 (d, J=9.0 Hz, 1H), 7.16 (d, J=8.3 Hz, 2H), 3.83 (s, 2H), 2.59 (s, 3H), 2.38-2.31 (m, 4H), 2.29 (s, 3H), 1.41-1.34 (m, 4H), 1.34-1.25 (m, 4H). $^{13}$C NMR ((CD$_3$)$_2$SO, 125 MHz) δ 161.0, 157.5, 151.8, 144.0, 136.9, 132.3, 129.1, 127.3, 125.8, 119.1, 118.1 (q, $J_{C-F}$=320 Hz), 117.1, 116.5, 111.5, 54.4, 51.7, 26.8, 26.2, 20.5, 13.5; HRMS (ESI) calculated for C$_{25}$H$_{28}$N$_2$O$_6$S (MH$^+$) 541.1615, observed 541.1615.

Compound 15

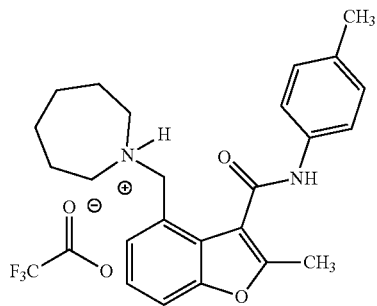

To a solution of triflate X (3.1 mg, 0.0059 mmol) in DMF (60 µL, 0.098 M) was added formic acid (0.56 µL, 0.014 mmol), tributylamine (5 µL, 0.063 mmol), and Pd(PPh$_3$)$_2$Cl$_2$ (0.5 mg, 0.0007 mmol) successively under Ar. The solution was heated to 110° C. for 1 h at which point it was cooled to room temperature. The mixture was filtered through cotton and the filtrate was purified by HPLC (10-95% MeCN/H2O containing 0.1% TFA in the running buffer) to provide X as a white solid (2.5 mg, 86%). $^1$H NMR ((CD$_3$)$_2$SO, 500 MHz) δ 10.64 (s, 1H), 9.48 (brs, 1H), 7.76 (t, J=4.5 Hz, 1H), 7.63 (d, J=7.9 Hz, 2H), 7.45 (d, J=4.6 Hz, 2H), 7.23 (d, J=7.9 Hz, 1H), 4.60 (d, J=5.3 Hz, 2H), 3.28-3.09 (m, 4H), 2.66 (s, 3H), 2.31 (s, 3H), 1.89-1.69 (m, 4H), 1.67-1.47 (m, 4H); $^{13}$C NMR ((CD$_3$)$_2$SO, 125 MHz) δ 165.1, 163.3, 157.5, 153.5, 135.8, 133.8, 129.3, 128.9, 128.2, 124.8, 120.4, 119.1, 117.4 (q$_{C-F}$, J=301.8 Hz), 113.8, 112.8, 54.5, 53.7, 27.3, 26.1, 20.5, 14.0; HRMS (ESI) calculated for C$_{24}$H$_{29}$N$_2$O$_2$ (MH$^+$) 377.2224, observed 377.2225.

Compound 36

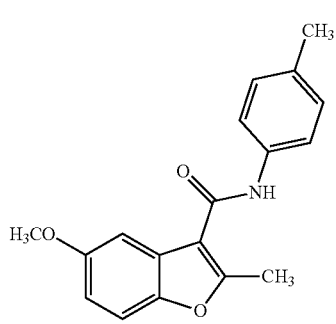

To a solution of 5-methoxy-2-methylbenzofuran-3-carboxylic acid (1.20 g, 5.80 mmol) in DMF (29 mL) was added HATU (5.50 g, 14.0 mmol), p-toluidine (2.50 g, 23.0 mmol), and DIPEA (1.5 mL, 8.7 mmol). The brown solution was heated to 80° C. under argon. After 22 h, the reaction was cooled to room temperature, after which it was diluted with EtOAc and washed with NaHCO$_3$ (sat., aq). The aqueous layer was extracted 2× with EtOAc and the combined organic layers were washed successively with NH$_4$Cl (sat., aq.), brine, and H$_2$O (3×). It was then dried over Na$_2$SO$_4$, filtered and concentrated to give a brown oil. Flash column chromatography (5-30% EtOAc/hexanes) afforded a fraction of pure X in addition to a mixture of X and p-toluidine. The mixed fraction was repurified using the same conditions, and this process was repeated two additional times. In total 1.07 g (3.62 mmol, 62%) pure X was obtained as a tan solid. $R_f$=0.60 (25% EtOAc/hexanes). $^1$H NMR (CDCl3, 500 MHz) δ 7.63 (brs, 1H), 7.50 (d, J=8.4 Hz, 2H), 7.32 (d, J=8.9 Hz, 1H), 7.17 (d, J=8.2 Hz, 2H), 7.14 (d, J=2.5 Hz, 1H), 6.86 (dd, J=8.9, 2.5 Hz), 3.82 (s, 3H), 2.68 (s, 3H), 2.35 (s, 3H); $^{13}$C NMR (CDCl$_3$, 125 MHz) δ 162.4, 160.6, 156.6, 148.6, 135.3, 134.3, 129.7, 126.3, 120.4, 112.7, 112.3, 111.8, 102.7, 56.0, 21.0, 14.2; HRMS (ESI) calculated for C$_{18}$H$_{18}$NO$_3$ (MH$^+$) 296.1281, observed 296.1285.

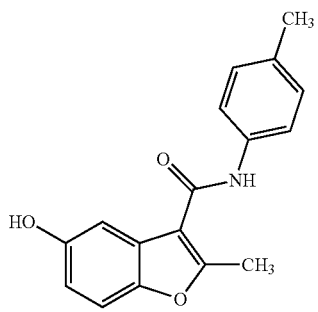 [SMILES: Cc1ccc(NC(=O)c2c(C)oc3ccc(O)cc23)cc1]

Compound 14

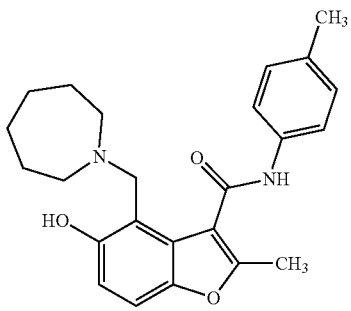

Compound 1

A solution of X (703 mg, 2.38 mmol) in DCM (60 mL) was cooled to −78° C. Then BBr$_3$ (1M in DCM, 11.9 mL) was added slowly. The solution was allowed to gradually warm to room temperature overnight. After a total of 22 h ~60 mL 1N HCl added and the resulting mixture was stirred vigorously for 45 min. At this point, the DCM was removed in vacuo and the aqueous mixture was extracted two times with EtOAc. The combined organic layers were washed with NaHCO$_3$ (sat., aq) followed by brine. It was then dried over Na$_2$SO$_4$, filtered, and concentrated to give a yellow solid. Flash column chromatography (0-15% MeOH/DCM) afforded X (189 mg, 28%) as a tan solid. R$_f$=0.32 (5% MeOH/DCM); $^1$H NMR (CD$_3$OD, 500 MHz) δ 7.53 (d, J=8.3 Hz, 2H), 7.27 (d, J=8.8 Hz, 1H), 7.17 (d, J=8.3 Hz, 2H), 7.10 (d, J=2.4 Hz, 1H), 6.76 (dd, J=8.8, 2.5 Hz, 1H), 2.62 (s, 3H), 2.33 (s, 3H); $^{13}$C NMR (CD$_3$OD, 125 MHz) δ 165.1, 160.0, 155.0, 149.5, 137.1, 135.3, 130.3, 128.3, 122.0, 114.5, 113.9, 112.1, 106.1, 21.0, 13.9; HRMS (ESI) calculated for C$_{17}$H$_{16}$NO$_3$ (MH$^+$) 282.1125, observed 282.1124.

Stability Study

Compound 1 (10 µL of 1 mM DMSO solution) was added to 490 µL RPMI-1640 culture media. After 1 min, 25 h, 48 h, and 72 h, 100 µL of this solution was diluted into 100 µL acetonitrile. The mixture was centrifuged at 5500 rpm for 1 min and the supernatant was removed from the pellet. Another 800 µL MeCN was added to the supernatant and the mixture was centrifuged again at 5500 rpm for 1 min. The resulting supernatant was subjected to LC/MS (ESI$^+$) on an Agilent Technologies 1200 LC/MSD single quadrupole system, equipped with an in-line diode-array UV detector. The mass corresponding to Compound 1 (M+H$^+$=393) was extracted and the chromatogram evaluated. This mass persisted as a significant peak through 72 h. Masses of the putative hydrolyzed compound (compound 26, see structure below; M+H$^+$=312) and o-quinone methide compound (see structure below; M+H$^+$=294) were extracted, and were found to be insignificant at all time points.

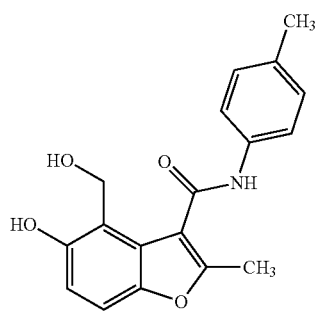

Hydrolyzed Compound

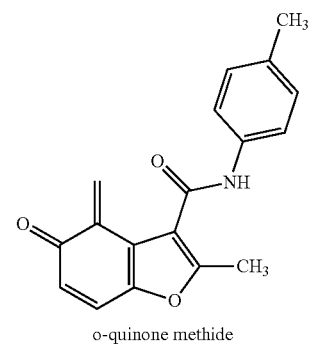

o-quinone methide

Example 2

Exemplary Analogs of Compound 1

Figure 10:
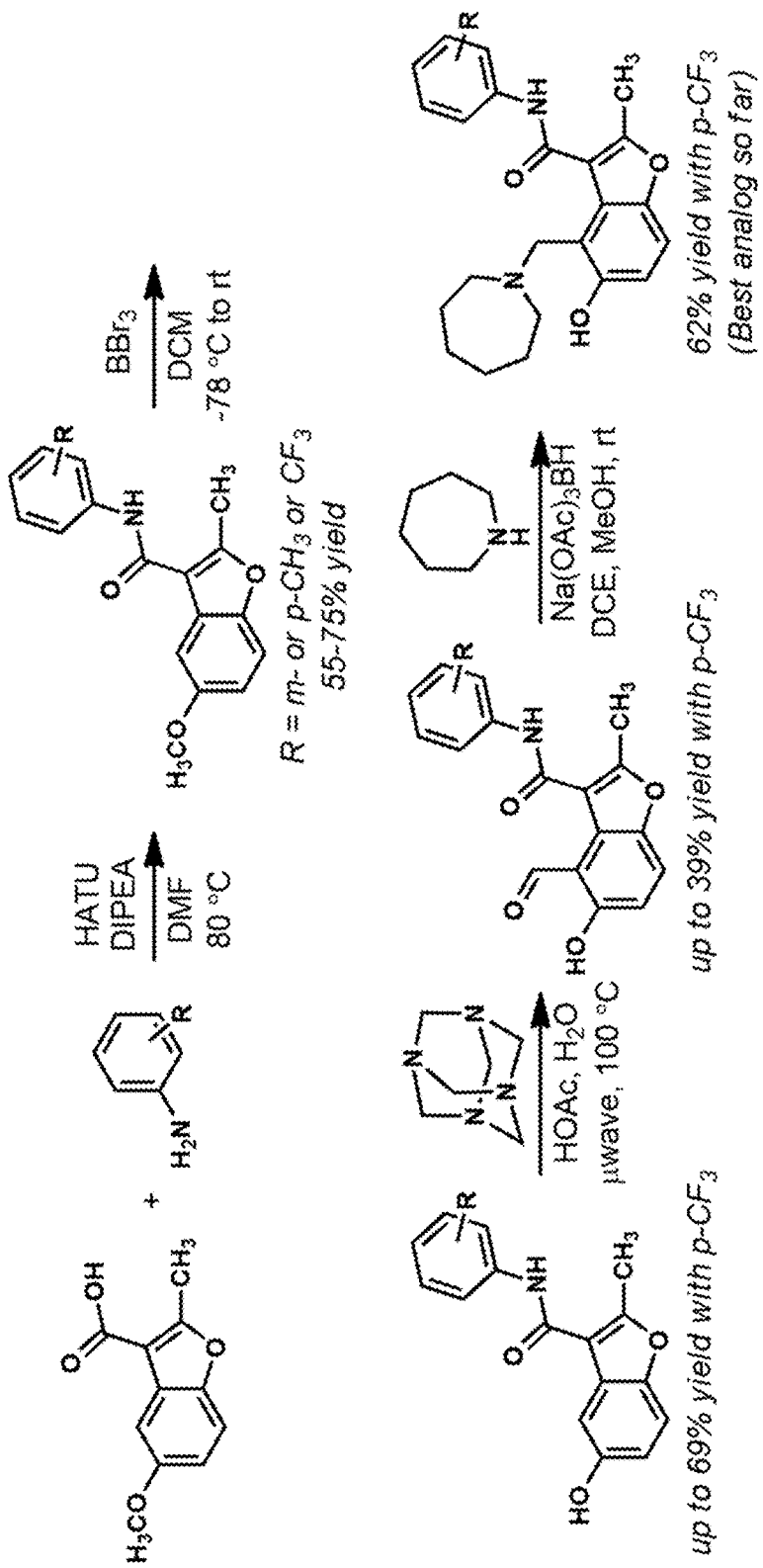
FIG. 10 shows a general scheme for synthesis of analogs of Compound 1.
Figure 11:
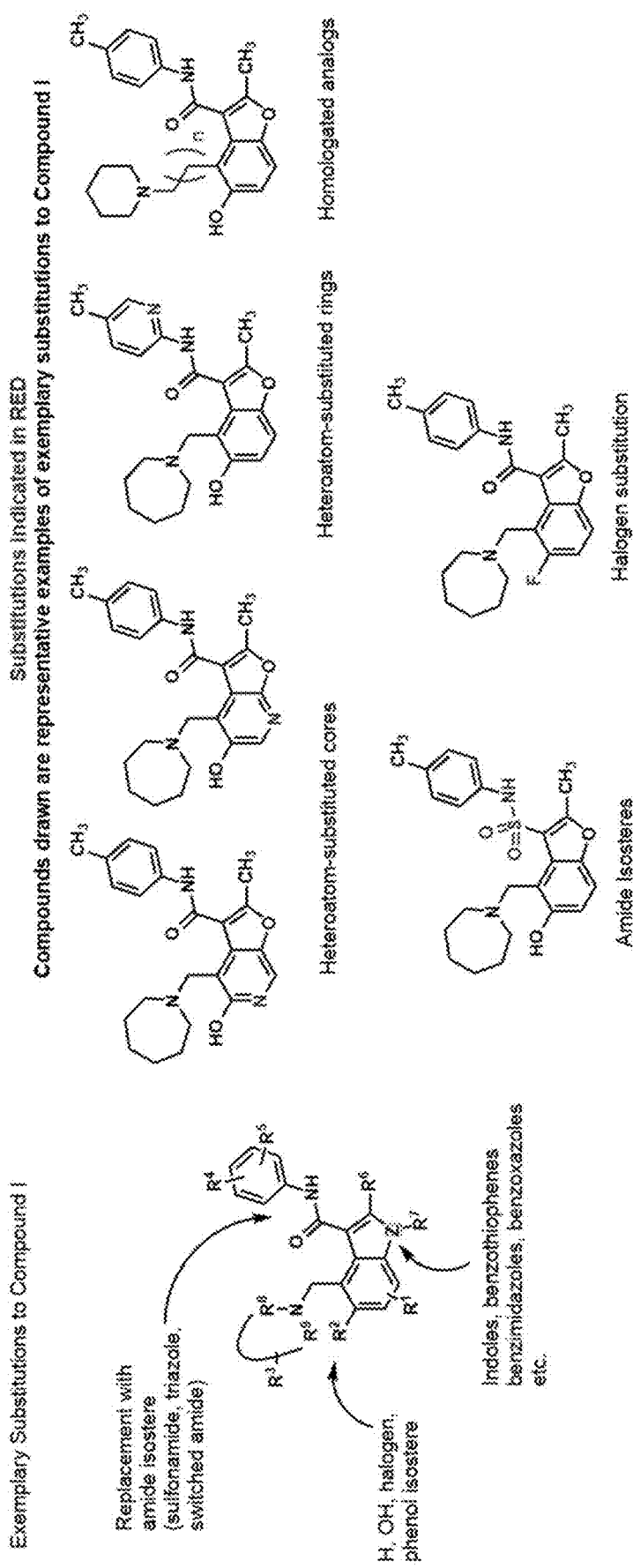
FIG. 11 illustrates exemplary substitutions to Compound 1 that can be made to generate analogs that stabilize the G4 in the c-MYC promoter and inhibit c-Myc expression.

FIG. 11 shows exemplary substitutions to Compound 1 that can be made to generate analogs of Compound 1 that selectively bind to G4 quadruplex DNA comprising the sequence set forth as SEQ ID NO: 2, and can be used to reduce c-MYC expression in cells. FIG. 10 illustrates an exemplary procedure for generating analogs of Compound 1. The amine group of Compound 1 can be varied in reductive aminations to provide additional analogs. Several exemplary analogs of Compound 1 are listed in the following table, which also shows results of assays for inhibition of c-MYC expression in L363 cells (Peggy) and for viability of L363 cells as discussed in Example 1. The table also provides an indication of an exemplary commercial source for the compounds, or (if applicable) an indication that the compound is new.

| Compound No. | Structure | Name/Catalog No. | Peggy (% c-Myc expression compared to untreated) | IC$_{50}$ |
| --- | --- | --- | --- | --- |
| 1 | 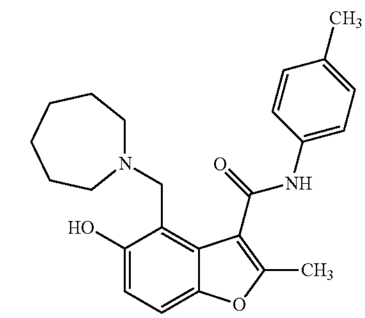 [SMILES: Cc1ccc(NC(=O)c2c(C)oc3ccc(O)c(CN4CCCCCC4)c23)cc1] | Commercial: ChemDiv No. D089-0563 | 50% (at 10 μM) | 7.6 μM |
| 2 | 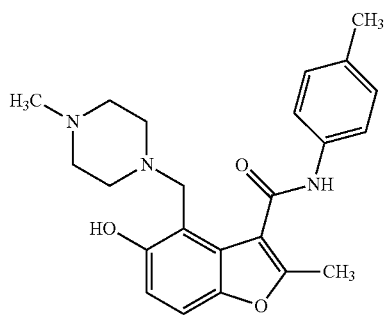 [SMILES: Cc1ccc(NC(=O)c2c(C)oc3ccc(O)c(CN4CCN(C)CC4)c23)cc1] | Commercial: ChemDiv No. D089-0474 | 72% (at 10 μM) | 95% viability (at 10 μM) |
| 3 | 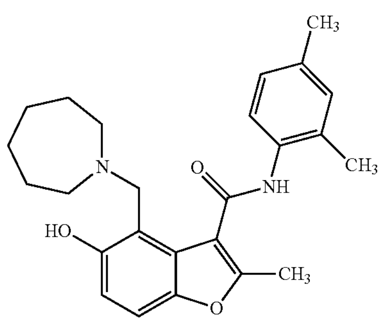 [SMILES: Cc1ccc(NC(=O)c2c(C)oc3ccc(O)c(CN4CCCCCC4)c23)c(C)c1] | Commercial: Otava Chemical No. 7018860541 | 52% (at 10 μM) | 6.3 μM |
| 4 | 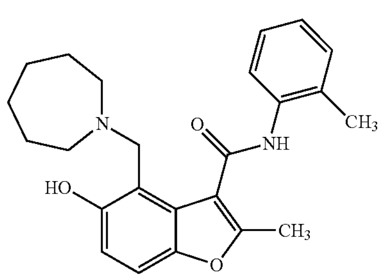 [SMILES: Cc1ccccc1NC(=O)c1c(C)oc2ccc(O)c(CN3CCCCCC3)c12] | Commercial: ChemDiv No. D089-0559 | 73% (at 10 μM) | 75% viability (at 10 μM) |
| 5 | 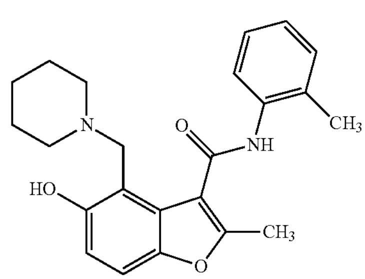 [SMILES: Cc1ccccc1NC(=O)c1c(C)oc2ccc(O)c(CN3CCCCC3)c12] | Commercial: ChemBridge No. 9127171 | 89% (at 10 μM) | 85% viability (at 10 μM) |

-continued

| Compound No. | Structure | Name/Catalog No. | Peggy (% c-Myc expression compared to untreated) | $IC_{50}$ |
|---|---|---|---|---|
| 6 | 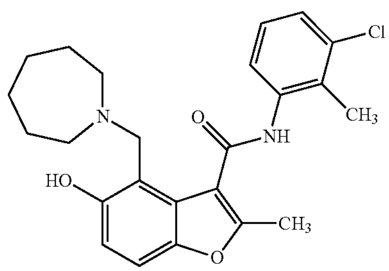 [SMILES: Cc1oc2ccc(O)c(CN3CCCCCC3)c2c1C(=O)Nc1cccc(Cl)c1C] | Commercial: Otava Chemical No. 7018860559 | 45% (at 10 μM) | 4.9 μM |
| 7 | 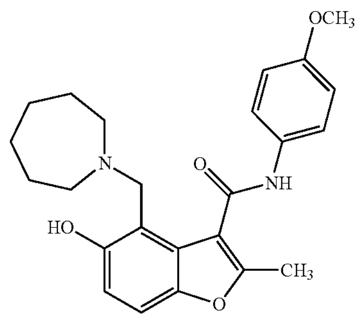 [SMILES: COc1ccc(NC(=O)c2c(C)oc3ccc(O)c(CN4CCCCCC4)c23)cc1] | Commercial: Otava Chemical No. 7018860542 | 81% (at 10 μM) | 7.2 μM |
| 8 | 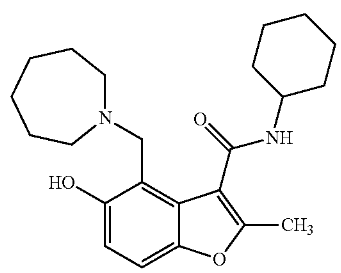 [SMILES: Cc1oc2ccc(O)c(CN3CCCCCC3)c2c1C(=O)NC1CCCCC1] | Commercial: Otava Chemical No. 7018860556 | 76% (at 10 μM) | — |
| 9 | 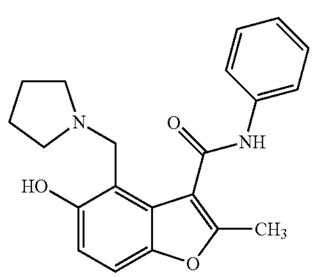 [SMILES: Cc1oc2ccc(O)c(CN3CCCC3)c2c1C(=O)Nc1ccccc1] | Commercial: ChemBridge No. 9139363 | 96% (at 10 μM) | 100% viability (at 10 μM) |
| 10 | 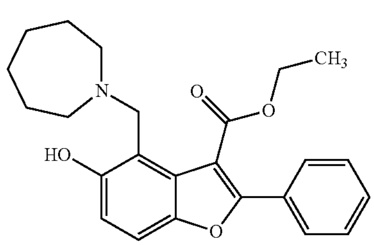 [SMILES: CCOC(=O)c1c(-c2ccccc2)oc2ccc(O)c(CN3CCCCCC3)c12] | Commercial: ChemBridge No. 6240697 | 37% (at 10 μM) | 7.1 μM |

| Compound No. | Structure | Name/Catalog No. | Peggy (% c-Myc expression compared to untreated) | IC$_{50}$ |
|---|---|---|---|---|
| 11 | 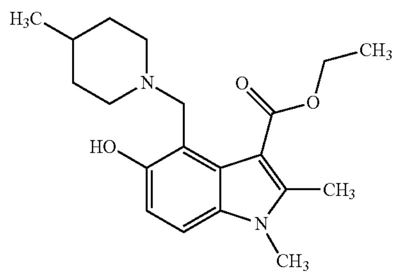 [SMILES: CCOC(=O)c1c(C)n(C)c2ccc(O)c(CN3CCC(C)CC3)c12] | Commercial: ChemBridge No. 6238398 | 69% (at 10 μM) | 89% viability (at 10 μM) |
| 12 | 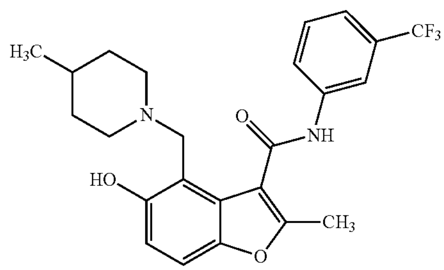 [SMILES: Cc1oc2ccc(O)c(CN3CCC(C)CC3)c2c1C(=O)Nc1cccc(C(F)(F)F)c1] | Commercial: ChemDiv No. D089-0350 | 43% (at 10 μM) | 3.4 μM |
| 13 | 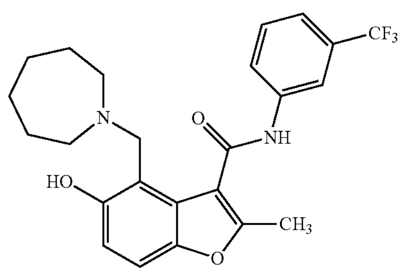 [SMILES: Cc1oc2ccc(O)c(CN3CCCCCC3)c2c1C(=O)Nc1cccc(C(F)(F)F)c1] | Commercial: Otava Chemical No. 7018860553 | 12% (at 10 μM) | 3.3 μM |
| 14 | 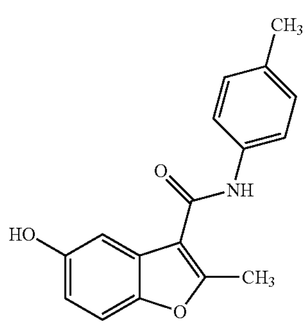 [SMILES: Cc1ccc(NC(=O)c2c(C)oc3ccc(O)cc23)cc1] | New: 196D-12 | 106% (at 10 μM) | 84% viability (at 10 μM) |
| 15 | 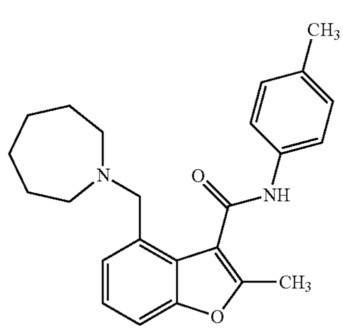 [SMILES: Cc1ccc(NC(=O)c2c(C)oc3cccc(CN4CCCCCC4)c23)cc1] | New: 196D-15 | 80% (at 10 μM) | 53% viability (at 10 μM) |

-continued

| Compound No. | Structure | Name/Catalog No. | Peggy (% c-Myc expression compared to untreated) | IC$_{50}$ |
| --- | --- | --- | --- | --- |
| 16 | 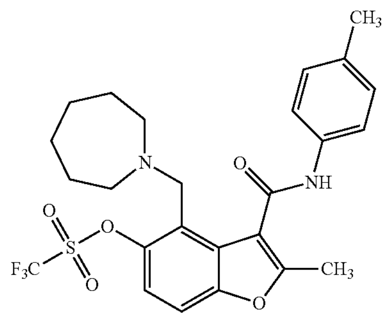 [SMILES: Cc1ccc(NC(=O)c2c(C)oc3ccc(OS(=O)(=O)C(F)(F)F)c(CN4CCCCCC4)c23)cc1] | New: 196D-16 | 112% (at 10 μM) | 70% viability (at 10 μM) |
| 17 | 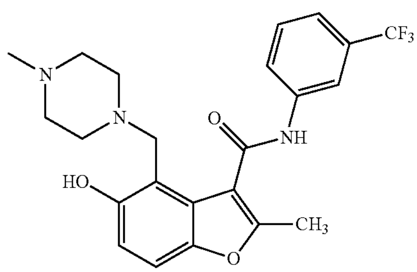 [SMILES: Cc1oc2ccc(O)c(CN3CCN(C)CC3)c2c1C(=O)Nc1cccc(C(F)(F)F)c1] | Commercial: Otava Chemical No. 7018860464 | 68% (at 10 μM) | >12 μM |
| 18 | 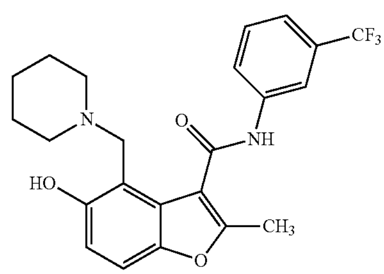 [SMILES: Cc1oc2ccc(O)c(CN3CCCCC3)c2c1C(=O)Nc1cccc(C(F)(F)F)c1] | Commercial: Otava Chemical No. 7018860259 | 6.5% (at 10 μM) | 5.2 μM |
| 19 | 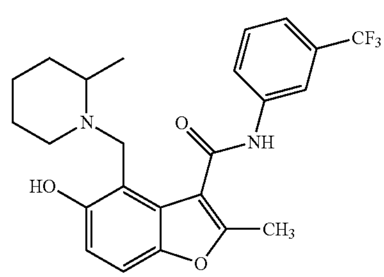 [SMILES: Cc1oc2ccc(O)c(CN3CCCCC3C)c2c1C(=O)Nc1cccc(C(F)(F)F)c1] | Commercial: Otava Chemical No. 7018860288 | 0.56% (at 10 μM) | 3.8 μM |
| 20 | 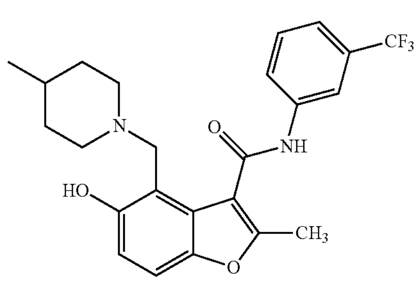 [SMILES: Cc1oc2ccc(O)c(CN3CCC(C)CC3)c2c1C(=O)Nc1cccc(C(F)(F)F)c1] | Commercial: Otava Chemical No. 7018860345 | 1.4% (at 10 μM) | 3.8 μM |

-continued

| Compound No. | Structure | Name/Catalog No. | Peggy (% c-Myc expression compared to untreated) | IC$_{50}$ |
|---|---|---|---|---|
| 21 | 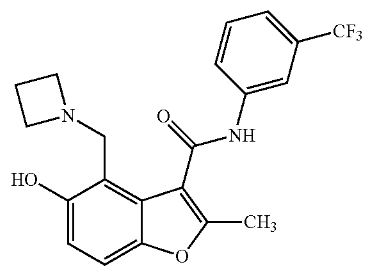 [SMILES: Cc1oc2ccc(O)c(CN3CCC3)c2c1C(=O)Nc1cccc(C(F)(F)F)c1] | New: 196D-44 | 74% (at 10 μM) | >12 μM |
| 22 | 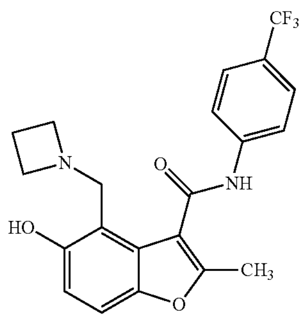 [SMILES: Cc1oc2ccc(O)c(CN3CCC3)c2c1C(=O)Nc1ccc(C(F)(F)F)cc1] | New: 196D-48b | 27% (at 10 μM) | 100% viability (at 10 μM) |
| 23 | 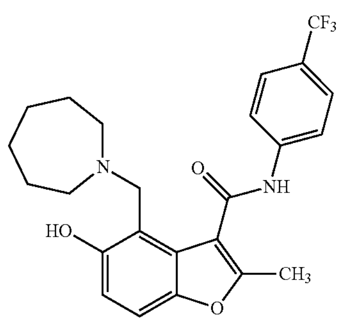 [SMILES: Cc1oc2ccc(O)c(CN3CCCCCC3)c2c1C(=O)Nc1ccc(C(F)(F)F)cc1] | New: DC-34 | 0.44% (at 10 μM) | 3.6 μM |
| 24 | 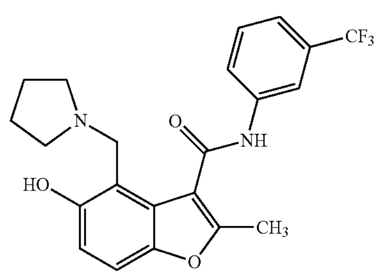 [SMILES: Cc1oc2ccc(O)c(CN3CCCC3)c2c1C(=O)Nc1cccc(C(F)(F)F)c1] | New: 196D-49a | 63% (at 6 μM) | 7.8 μM |
| 25 | 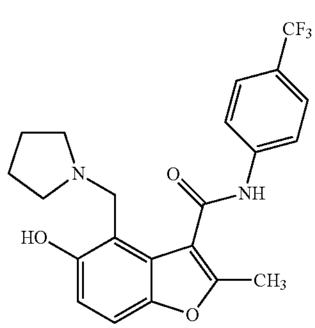 [SMILES: Cc1oc2ccc(O)c(CN3CCCC3)c2c1C(=O)Nc1ccc(C(F)(F)F)cc1] | New: 196D-49b | 32% (at 10 μM) | 1.6 μM |

-continued

| Compound No. | Structure | Name/Catalog No. | Peggy (% c-Myc expression compared to untreated) | IC$_{50}$ |
|---|---|---|---|---|
| 26 | (4-methylpiperidin-1-yl)methyl, 5-hydroxy, 2-methyl benzofuran-3-carboxamide with N-(4-trifluoromethylphenyl) | New: DC-065B | — | 11.40 μM |
| 27 | (2-methylpiperidin-1-yl)methyl, 5-hydroxy, 2-methyl benzofuran-3-carboxamide with N-(4-trifluoromethylphenyl) | New: DC-066B | — | 25.84 μM |
| 28 | (2-methylpyrrolidin-1-yl)methyl, 5-hydroxy, 2-methyl benzofuran-3-carboxamide with N-(4-trifluoromethylphenyl) | New: DC-067B | — | 6.84 μM |
| 29 | (2-methylpyrrolidin-1-yl)methyl, 5-hydroxy, 2-methyl benzofuran-3-carboxamide with N-(4-trifluoromethylphenyl) | New: DC-068B | — | 4.45 μM |

-continued

| Compound No. | Structure | Name/Catalog No. | Peggy (% c-Myc expression compared to untreated) | IC$_{50}$ |
|---|---|---|---|---|
| 30 | 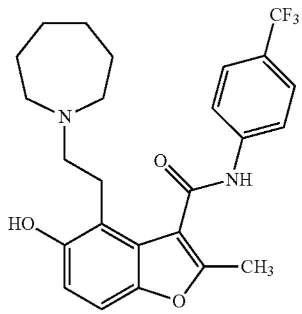 [SMILES: Cc1oc2ccc(O)c(CCN3CCCCCC3)c2c1C(=O)Nc1ccc(C(F)(F)F)cc1] | New: DC-069B | — | 38.17 μM |
| 31 | 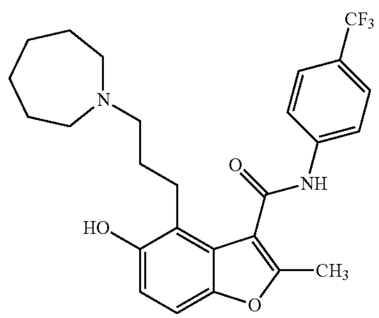 [SMILES: Cc1oc2ccc(O)c(CCCN3CCCCCC3)c2c1C(=O)Nc1ccc(C(F)(F)F)cc1] | New: DC-197 | — | 100% viability (at 10 μM) |
| 32 | 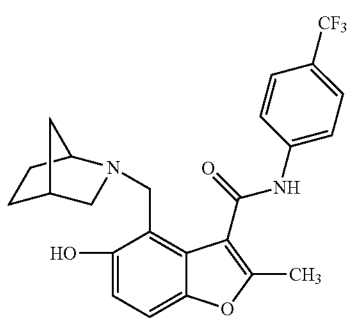 [SMILES: Cc1oc2ccc(O)c(CN3CC4CCC3C4)c2c1C(=O)Nc1ccc(C(F)(F)F)cc1] | New: DC-111B | — | 100% viability (at 10 μM) |
| 33 | 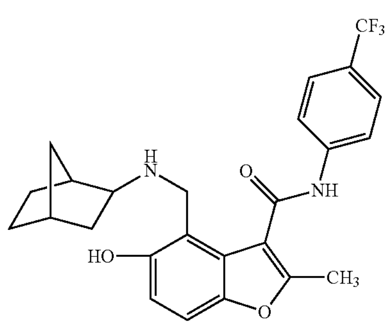 [SMILES: Cc1oc2ccc(O)c(CNC3CC4CCC3C4)c2c1C(=O)Nc1ccc(C(F)(F)F)cc1] | New: DC-86B | — | 100% viability (at 10 μM) |

-continued
| Compound No. | Structure | Name/Catalog No. | Peggy (% c-Myc expression compared to untreated) | IC$_{50}$ |
|---|---|---|---|---|
| 34 | 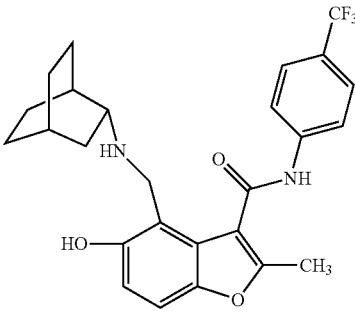 [SMILES: Cc1oc2ccc(O)c(CNC3CC4CCC3CC4)c2c1C(=O)Nc1ccc(C(F)(F)F)cc1] | New: DC-102B | — | 9.83 μM |
| 35 | 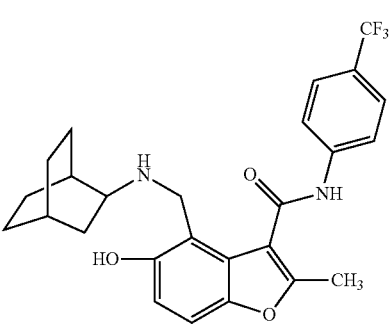 [SMILES: Cc1oc2ccc(O)c(CNC3CC4CCC3CC4)c2c1C(=O)Nc1ccc(C(F)(F)F)cc1] | New: DC-103B | — | 100% viability (at 10 μM) |
Additional analogs of Compound 1 are listed below:
| Compound | Structure |
|---|---|
| 36 | 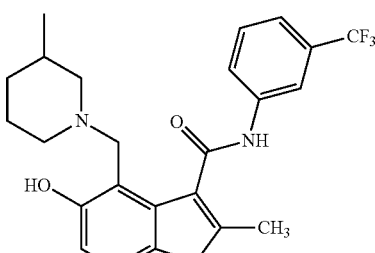 |
| 37 | 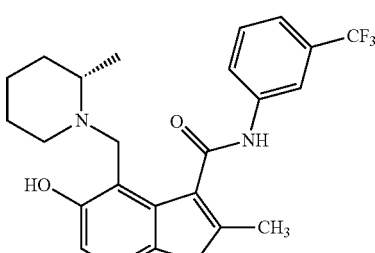 |};
-continued
| Compound | Structure |
|---|---|
| 38 | 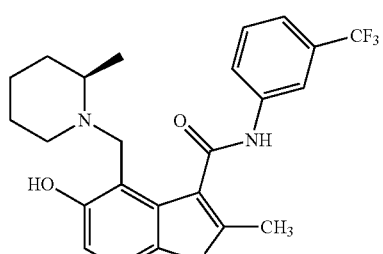 |
| 39 | 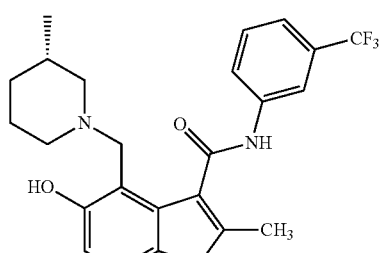 |

| Compound | Structure |
|---|---|
| 40 | (structure: 3-methylpiperidine-CH2 attached to benzofuran with HO, CH3, C(O)NH-Ar(CF3)) |
| 41 | (structure: 4-ethylpiperazine-CH2 attached to benzofuran with HO, CH3, C(O)NH-Ar(CF3)) |
| 42 | (structure: 4-benzylpiperazine-CH2 attached to benzofuran with HO, CH3, C(O)NH-Ar(CF3)) |
| 43 | (structure: morpholine-CH2 attached to benzofuran with HO, CH3, C(O)NH-Ar(CF3)) |

Additional multiple myeloma cell lines were assayed for cell viability in the presence of Compound 23, and the following IC50 values were determined.

| Cell Line | IC$_{50}$ (µM) |
|---|---|
| L363 | 3.64 |
| KMM1 | 4.13 |
| KMS27 | 5.06 |
| KMS12PE | 5.33 |
| ARD | 5.75 |
| AMO1 | 5.92 |
| JIM1 | 6.35 |

Example 3

Compounds 1 and 23 Reduce Growth of c-Myc Expressing Cells

This example illustrates that Compounds 1 and 23 can be used in inhibit the growth of c-Myc expressing cancer cell lines in vitro. The NCI-60 panel of cancer cell lines (see Shoemaker, Nat. Rev. Cancer, 6, 813-823, 2006, and dtp-.cancer.gov/discovery_development/nci-60/) was assayed for cell growth in the presence of 10 µM Compound 1 or Compound 23 for 48 hours. At 48 hours, the assay was terminated by fixation with TCA and determination of relative cell counts by addition of Sulforhodamine B (SRB, see Alley et al., Cancer Research, 48: 589-601, 1988.). Growth percent was determined by comparison of SRB reading of a duplicate plate of cells taken at the time of compound addition to the SRB reading at the termination of the treatment. The following table provides a summary of the percent of growth of each cell line in the panel compared to control (no treatment), as well as the mean delta and range of percent growth compared to control across the panel of cell lines for each treatment condition.

| Cell Line | Compound 1 Growth Percent | Compound 23 Growth Percent |
|---|---|---|
| Leukemia | | |
| CCRF-CEM | 87.67 | 65.23 |
| HL-60(TB) | 92.74 | 83.01 |
| K-562 | 75.93 | 29.63 |
| MOLT-4 | 92.81 | 64.31 |
| RPMI-8226 | 91.38 | 75.08 |
| SR | 83.12 | −8.44 |
| Non-Small Cell Lung Cancer | | |
| A549/ATCC | 85.87 | 61.22 |
| EKVX | 83.79 | 64.06 |
| HOP-62 | 79.76 | 70.39 |
| HOP-92 | 55.89 | 34.88 |
| NCI-H226 | 85.66 | 72.45 |
| NCI-H23 | 90.23 | 69.93 |
| NCI-H322M | 97.51 | 69.34 |
| NCI-H460 | 80.25 | 51.53 |
| NCI-H522 | 90.68 | 72.52 |
| Colon Cancer | | |
| COLO 205 | 104.20 | 48.73 |
| HCC-2998 | 116.36 | 11.22 |
| HCT-116 | 64.67 | 32.68 |
| HCT-15 | 83.45 | 45.06 |
| HT29 | 100.25 | 80.45 |
| KM12 | 102.59 | 65.50 |
| SW-620 | 85.97 | 67.44 |
| CNS Cancer | | |
| SF-268 | 100.73 | 75.44 |
| SF-295 | 85.34 | 48.84 |
| SF-539 | 93.10 | 61.23 |
| SNB-19 | 84.35 | 69.94 |
| SNB-75 | 78.34 | 50.57 |
| U251 | 88.66 | 55.07 |
| Melanoma | | |
| LOX IMVI | 88.87 | 39.15 |
| MALME-3M | 107.60 | 49.92 |
| M14 | 85.90 | 58.14 |
| MDA-MB-435 | 95.94 | 58.22 |
| SK-MEL-2 | 99.26 | 78.38 |
| SK-MEL-28 | 96.60 | 76.90 |
| SK-MEL-5 | 86.08 | 69.97 |
| UACC-257 | 112.11 | 82.00 |
| UACC-62 | 102.82 | 67.27 |

-continued

| Cell Line | Compound 1 Growth Percent | Compound 23 Growth Percent |
|---|---|---|
| Ovarian Cancer | | |
| IGROV1 | 81.22 | 54.25 |
| OVCAR-3 | 101.03 | 62.02 |
| OVCAR-4 | 82.06 | 58.58 |
| OVCAR-5 | 95.63 | 85.79 |
| OVCAR-8 | 89.96 | 66.34 |
| NCI/ADR-RES | 89.34 | 53.65 |
| SK-OV-3 | 100.26 | 76.35 |
| Renal Cancer | | |
| 786-0 | 84.68 | 49.50 |
| A498 | 64.12 | 50.48 |
| ACHN | 93.94 | 68.48 |
| CAKI-1 | 75.13 | 50.46 |
| RXF 393 | 81.36 | 50.40 |
| SN12C | 84.31 | 66.72 |
| TK-10 | 92.66 | 81.06 |
| UO-31 | 62.74 | 40.69 |
| Prostate Cancer | | |
| PC-3 | 79.90 | 45.70 |
| DU-145 | 103.26 | 64.80 |
| Breast Cancer | | |
| MCF7 | 78.41 | 48.09 |
| MDA-MB-231/ATCC | 79.39 | 48.96 |
| HS 578T | 88.40 | 65.50 |
| BT-549 | 92.88 | 78.51 |
| T-47D | 92.74 | 73.98 |
| MDA-MB-468 | 73.62 | 5.74 |
| Mean | 88.39 | 58.56 |
| Delta | 32.50 | 67.00 |
| Range | 60.47 | 94.23 |

The effect of Compound 23 on the expression of c-Myc protein in the human lung cancer cell lines H1299 and H157 was also assayed. H1299 and H157 cells were treated with 10 µM Compound 23 and c-Myc protein expression levels quantified by Western blot. In Compound 23-treated H1299 cells, c-Myc protein expression levels were approximately 55% compared to untreated control cells. In Compound 23-treated H157 cells, c-Myc protein expression levels were approximately 74% compared to untreated control cells.

Example 4

Pharmacokinetic Evaluation of Compound 23

Figure 12:
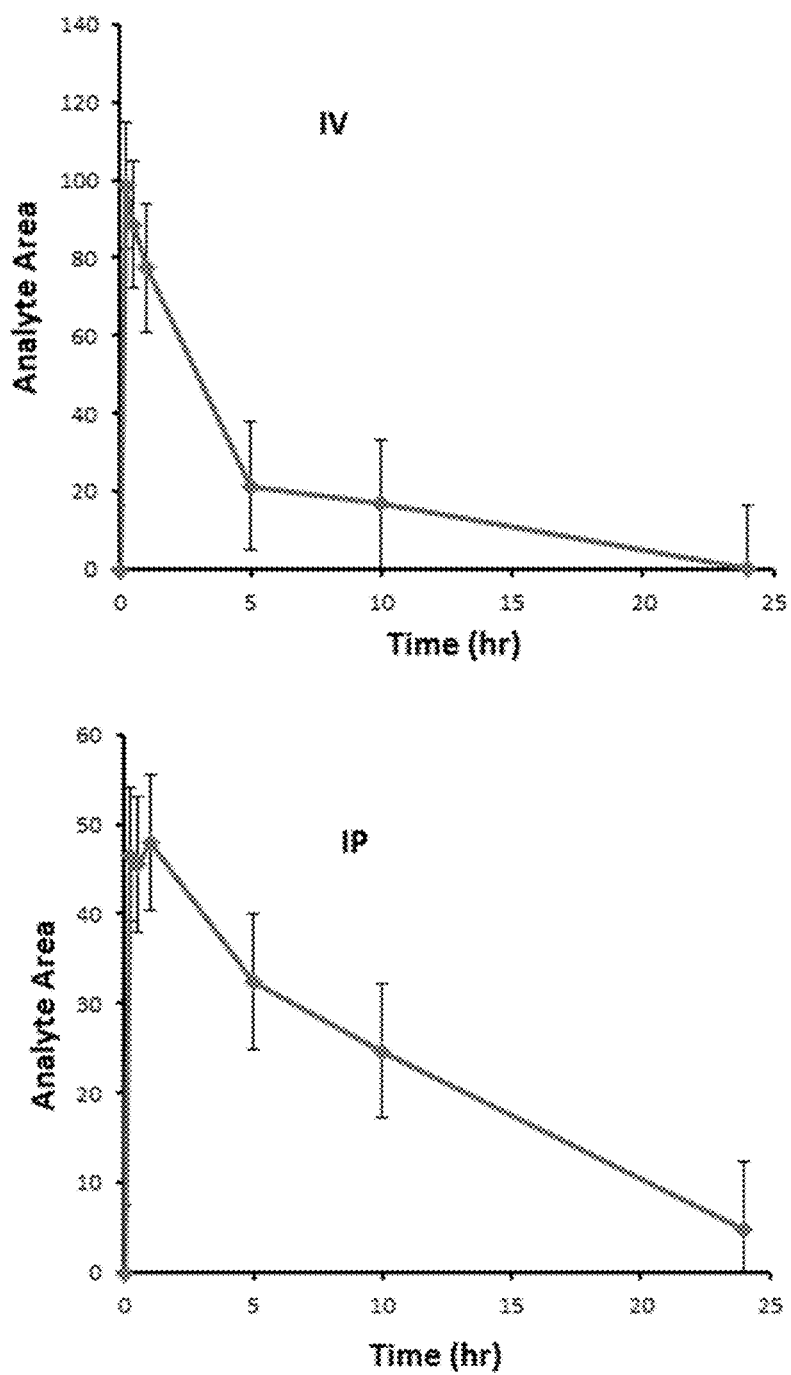
FIG. 12 is a set of graphs showing the blood plasma levels of Compound 23 after a single IP (lower graph) or IV (upper graph) injection (19 mg/kg) in female nude mice.

The blood plasma levels of Compound 23 after a single IP or IV injection (19 mg/kg) in female nude mice were determined by mass spectrometry (see FIG. 12 and the following table).

| Pharmacokinetic Parameters | IV | IP |
|---|---|---|
| $AUC_{0-24\,h}$ | 491.729 | 552.478 |
| $AUC_{0-inf}$ | 493.342 | 570.140 |
| $T_{max}$ (h) | 0.38 | 1.00 |
| $t_{1/2}$ (h) | 2.25 | 6.50 |
| Kel (1/h) | 0.277 | 0.277 |

Example 5

Pharmacodynamic Evaluation of Compound 23

Figure 13:
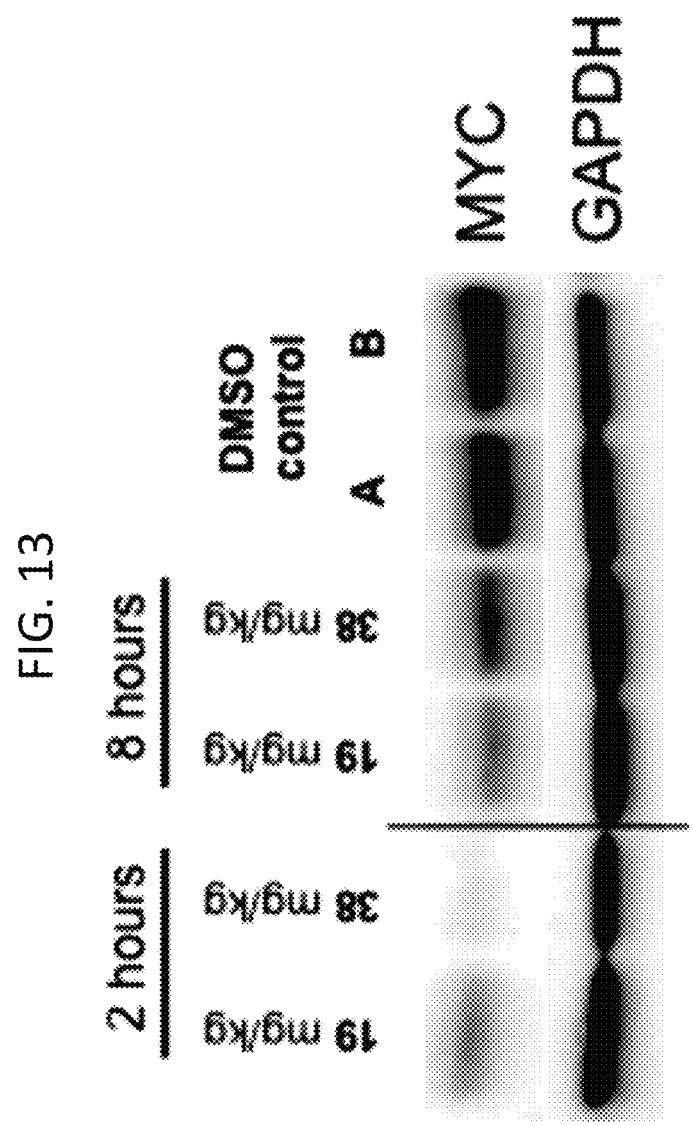
FIG. 13 shows a Western blot showing c-MYC expression levels in L363 subcutaneous xenografts that were harvested from xenograft bearing mice 2 or 8 hours after a single dose of Compound 23 at 19 mg/kg or 38 mg/kg (administered IP).

The capacity of Compound 23 to inhibit c-MYC expression in tumor was evaluated in nude mice bearing subcutaneous xenografts of the human multiple myeloma cell line L363. In this assay, tumors from two tumor-bearing mice were harvested 2 and 8 hours after a single dose of Compound 23 at 19 mg/kg or 38 mg/kg (administered IP). By western blot, decreased c-MYC expression levels were observed in tumors at each time point compared to vehicle control tumors (FIG. 13).

It will be apparent that the precise details of the methods or compositions described may be varied or modified without departing from the spirit of the described embodiments. We claim all such modifications and variations that fall within the scope and spirit of the claims below.

We claim:

1. A method of treating cancer in a subject, comprising administering to the subject a therapeutically effective amount of a compound, or a pharmaceutically acceptable salt thereof, having a structure of:

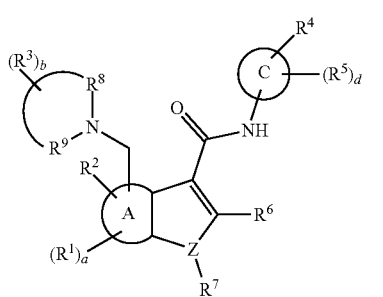

Formula II wherein:
- A is a 6 membered aryl ring;
- C is a 6-membered aryl ring;
- each $R^1$ is independently selected from hydrogen or optionally-substituted lower alkyl;
- a is 0, 1, or 2;
- $R^2$ is selected from hydroxyl or halogen;
- $R^8$ and $R^9$ together with the linking nitrogen atom form a 4 to 7 membered optionally-substituted N-hetero-mono- or bi-cyclic ring with one or two hetero atoms independently selected from nitrogen and oxygen;
- each $R^3$ is independently selected from halogen, lower haloalkyl, or optionally-substituted lower alkyl;
- b is 0 to 4;
- $R^4$ is selected from halogen, lower haloalkyl, or optionally-substituted lower alkyl;
- each $R^5$ is independently selected from halogen, lower haloalkyl, or optionally-substituted lower alkyl;
- d is 0, 1, or 2;
- $R^6$ is selected from methyl, trifluoromethyl, or phenyl;
- Z is selected from nitrogen or oxygen;
- if Z is nitrogen, $R^7$ is selected from hydrogen, halogen, lower haloalkyl, or optionally-substituted lower alkyl, and if Z is oxygen, $R^7$ is not present; and
- wherein each substituted lower alkyl and substituted N-hetero- mono- or bi-cyclic ring is independently selected from a lower alkyl or N-hetero- mono- or bi-cyclic ring wherein one or more hydrogen atoms are replaced with $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, $C_{1-6}$alkylhalo, $C_{1-6}$alkoxyhalo, carboxyl, cyano, nitro, amino, acyl, amido, aminoacyl, mercapto, alkylthio, thioxo, sulfates, sulfonates, sulfinyl, sulfonyl, sulfonylamido, aryl, $arC_{1-6}$alkyl, heterocyclyl, heteroaryl, or halogen; and
- wherein the compound does not have the structure of Compound 1:

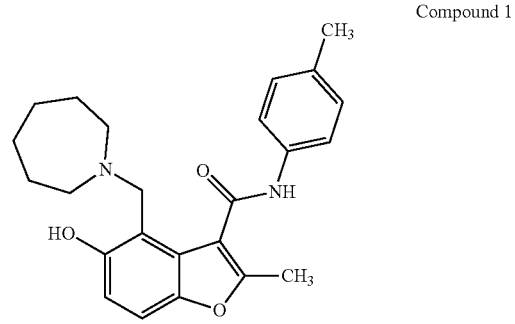

Compound 1 and wherein the cancer is a small cell lung cancer, a ductal carcinoma, a colon carcinoma, a renal carcinoma, an adenocarcinoma, a sarcoma, or an osteogenic sarcoma.

2. The method of claim 1, wherein Z is oxygen and $R^7$ is not present.

3. The method of claim 1, wherein Z is nitrogen and $R^7$ is selected from hydrogen, hydroxyl, halogen, lower haloalkyl, optionally-substituted lower alkoxy, or is not present.

4. The method of claim 1, wherein a is 0, $R^2$ is hydroxyl, and/or $R^6$ is methyl.

5. The method of claim 1, wherein $R^4$ is lower haloalkyl.

6. The method of claim 1, wherein d is 0.

7. The method of claim 1, wherein $R^2$ is hydroxyl, $R^6$ is methyl, and a is 0.

8. The method of claim 1, wherein $R^8$ and $R^9$ together with the linking nitrogen atom form optionally-substituted pyrrolidine, optionally-substituted imidizolidine, optionally-substituted pryazolidine, optionally-substituted piperidine, optionally-substituted piperazine, or optionally-substituted azepane.

9. The method of claim 8, wherein $R^8$ and $R^9$ together with the linking nitrogen atom form pyrrolidine, imidizolidine, pryazolidine, piperidine, piperazine, or azepane.

10. The method of claim 9, wherein $R^8$ and $R^9$ together with the linking nitrogen atom form piperidine or azepane.

11. The method of claim 1, wherein the compound has a structure of Formula III:

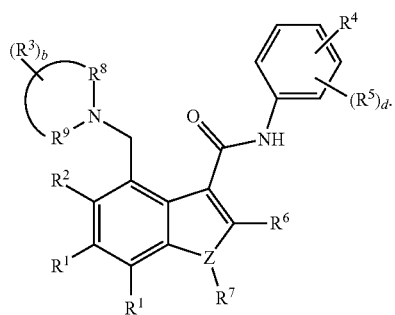

Formula III

12. The method of claim 1, wherein the compound has a structure of Formula IV or Formula V:

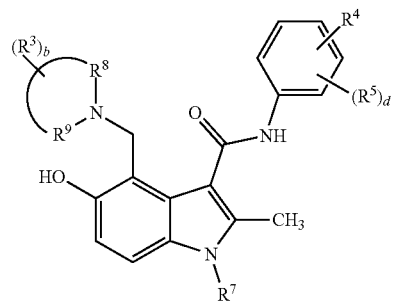

Formula IV

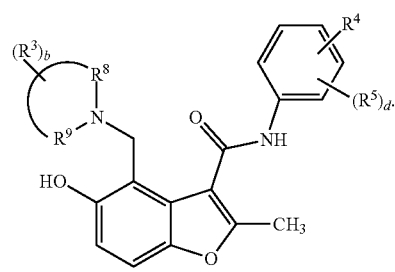

Formula V

13. The method of claim 1, wherein the compound is one of:

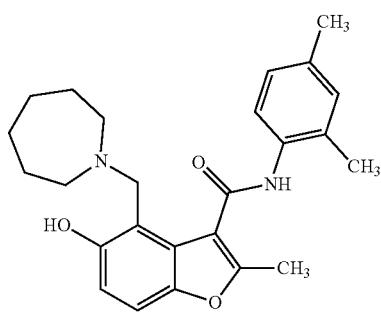

Compound 3

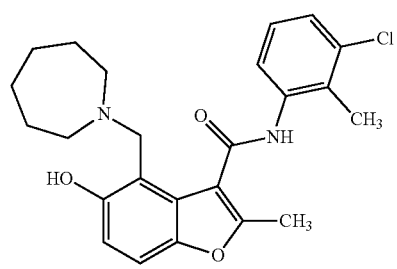

Compound 6

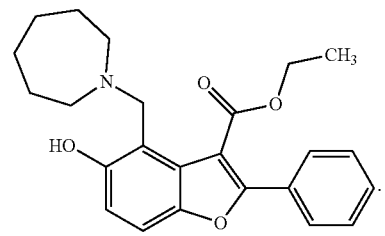

Compound 10

14. A method of treating cancer in a subject, comprising administering to the subject a therapeutically effective amount of a compound, or a pharmaceutically acceptable salt thereof, having a structure of:

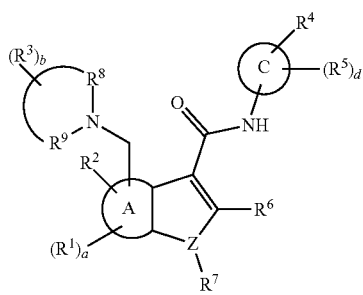

Formula II wherein:
A is a 6 membered aryl ring;
C is a 6-membered aryl ring;
each $R^1$ is independently selected from hydrogen or optionally-substituted lower alkyl;
a is 0, 1, or 2;
$R^2$ is selected from hydroxyl or halogen;
$R^8$ and $R^9$ together with the linking nitrogen atom form a 4 to 7 membered optionally-substituted N-heteromono- or bi-cyclic ring with one or two hetero atoms independently selected from nitrogen and oxygen;

each $R^3$ is independently selected from halogen, lower haloalkyl, or optionally-substituted lower alkyl;

b is 0 to 4;

wherein $R^4$ is trifluoromethyl;

each $R^5$ is independently selected from halogen, lower haloalkyl, or optionally-substituted lower alkyl;

d is 0, 1, or 2;

$R^6$ is selected from methyl, trifluoromethyl, or phenyl;

Z is selected from nitrogen or oxygen;

if Z is nitrogen, $R^7$ is selected from hydrogen, hydroxyl, halogen, lower haloalkyl, or optionally-substituted lower alkyl, and if Z is oxygen, $R^7$ is not present; and wherein each substituted lower alkyl and substituted N-hetero- mono- or bi-cyclic ring is independently selected from a lower alkyl or N-hetero- mono- or bi-cyclic ring wherein one or more hydrogen atoms are replaced with $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, $C_{1-6}$alkylhalo, $C_{1-6}$alkoxyhalo, carboxyl, cyano, nitro, amino, acyl, amido, aminoacyl, mercapto, alkylthio, thioxo, sulfates, sulfonates, sulfinyl, sulfonyl, sulfonylamido, aryl, $arC_{1-6}$alkyl, heterocyclyl, heteroaryl, or halogen;

and wherein the cancer is a small cell lung cancer, a ductal carcinoma, a colon carcinoma, a renal carcinoma, an adenocarcinoma, a sarcoma, or an osteogenic sarcoma.

15. The method of claim 14, wherein Z is oxygen and $R^7$ is not present.

16. The method of claim 14, wherein Z is nitrogen and $R^7$ is selected from hydrogen, hydroxyl, halogen, lower haloalkyl, optionally-substituted lower alkoxy, or is not present.

17. The method of claim 14, wherein a is 0, $R^2$ is hydroxyl, and/or $R^6$ is methyl.

18. The method of claim 14, wherein d is 0.

19. The method of claim 14, wherein $R^2$ is hydroxyl, $R^6$ is methyl, and a is 0.

20. The method of claim 14, wherein $R^2$ is hydroxyl, $R^6$ is methyl, a is 0, and d is 0.

21. The method of claim 14, wherein $R^8$ and $R^9$ together with the linking nitrogen atom form optionally-substituted pyrrolidine, optionally-substituted imidizolidine, optionally-substituted pryazolidine, optionally-substituted piperidine, optionally-substituted piperazine, or optionally-substituted azepane.

22. The method of claim 21, wherein $R^8$ and $R^9$ together with the linking nitrogen atom form pyrrolidine, imidizolidine, pryazolidine, piperidine, piperazine, or azepane.

23. The method of claim 22, wherein $R^8$ and $R^9$ together with the linking nitrogen atom form piperidine or azepane.

24. The method of claim 14, wherein the compound has a structure of any one of Formulas VI-IX:

Formula VI

Formula VII

Formula VIII

Formula IX

25. The method of claim 14, wherein the compound is one of:

Compound 12

Compound 13

Compound 18
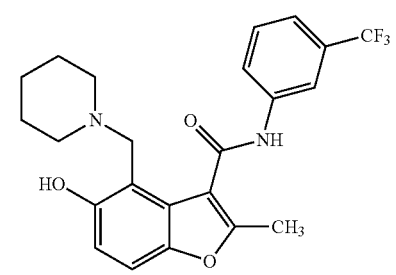
Compound 19
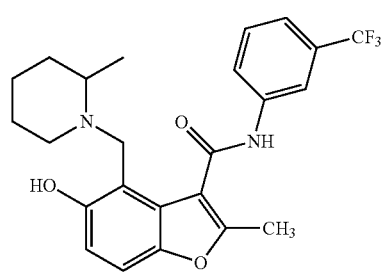 [SMILES: Cc1oc2ccc(O)c(CN3CCCC[C@@H]3C)c2c1C(=O)Nc1cccc(C(F)(F)F)c1]
Compound 20
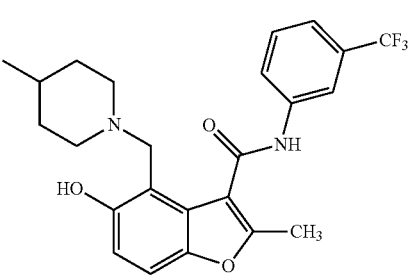
Compound 22
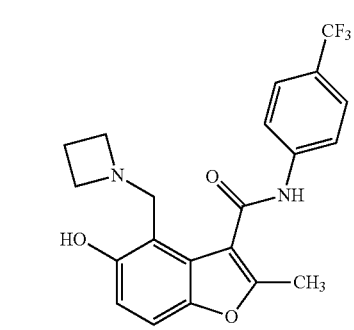
Compound 24
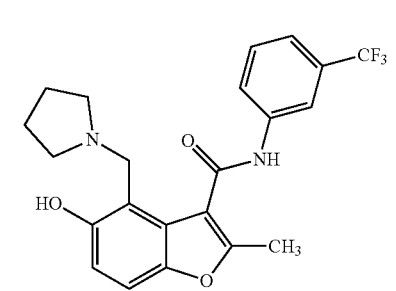
Compound 25
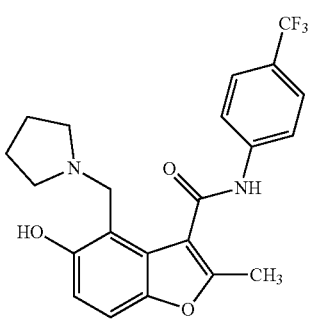
Compound 26
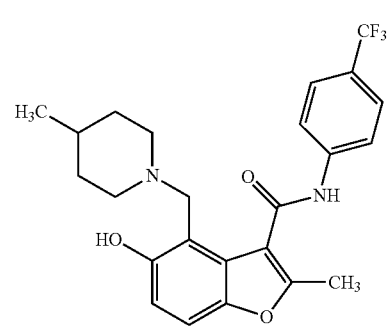
Compound 28
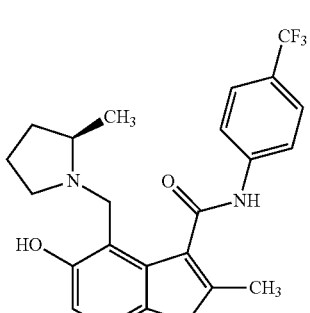
Compound 29
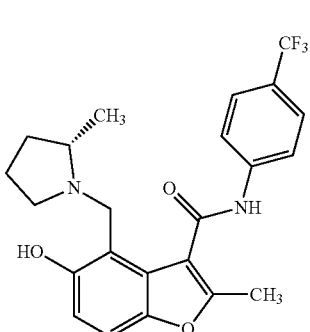
Compound 34
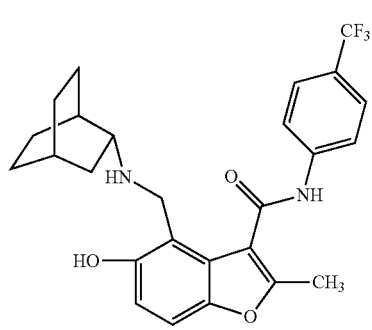

-continued

Compound 36
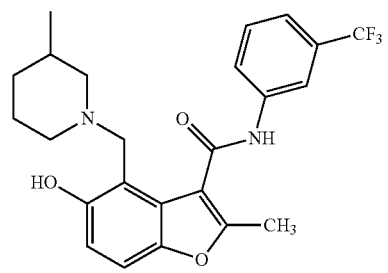

Compound 37
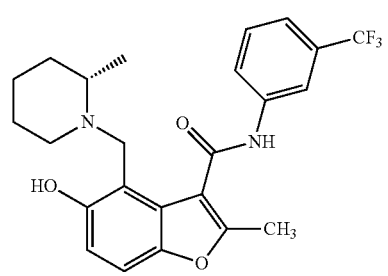

Compound 38
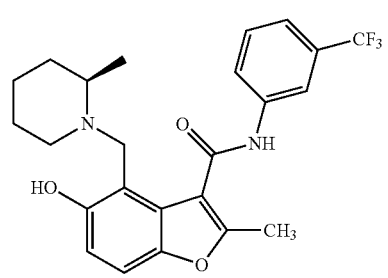 [SMILES: Cc1oc2ccc(O)c(CN3CCCC[C@H]3C)c2c1C(=O)Nc1cccc(C(F)(F)F)c1]

Compound 39
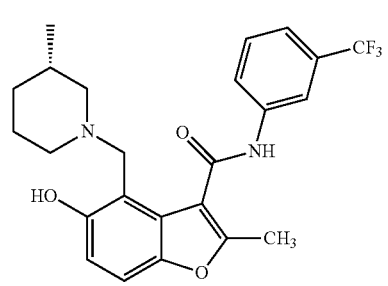

Compound 40
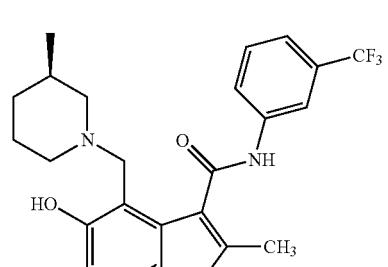

Compound 41
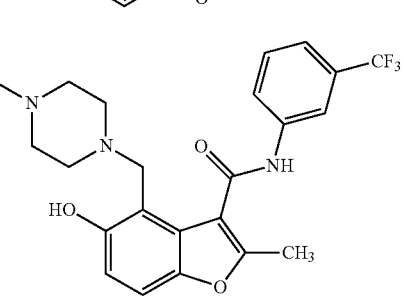

-continued

Compound 42
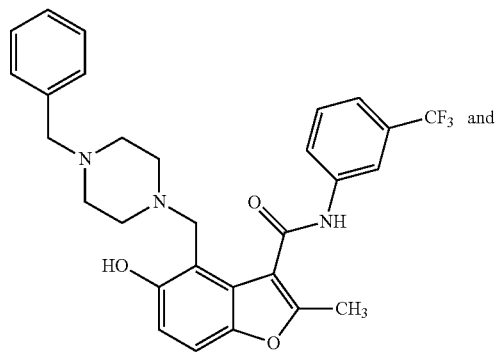
and

Compound 43
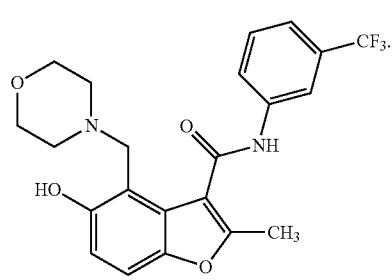

26. A compound, or a pharmaceutically acceptable salt thereof, having a structure of Formula III:

Formula III
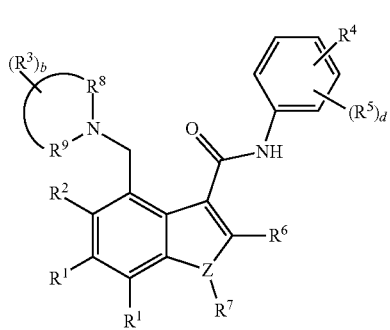

wherein:
each $R^1$ is independently selected from hydrogen or optionally-substituted lower alkyl;
$R^2$ is selected from hydroxyl or halogen;
$R^8$ and $R^9$ together with the linking nitrogen atom form a 4 to 7 membered optionally-substituted N-hetero-mono- or bi-cyclic ring with one or two hetero atoms independently selected from nitrogen and oxygen;
each $R^3$ is independently selected from halogen, lower haloalkyl, or optionally-substituted lower alkyl;
b is 0 to 4;
$R^4$ is trifluoromethyl;
each $R^5$ is independently selected from halogen, lower haloalkyl, or optionally-substituted lower alkyl;
d is 0, 1, or 2;
$R^6$ is methyl;
Z is selected from nitrogen or oxygen; and
if Z is nitrogen, $R^7$ is selected from hydrogen, hydroxyl, halogen, lower haloalkyl, or optionally-substituted lower alkyl, and if Z is oxygen, $R^7$ is not present;

wherein each substituted lower alkyl and substituted N-hetero- mono- or bi-cyclic ring is independently selected from a lower alkyl or N-hetero- mono- or bi-cyclic ring wherein one or more hydrogen atoms are replaced with $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, $C_{1-6}$alkylhalo, $C_{1-6}$alkoxyhalo, carboxyl, cyano, nitro, amino, acyl, amido, aminoacyl, mercapto, alkylthio, thioxo, sulfates, sulfonates, sulfinyl, sulfonyl, sulfonylamido, aryl, ar$C_{1-6}$alkyl, heterocyclyl, heteroaryl, or halogen; and with the proviso that the compound does not comprise the structure set forth as any one of:

Compound 12

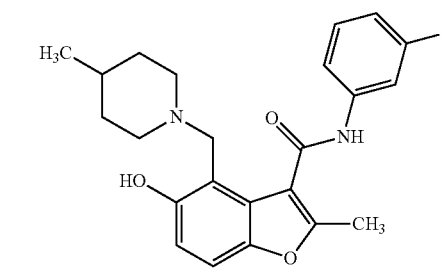

Compound 13

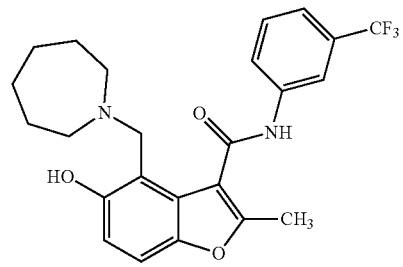

Compound 17

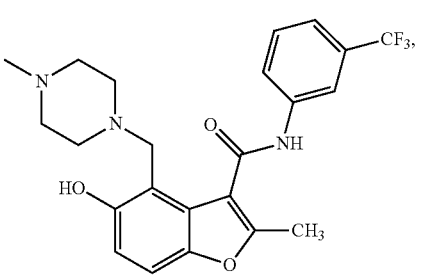

Compound 18

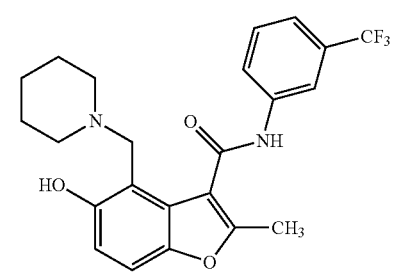

-continued

Compound 19

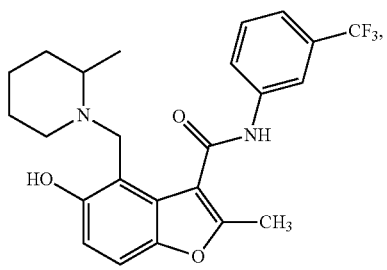

Compound 20

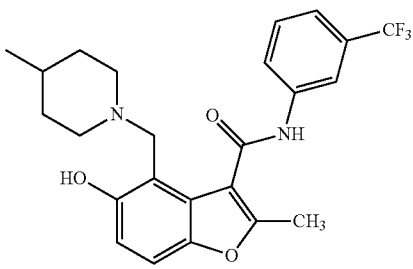

Compound 36

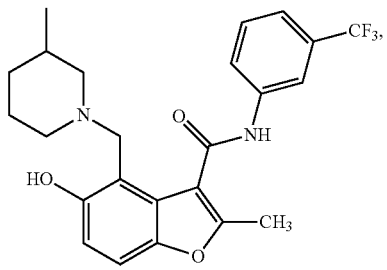

Compound 37

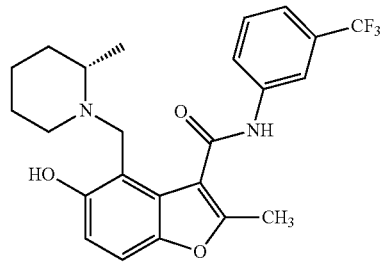

Compound 38

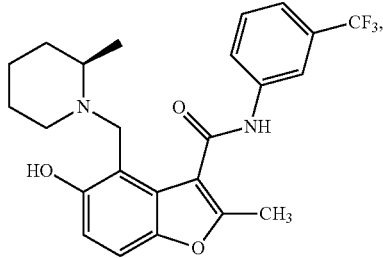

Compound 39

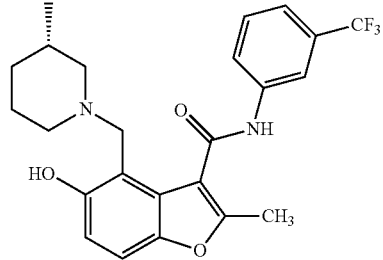 [SMILES: Cc1oc2ccc(O)c(CN3CCC[C@H](C)C3)c2c1C(=O)Nc1cccc(C(F)(F)F)c1]

-continued
Compound 40
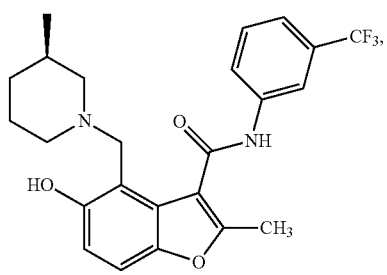
Compound 41
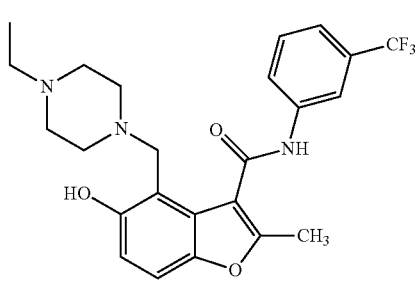 [SMILES: CCN1CCN(Cc2c(O)ccc3oc(C)c(C(=O)Nc4cccc(C(F)(F)F)c4)c23)CC1]
-continued
Compound 42
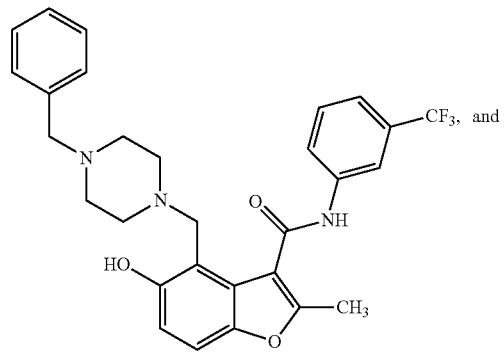
and
Compound 43
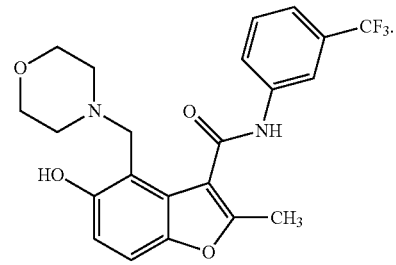
* * * * *